(12) United States Patent
Pizzochero et al.

(10) Patent No.: US 10,967,121 B2
(45) Date of Patent: *Apr. 6, 2021

(54) ROTATIONAL METERING PUMP FOR INSULIN PATCH

(71) Applicant: Becton, Dickinson and Company, Franklin Lakes, NJ (US)

(72) Inventors: Alessandro E. Pizzochero, Chelmsford, MA (US); J. Richard Gyory, Sudbury, MA (US); Kenneth Focht, Needham, MA (US); Justin Fisk, Franklin, MA (US); Joeseph Gordon, Mansfield, MA (US); Matthew Perry, East Greenwich, RI (US); Ajit D'Souza, Lexington, MA (US); Christopher Petroff, Groton, MA (US)

(73) Assignee: BECTON, DICKINSON AND COMPANY, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/521,685

(22) Filed: Jul. 25, 2019

(65) Prior Publication Data

US 2019/0344010 A1 Nov. 14, 2019

Related U.S. Application Data

(63) Continuation-in-part of application No. 16/050,159, filed on Jul. 31, 2018, now Pat. No. 10,675,404, (Continued)

(51) Int. Cl.
*A61M 5/145* (2006.01)
*A61M 5/142* (2006.01)
(Continued)

(52) U.S. Cl.
CPC ...... *A61M 5/14248* (2013.01); *A61M 5/1452* (2013.01); *F04B 7/06* (2013.01);
(Continued)

(58) Field of Classification Search
CPC .......... F04B 53/22; F04B 53/10; F04B 53/16; F04B 17/03; F04B 13/00; F04B 53/14;
(Continued)

(56) References Cited

U.S. PATENT DOCUMENTS 2,291,601 A    8/1942  Bancroft
3,994,632 A *  11/1976 Schreiber .............. F01B 3/0079
                                                  417/534

(Continued)

FOREIGN PATENT DOCUMENTS

| CH | 688224 A5 | 6/1997 |
| FR | 2661740 | 8/1991 |
| JP | 2013-502522 A | 1/2013 |

*Primary Examiner* — Devon C Kramer
*Assistant Examiner* — David N Brandt
(74) *Attorney, Agent, or Firm* — Dickinson Wright PLLC

(57) ABSTRACT

A rotary pump for a fluid metering system is provided. The rotary pump reciprocates, and is reversed by a signal from a limit switch that is deflected by an actuator arm on a rotating sleeve of the pump system. The rotary pump includes a plunger and optional stopper formed from a two-shot molding process, and including seals overmolded onto the head of the plunger and the head of the optional stopper.

11 Claims, 100 Drawing Sheets

Related U.S. Application Data which is a continuation-in-part of application No. 15/300,695, filed as application No. PCT/US2015/024517 on Apr. 6, 2015, now Pat. No. 10,132,308.

(60) Provisional application No. 61/976,361, filed on Apr. 7, 2014.

(51) Int. Cl.
| | |
|---|---|
| *F04B 13/00* | (2006.01) |
| *F04B 7/06* | (2006.01) |
| *F04B 17/03* | (2006.01) |
| *F04B 19/22* | (2006.01) |
| *F04B 53/16* | (2006.01) |

(52) U.S. Cl.
CPC ... *F04B 13/00* (2013.01); *A61M 2005/14506* (2013.01); *F04B 17/03* (2013.01); *F04B 19/22* (2013.01); *F04B 53/16* (2013.01)

(58) Field of Classification Search
CPC .......... F04B 7/007; F04B 7/06; F04B 7/0046; F04B 49/12; F04B 19/025; F04B 9/047; F04B 19/22; F04B 9/045; A61M 5/14248; A61M 5/1452; A61M 2005/14506
See application file for complete search history.

(56) References Cited

U.S. PATENT DOCUMENTS

| | | |
|---|---|---|
| 4,036,326 A | 7/1977 | Mukai et al. |
| 4,445,828 A | 5/1984 | Sontheimer |
| 4,543,515 A * | 9/1985 | Suzuki ............... H02P 1/22 200/12 |
| 4,685,870 A | 8/1987 | Kato |
| 5,385,992 A | 1/1995 | Koskinen et al. |
| 5,478,217 A | 12/1995 | Jones |
| 5,494,420 A | 2/1996 | Mashirt et al. |
| 5,741,126 A | 4/1998 | Stearns et al. |
| 6,116,660 A * | 9/2000 | Langkamp, Jr. ...... E05B 17/002 292/65 |
| 9,664,186 B2 | 5/2017 | Roberts et al. |
| 2010/0303655 A1 | 12/2010 | Scekic |
| 2013/0017099 A1 | 7/2013 | Genoud et al. |
| 2016/0213851 A1 | 7/2016 | Weibel et al. |
| 2017/0184091 A1* | 6/2017 | Focht ............... A61M 5/1452 |

* cited by examiner

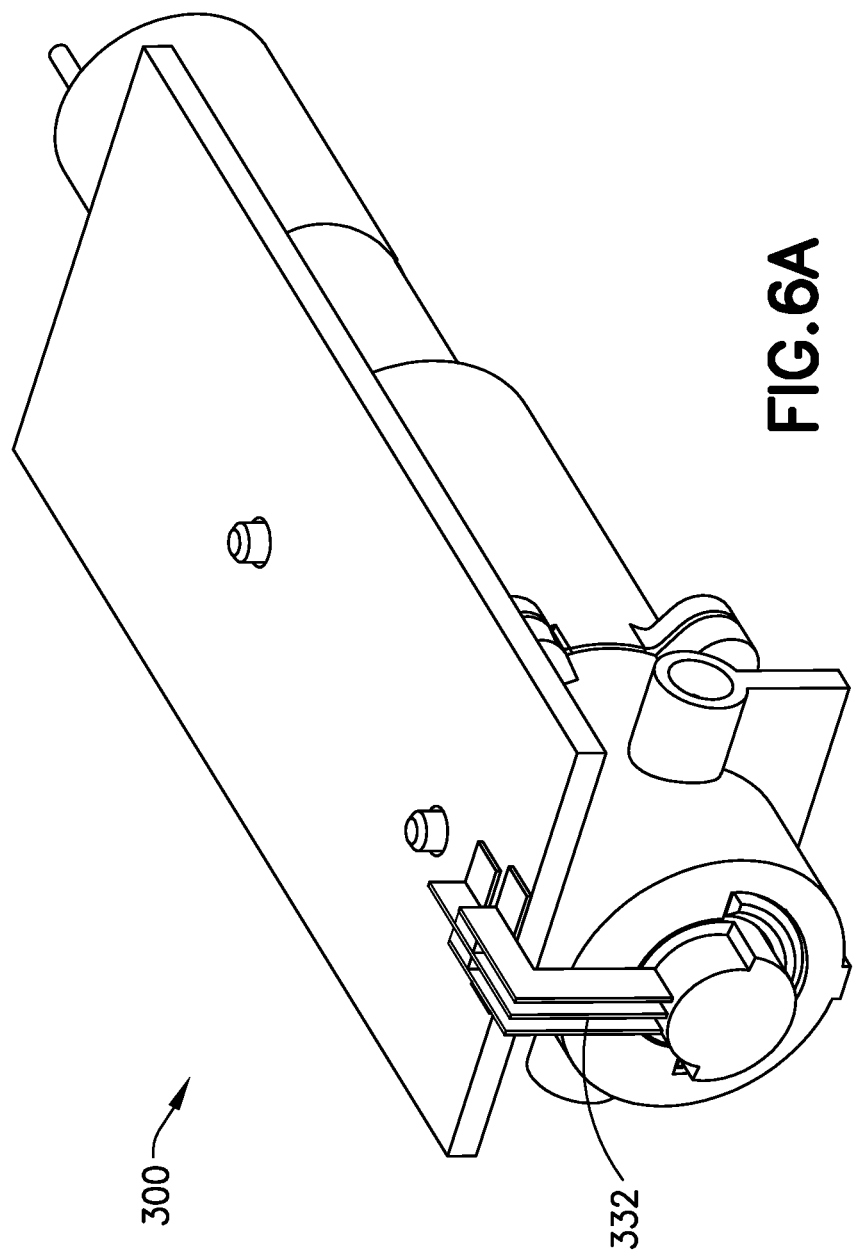

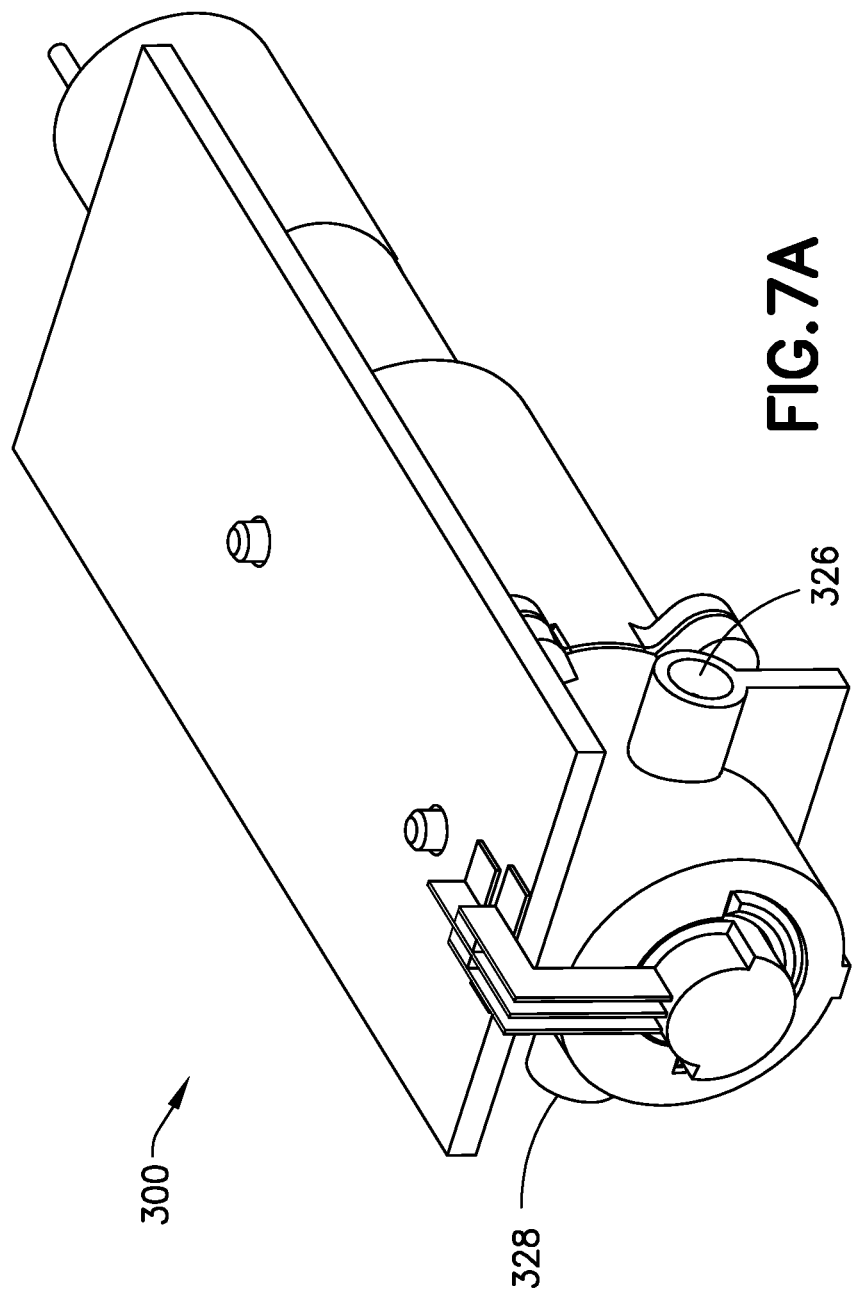

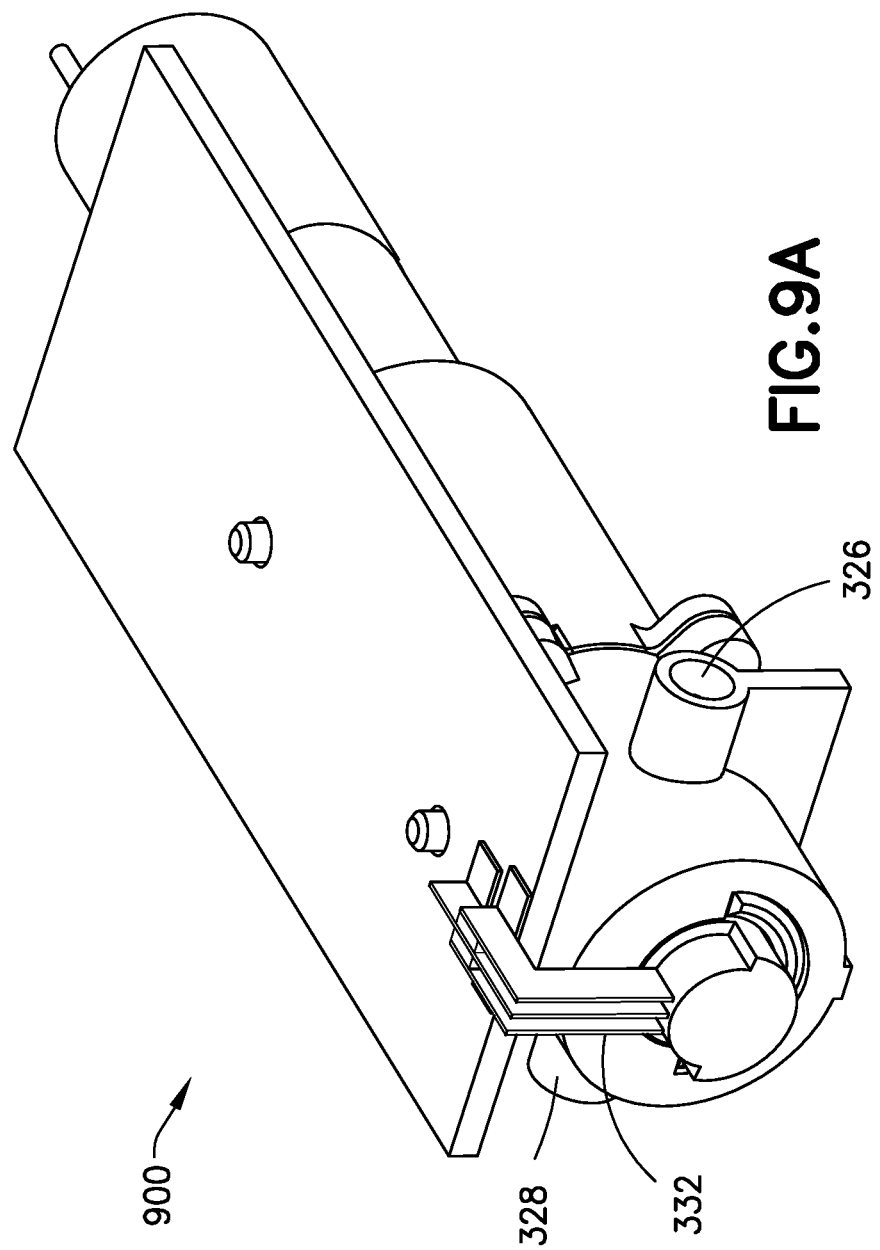

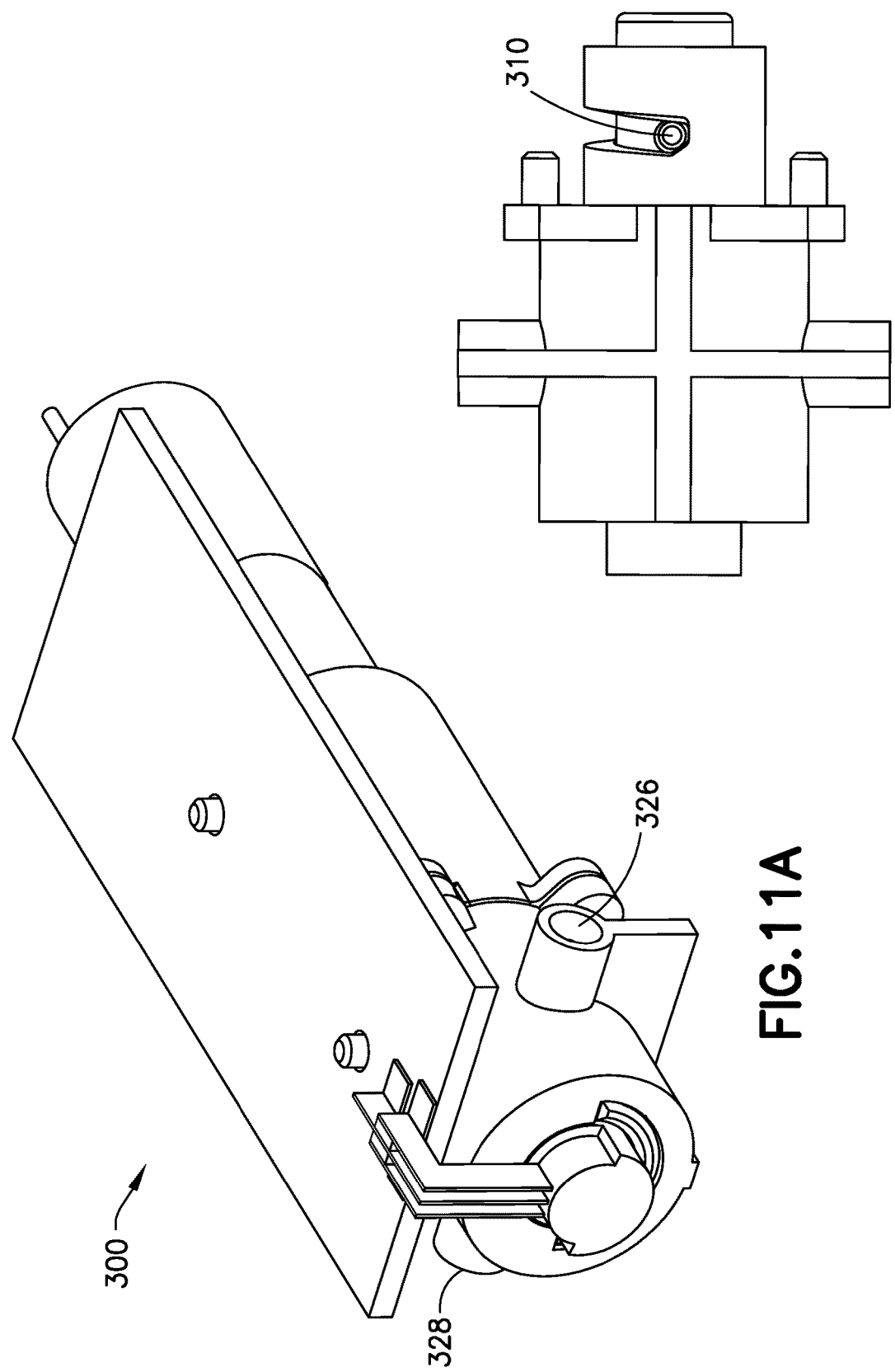

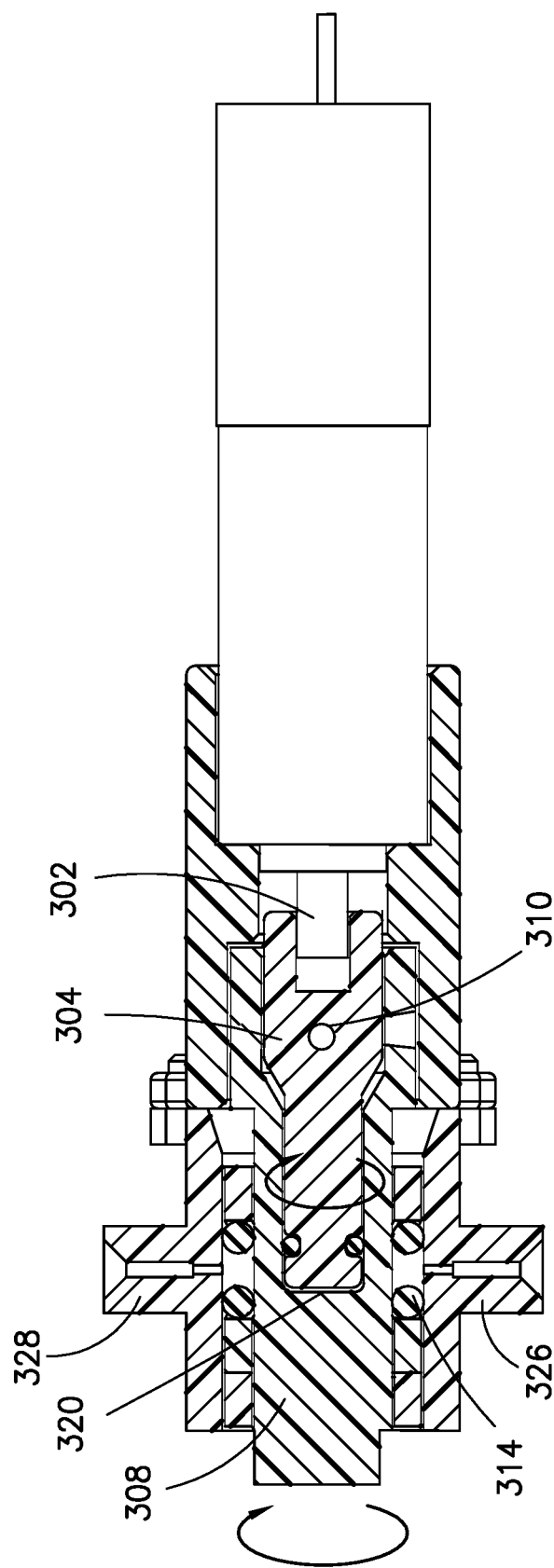

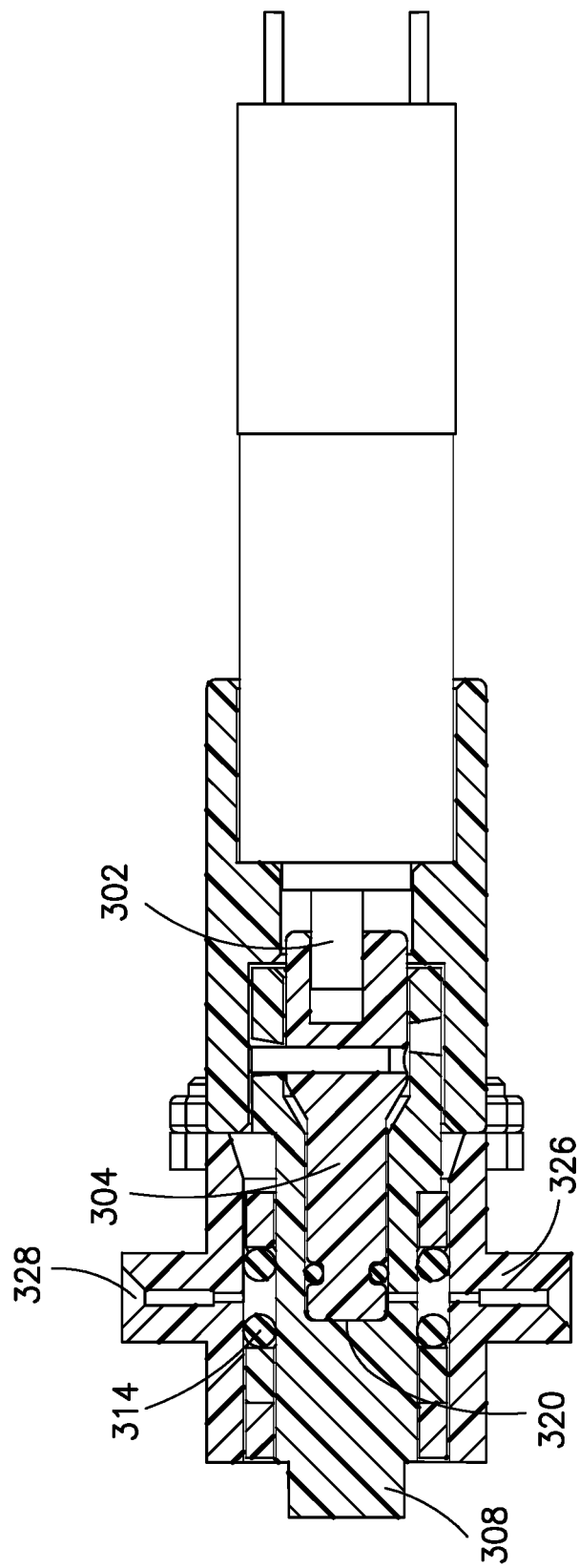

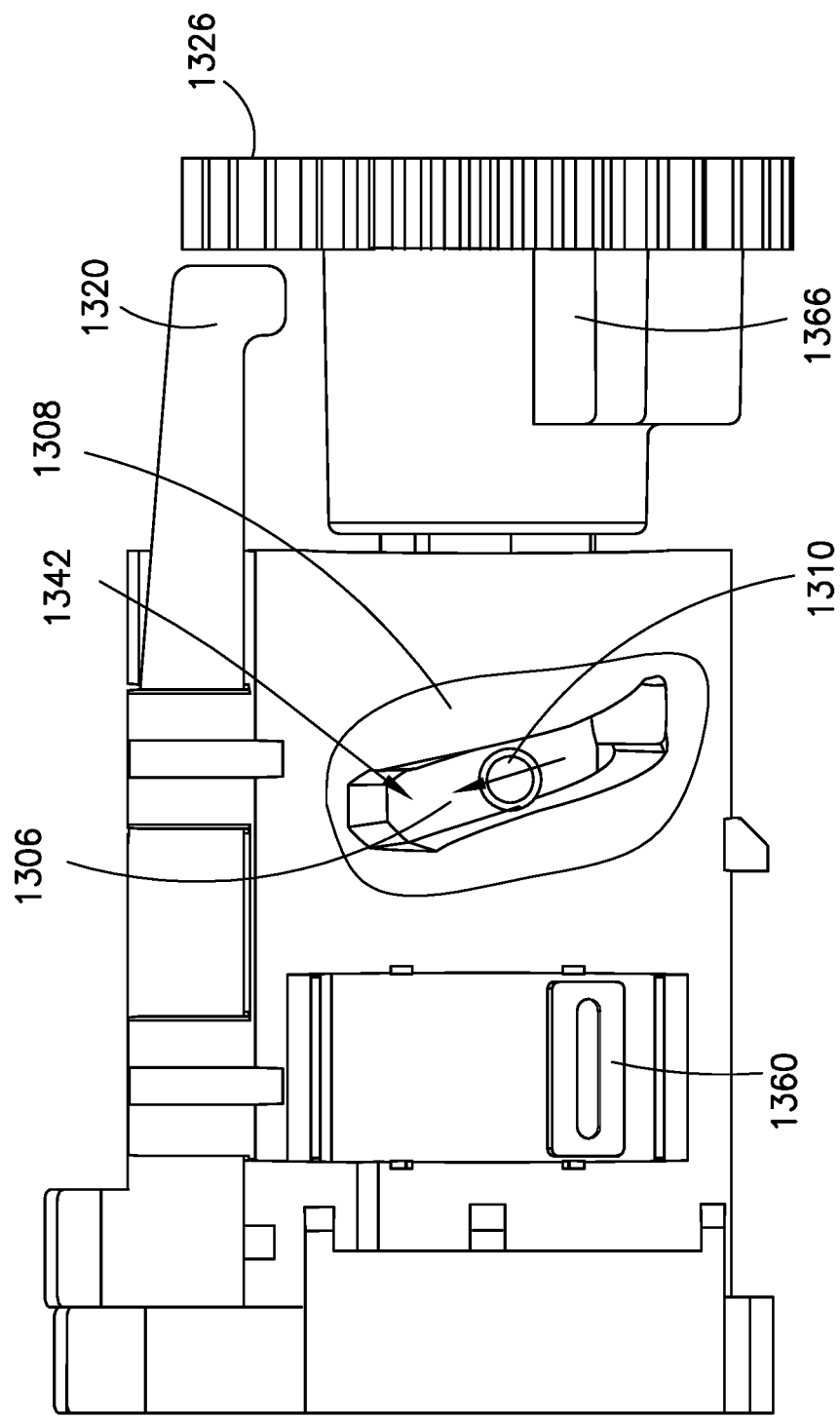

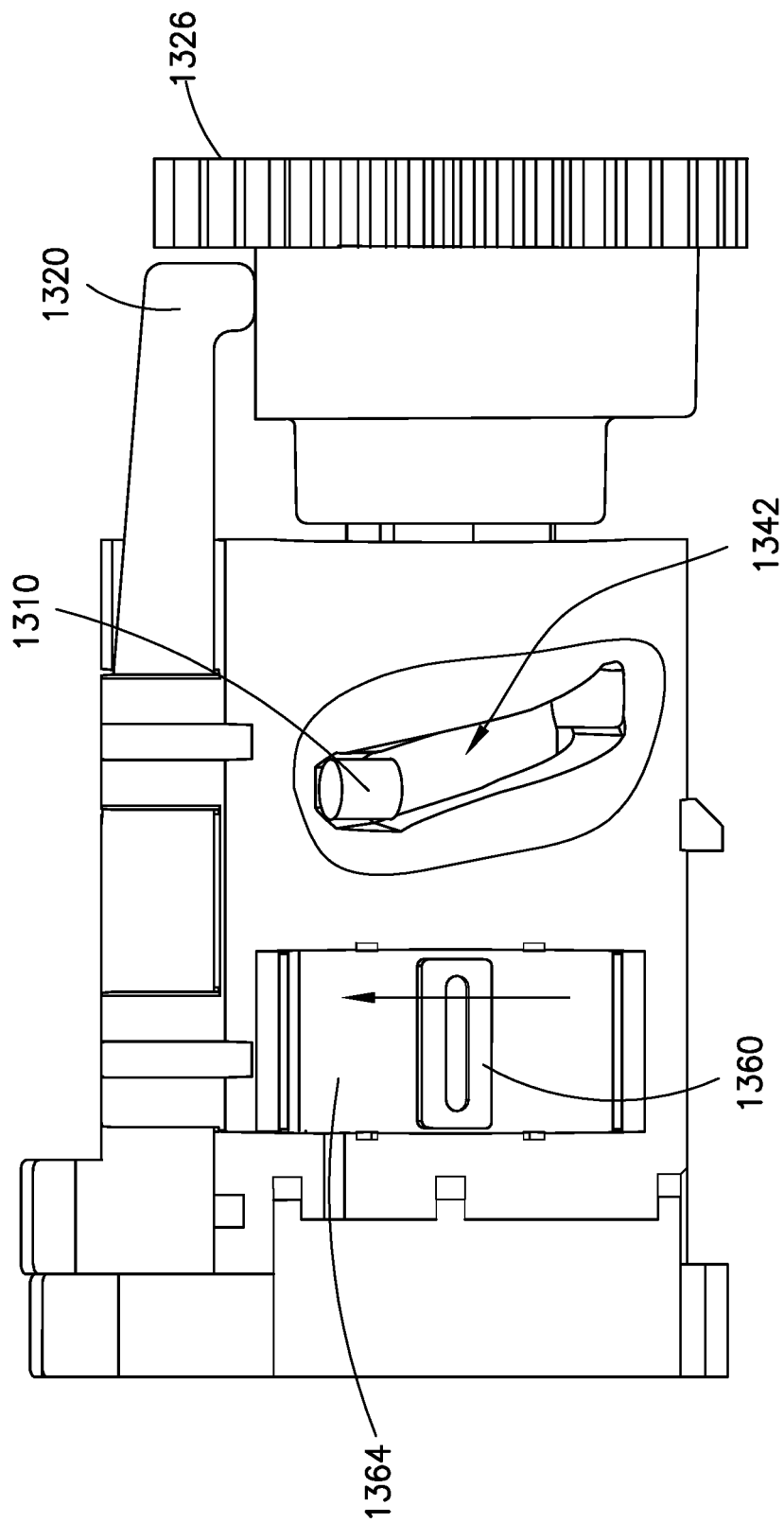

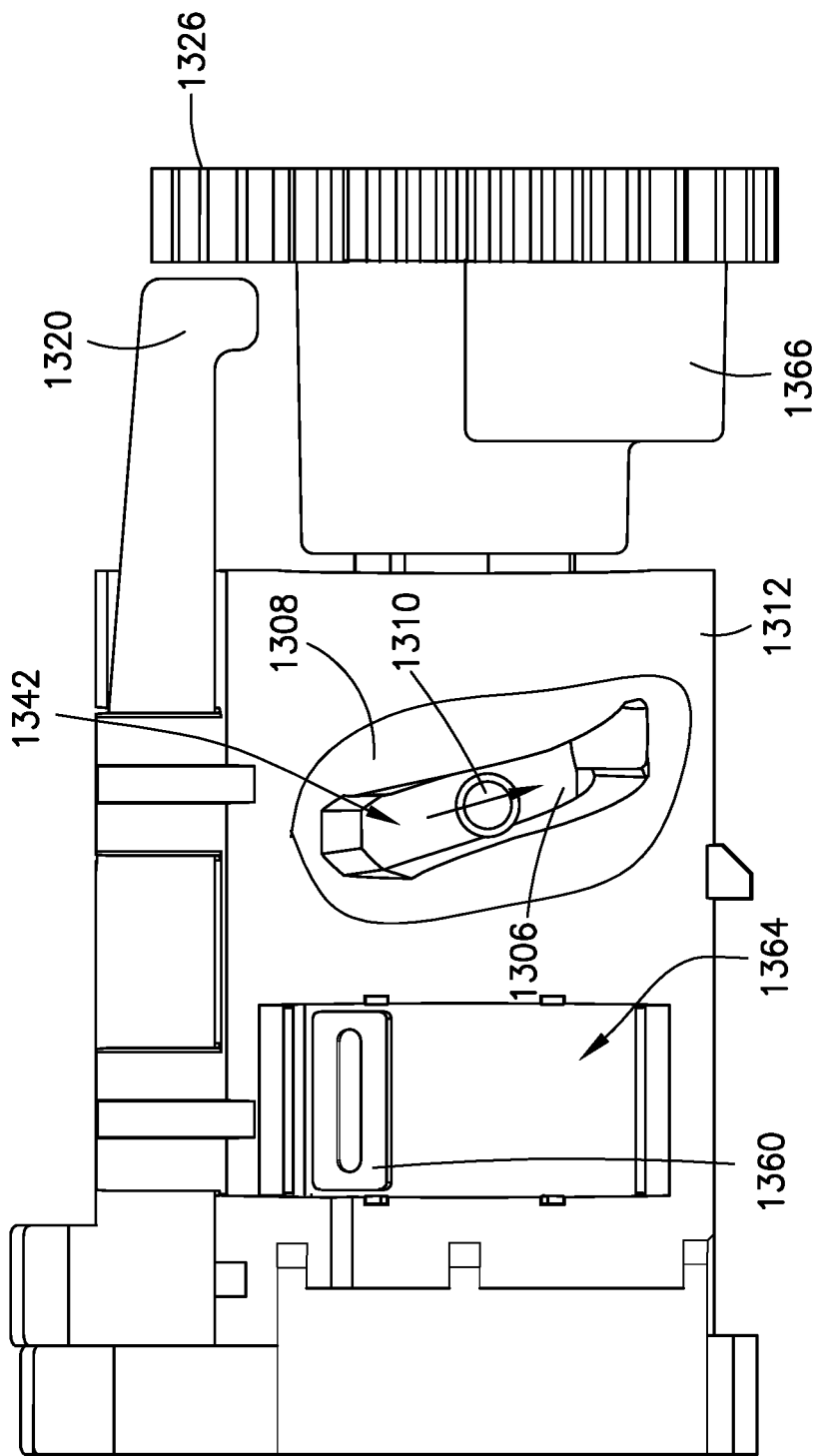

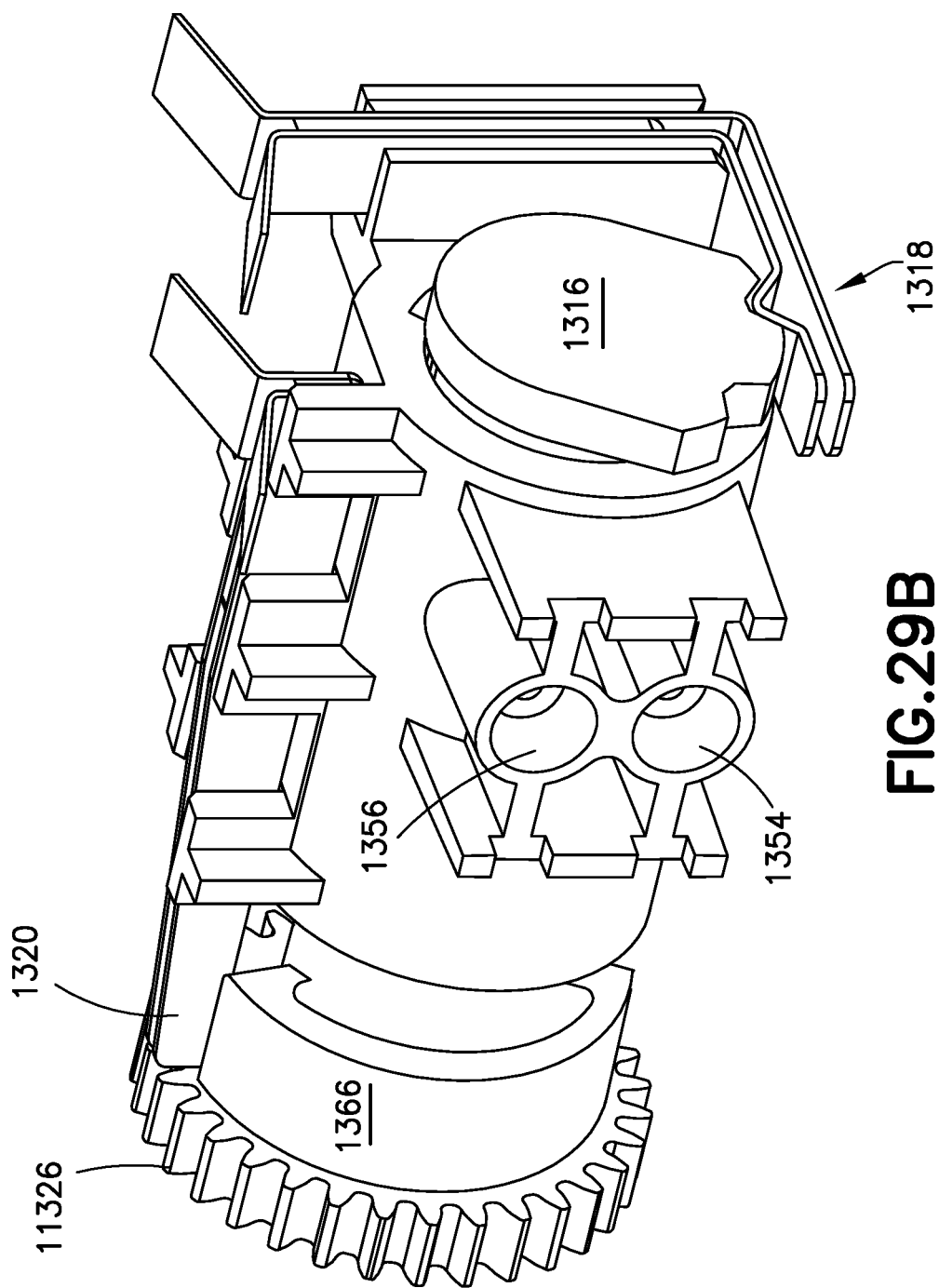

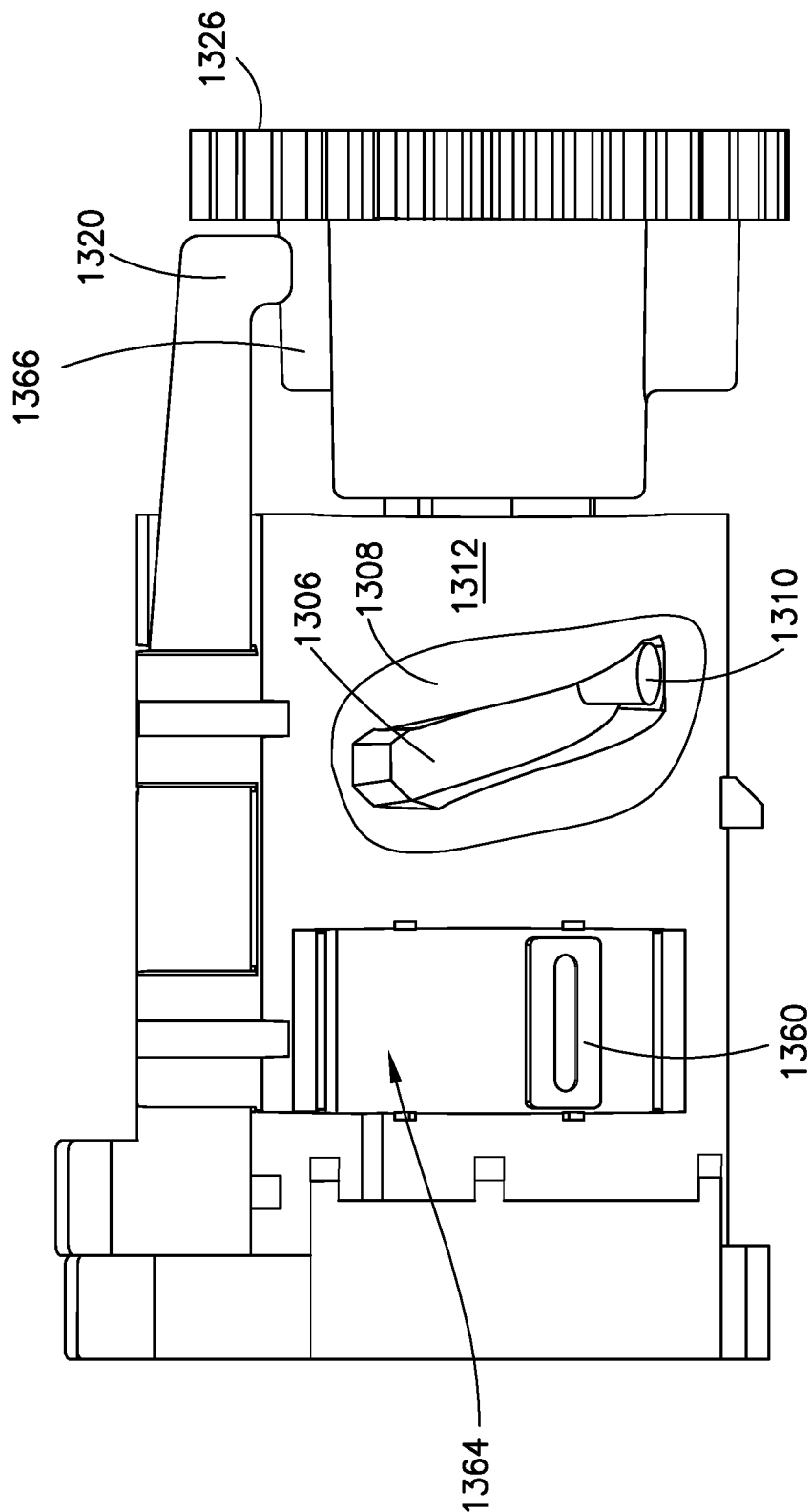

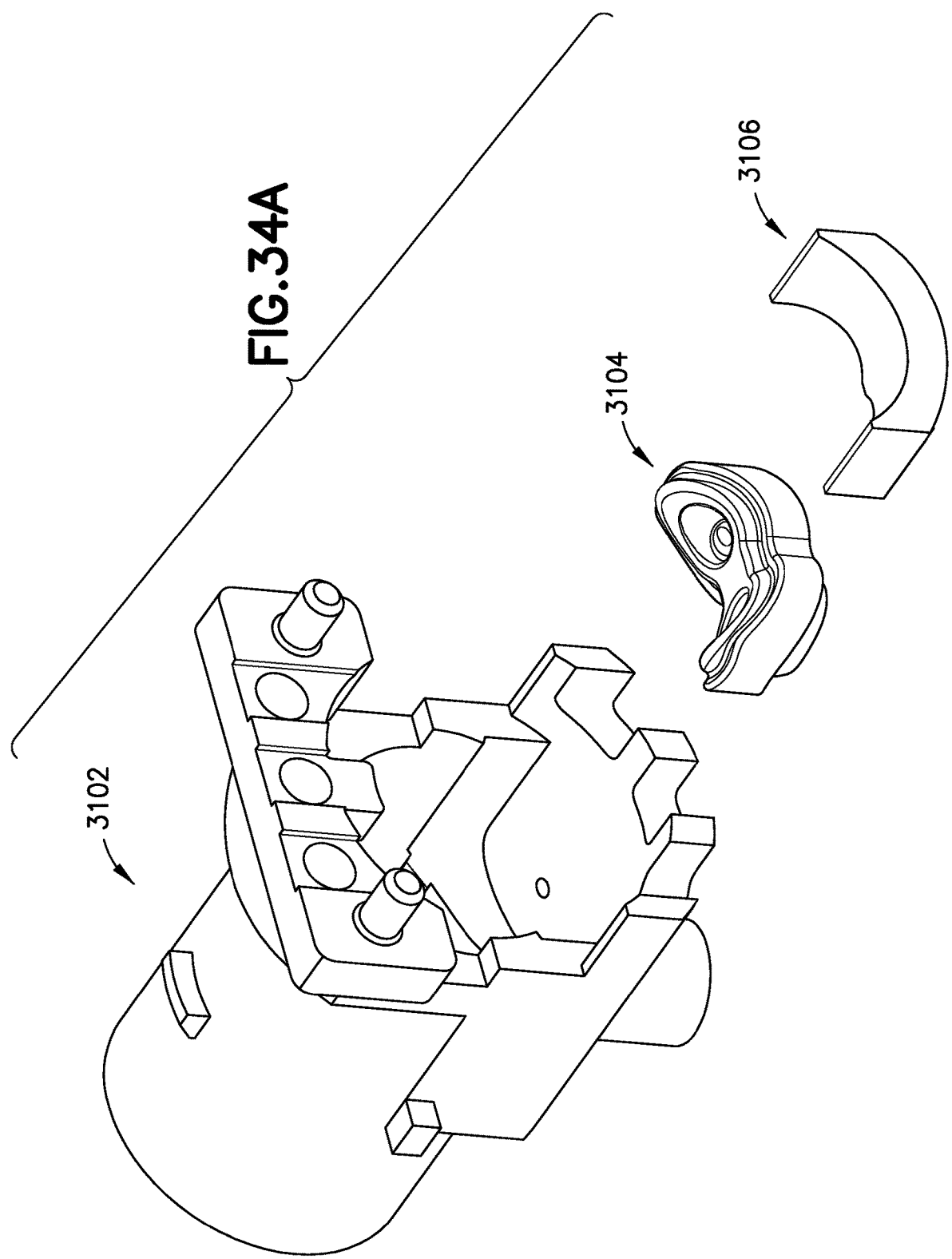

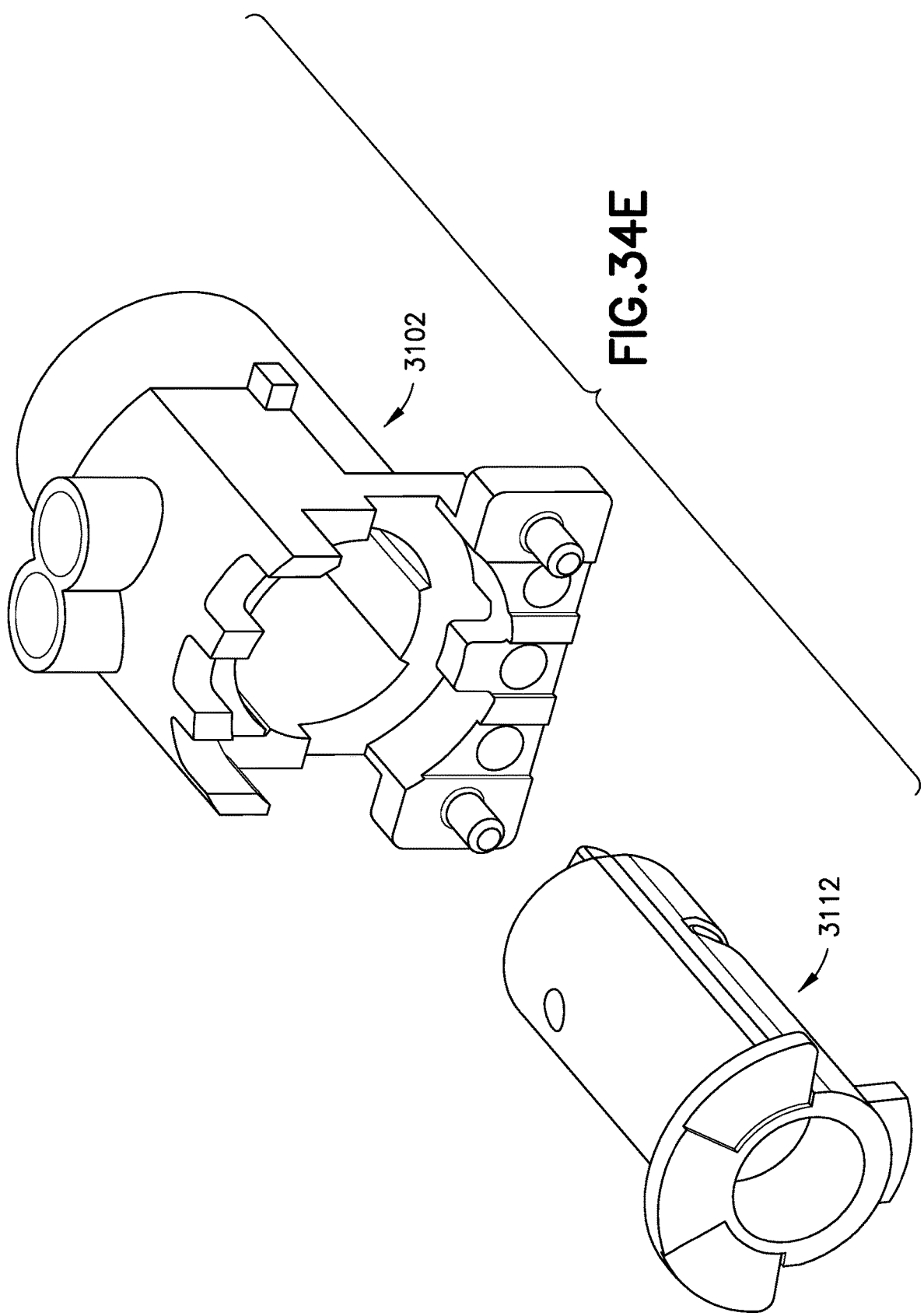

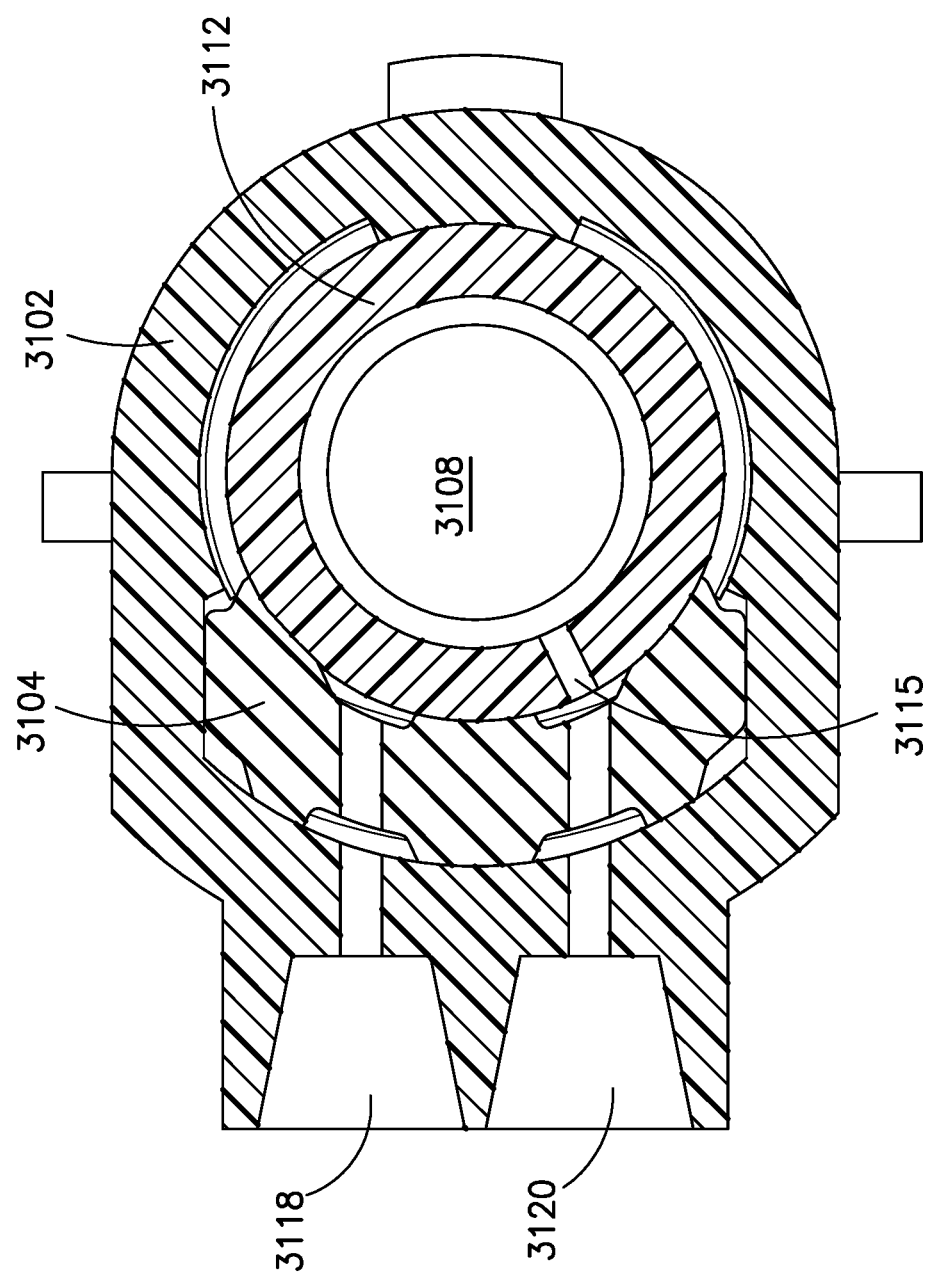

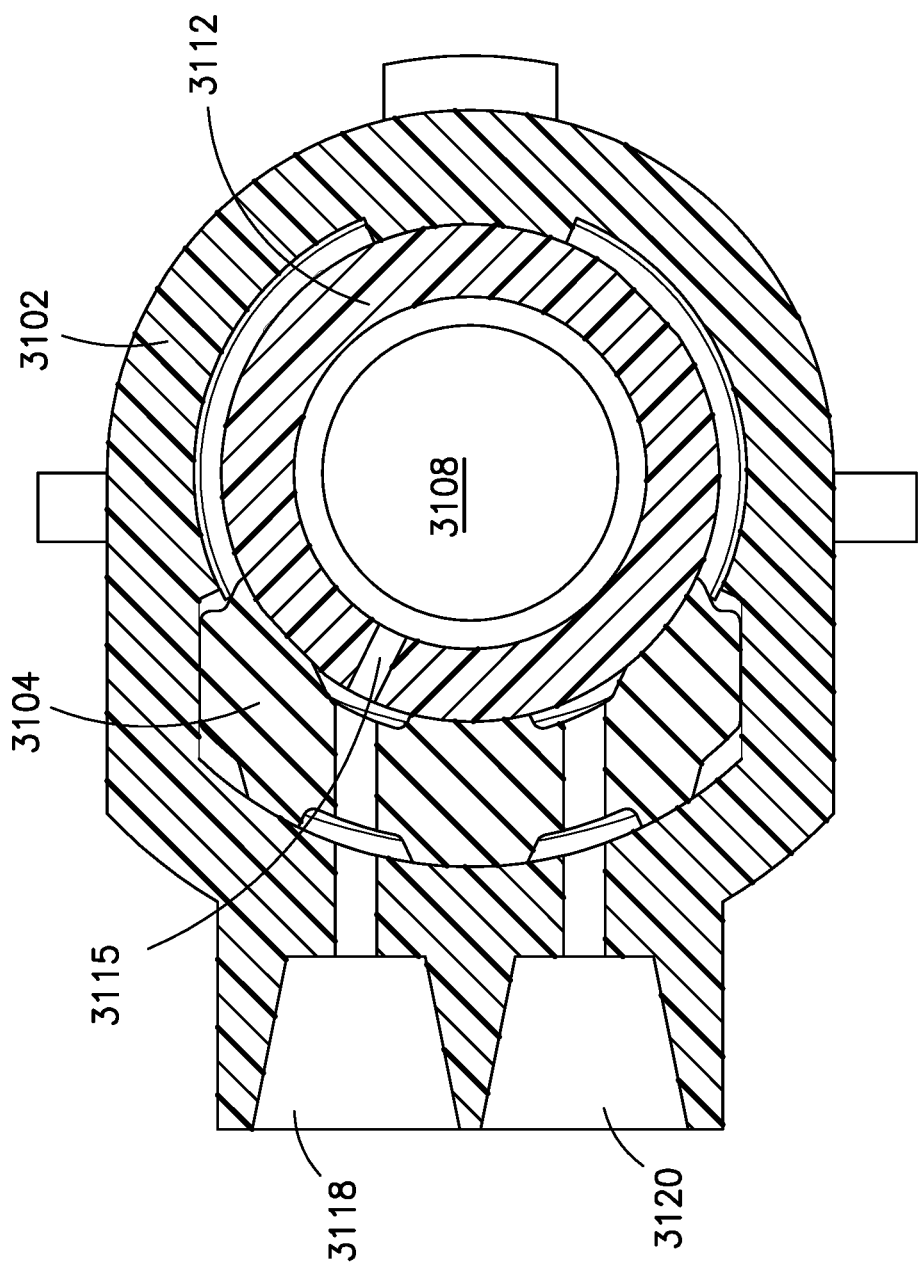

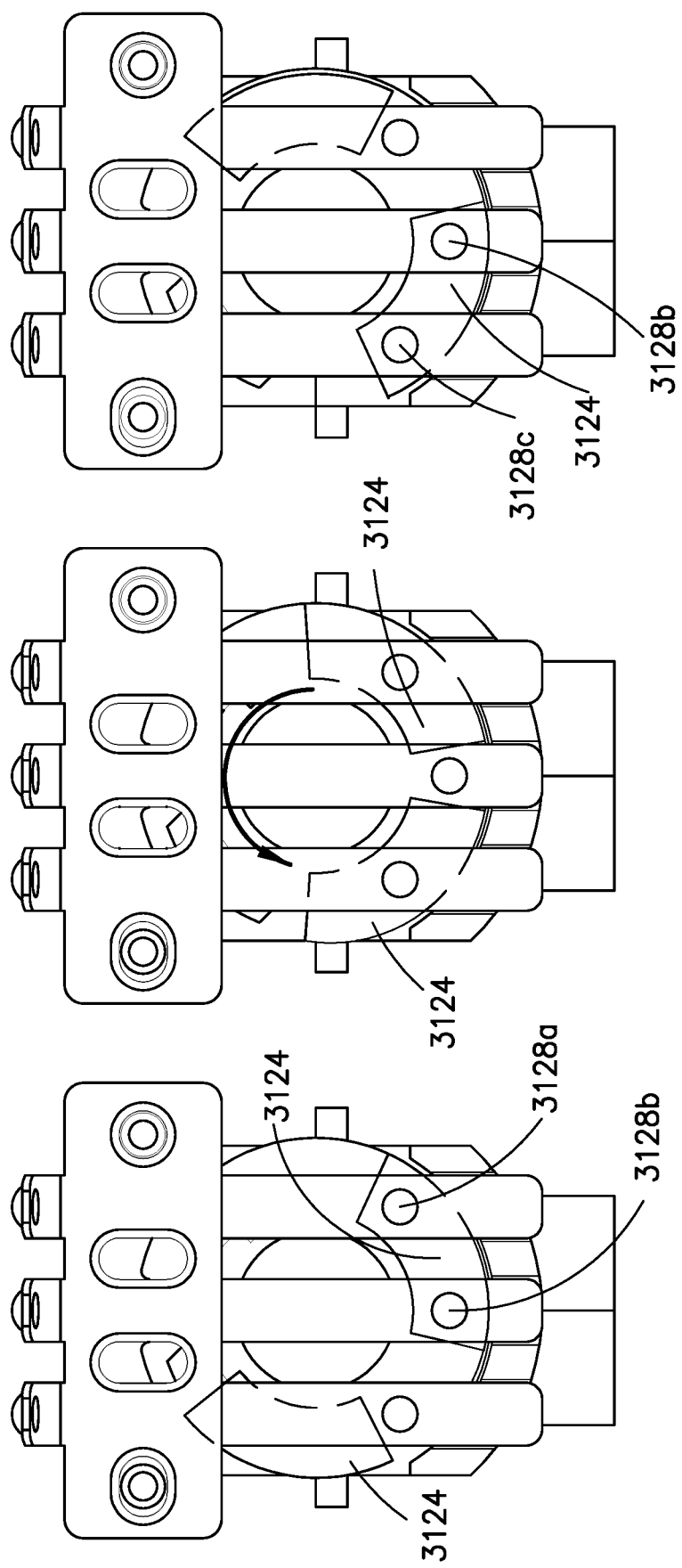

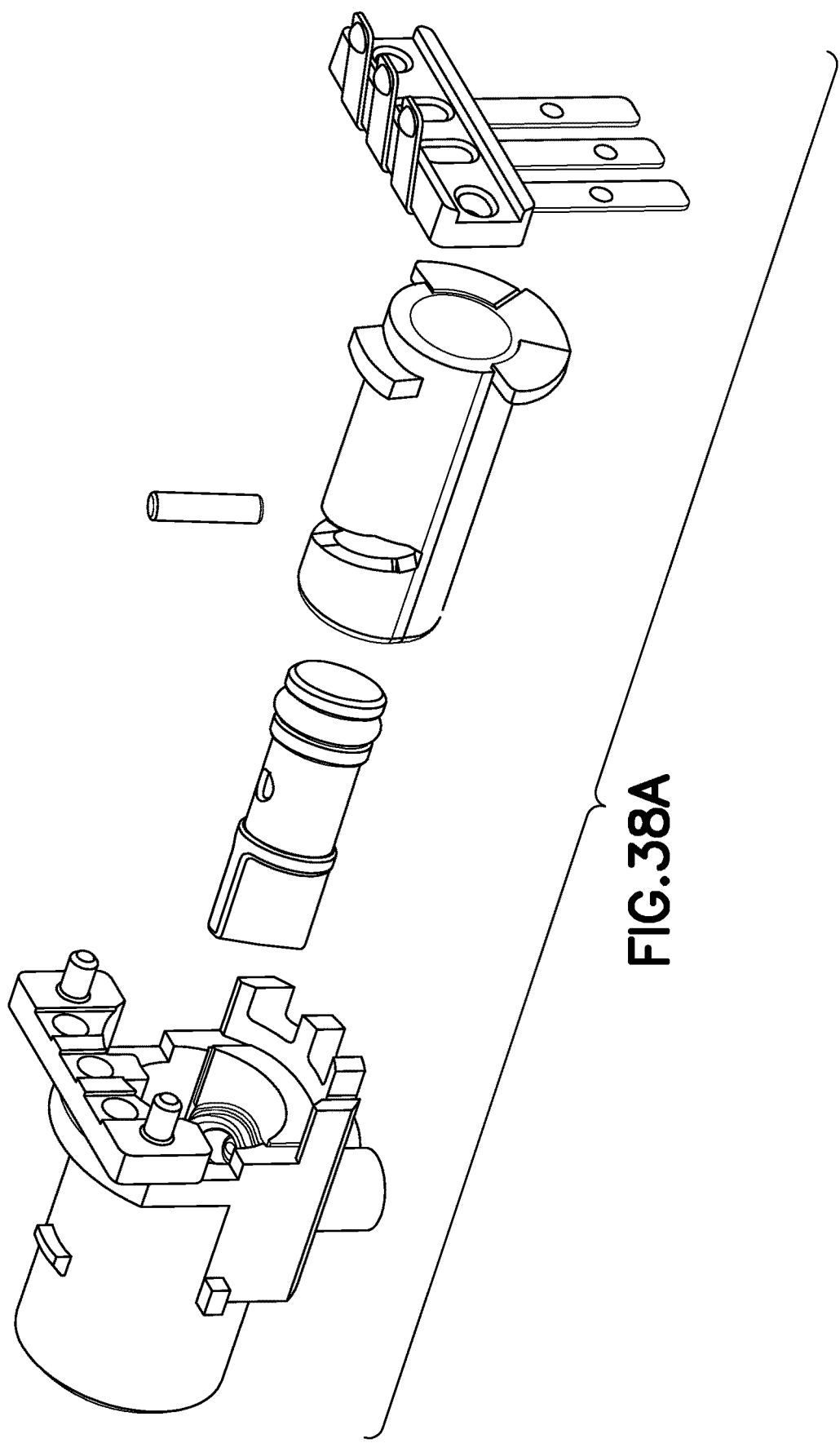

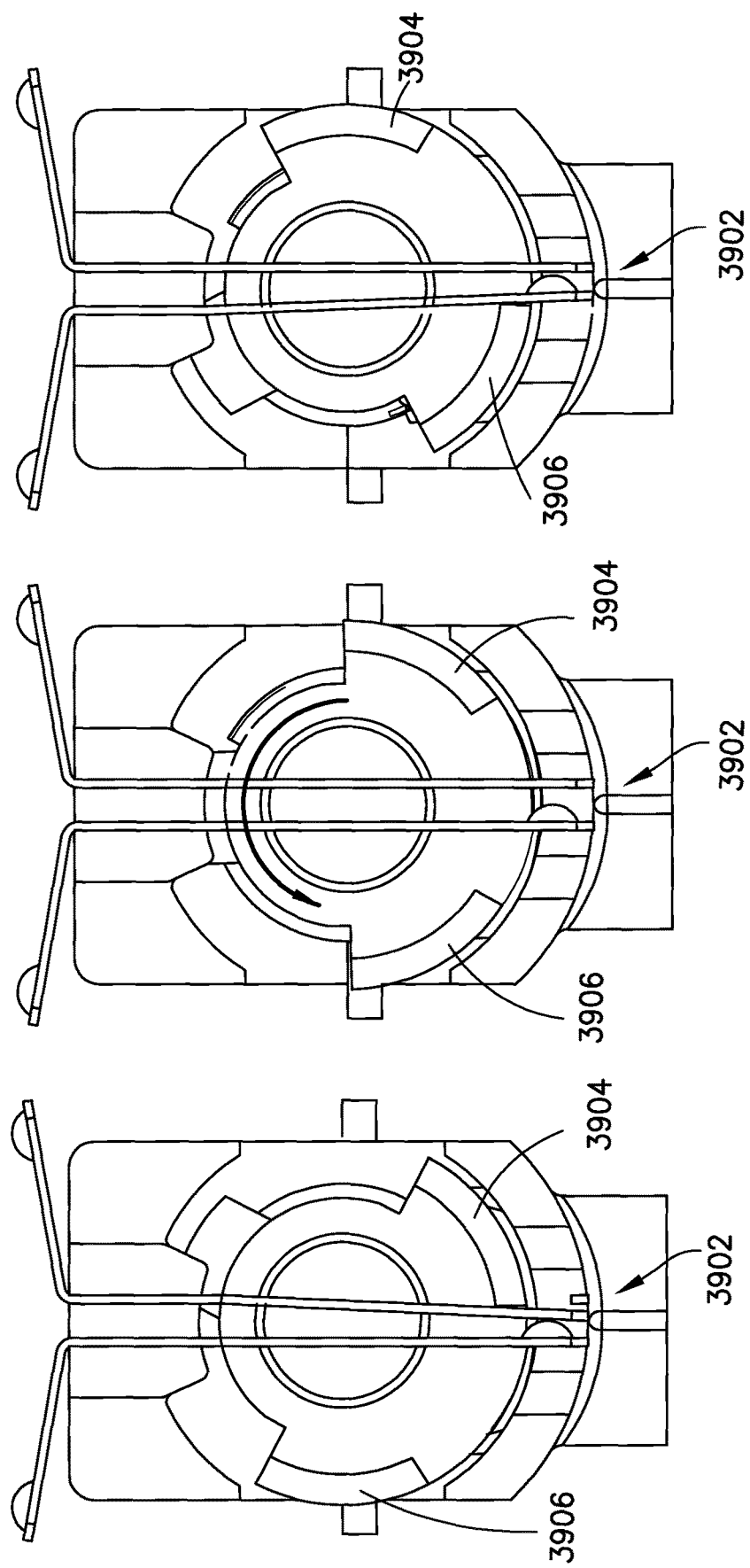

ROTATIONAL METERING PUMP FOR INSULIN PATCH

RELATED APPLICATIONS

This application is a continuation-in-part of U.S. patent application Ser. No. 16/050,159 filed Jul. 31, 2018, which was a continuation-in-part of U.S. patent application Ser. No. 15/300,695, filed Sep. 29, 2016, which was the U.S. national stage of International Application No. PCT/US2015/024517, filed on Apr. 6, 2015, which claims priority to U.S. Provisional Application No. 61/976,361, filed Apr. 7, 2014. Each of these applications is hereby incorporated by reference in its entirety.

FIELD OF THE INVENTION

The present invention relates generally to metering systems for use in wearable medication infusion patches.

BACKGROUND OF THE INVENTION

Diabetes is a group of diseases marked by high levels of blood glucose resulting from defects in insulin production, insulin action, or both. Diabetes can lead to serious health complications and premature death, but there are well-known products available for people with diabetes to help control the disease and lower the risk of complications.

Treatment options for people with diabetes include specialized diets, oral medications and/or insulin therapy. The primary goal for diabetes treatment is to control the patient's blood glucose (sugar) level in order to increase the chances of a complication-free life. It is not always easy, however, to achieve good diabetes management, while balancing other life demands and circumstances.

Currently, there are two principal modes of daily insulin therapy for the treatment of type 1 diabetes. The first mode includes syringes and insulin pens that require a needle stick at each injection, typically three to four times per day. These devices are simple to use and relatively low in cost. Another widely adopted and effective method of treatment for managing diabetes is the use of an insulin pump. Insulin pumps can help users keep their blood glucose levels within target ranges based on their individual needs, by providing continuous infusion of insulin at varying rates to more closely mimic the behavior of the pancreas. By using an insulin pump, users can match their insulin therapy to their lifestyles, rather than matching their lifestyles to how an insulin injection is working for them.

However, conventional insulin pumps suffer from several drawbacks. For example, lead screw and piston type metering systems typically used in insulin pumps are often cumbersome to users, requiring a large height and a large a footprint.

Conventional insulin pumps also typically require a large number of components and moving parts, thereby increasing risks of mechanical failure.

Conventional insulin pumps also typically have too long a tolerance loop for dose accuracy, depending on too many factors, which are sometimes difficult to ascertain. This can result in a loss in dose accuracy.

Conventional insulin pumps also typically have too complex a fluid path. This can result in complicated or inadequate priming and air removal.

Conventional insulin pumps also typically require high precision actuators, thereby increasing the cost of conventional patch pumps.

Some insulin pumps are also at risk of creating direct fluid paths between a reservoir and a cannula of an insulin patch. This can result in an overdose to a user.

Conventional insulin pumps also typically require complex sensing schemes. This can result in increased cost and reduced accuracy and reliability.

Conventional insulin pumps also typically have valves that are prone to leaking at elevated system back pressures. This can result in reduced accuracy and reliability.

Conventional insulin pumps also typically require large working volumes and large system volumes exposed to potentially high back pressure. This can result in reduced accuracy and reliability.

Conventional insulin patches also typically have low efficiency motors requiring large batteries, thereby increasing the size of the insulin patch.

Accordingly, there is a need for a metering system with reduced height and footprint, compared to conventional lead screw and piston type metering systems, to increase comfort to users.

There is also a need for a metering system with a reduced number of components and moving parts, compared to conventional insulin pumps, to increase the mechanical safety of insulin patches.

There is also a need for a metering system with a short tolerance loop for dose accuracy, which depends on few factors, compared to conventional metering pumps, thereby increasing dose accuracy.

There is also a need for a metering system with a simple fluid path, compared to conventional metering systems, thereby simplifying priming and air removal.

There is also a need for a metering system utilizing a low precision actuator, compared to conventional metering systems, thereby reducing the cost of insulin patches.

There is also a need for a metering system with no direct fluid path between the reservoir and the cannula, compared to conventional metering systems, thereby better safeguarding a user against overdose.

There is also a need for a metering system with simple sensing schemes, compared to conventional metering systems, thereby reducing cost and increasing accuracy and reliability of insulin patches.

There is also a need for a metering system with valves that are robust with respect to leaking at elevated system back pressures, compared to conventional metering systems, thereby increasing accuracy and reliability of insulin patches.

There is also a need for a metering system with a small working volume and a low system volume exposed to potentially high back pressure, compared to conventional metering systems, thereby increasing accuracy and reliability of insulin patches.

There is also a need for a metering system requiring a high efficiency motor with small batteries, compared to conventional metering systems, thereby reducing the size of insulin patches.

SUMMARY OF THE INVENTION

An aspect of illustrative embodiments of the present invention is to substantially address the above and other concerns, and provide a small and reliable metering system.

An aspect of illustrative embodiments of the present invention is to provide a metering system with reduced height and footprint, compared to conventional lead screw and piston type metering systems, to increase comfort to users.

Another aspect of illustrative embodiments of the present invention is to provide a metering system with a reduced number of components and moving parts, compared to conventional insulin pumps, to increase the mechanical safety of insulin patches.

Another aspect of illustrative embodiments of the present invention is to provide a metering system with a short tolerance loop for dose accuracy, which depends on few factors, compared to conventional metering pumps, thereby increasing dose accuracy. For example, in illustrative embodiments of the present invention, the tolerance loop for dose accuracy is short, and depends upon only two readily measurable dimensions: a pump diameter and an axial dimension of a helical slot.

Another aspect of illustrative embodiments of the present invention is to provide a metering system with a simple fluid path, compared to conventional metering systems, thereby simplifying priming and air removal.

Another aspect of illustrative embodiments of the present invention is to provide a metering system utilizing a low precision actuator, compared to conventional metering systems, thereby reducing the cost of insulin patches. For example, in illustrative embodiments of the present invention, a mechanism can over-rotate at both ends of a stroke and still maintain dose accuracy.

Another aspect of illustrative embodiments of the present invention is to provide a metering system with no direct fluid path between the reservoir and the cannula, compared to conventional metering systems, thereby better safeguarding a user against overdose.

Another aspect of illustrative embodiments of the present invention is to provide a metering system with simple sensing schemes, compared to conventional metering systems, thereby reducing cost and increasing accuracy and reliability of insulin patches. For example, in illustrative embodiments of the present invention, sensing schemes are based on contact switches.

Another aspect of illustrative embodiments of the present invention is to provide a metering system in which the mechanical stroke of a pump allows for easy triggering of a cannula insertion mechanism.

Another aspect of illustrative embodiments of the present invention is to provide a metering system with valves that are robust with respect to leaking at elevated system back pressures, compared to conventional metering systems, thereby increasing accuracy and reliability of insulin patches. For example, in illustrative embodiments of the present invention, valves have no volume change when moving between states.

Another aspect of illustrative embodiments of the present invention is to provide a metering system with a small working volume and a low system volume exposed to potentially high back pressure, compared to conventional metering systems, thereby increasing accuracy and reliability of insulin patches.

Another aspect of illustrative embodiments of the present invention is to provide a metering system using a high efficiency motor with small batteries, compared to conventional metering systems, thereby reducing the size of insulin patches.

The foregoing and/or other aspects of the present invention are achieved by providing a metering system for use in a wearable insulin infusion patch. For example, in illustrative embodiments of the present invention, the metering system is part of a larger fluidics sub-system that includes a flexible reservoir for storing insulin and a cannula assembly for delivering the insulin into sub-cutaneous tissue. The metering system draws a small dose of fluid from the reservoir and then pushes it down the cannula line and into the patient. The fluid dose is small relative to the reservoir volume, such that many pump strokes are required to completely empty the reservoir.

Additional and/or other aspects and advantages of the present invention will be set forth in the description that follows, or will be apparent from the description, or may be learned by practice of the invention. The present invention may comprise a method or apparatus or system having one or more of the above aspects, and/or one or more of the features and combinations thereof. The present invention may comprise one or more of the features and/or combinations of the above aspects as recited, for example, in the attached claims.

BRIEF DESCRIPTION OF THE DRAWINGS

The various objects, advantages and novel features of illustrative embodiments of the present invention will be more readily appreciated from the following detailed description when read in conjunction with the appended drawings, in which:

FIGS. 6A and 6B show multiple views of a metering sub-system of an illustrative embodiment of a patch pump in accordance with the present invention, in a starting position;

FIGS. 7A and 7B show multiple views of a metering sub-system of an illustrative embodiment of a patch pump in accordance with the present invention, during an intake stroke;

FIGS. 9A and 9B show multiple views of a metering sub-system of an illustrative embodiment of a patch pump in accordance with the present invention, in an intake travel stop position;

FIGS. 11A, 11B and 11C show multiple views of a metering sub-system of an illustrative embodiment of a patch pump in accordance with the present invention, during a valve state change after a discharge stroke;

FIGS. 12A and 12B show multiple views of a metering sub-system of an illustrative embodiment of a patch pump in accordance with the present invention, after a pump cycle is complete;

FIGS. 24A and 24B show multiple views of a metering sub-system of an illustrative embodiment of a patch pump in accordance with the present invention, during a discharge stroke;

FIGS. 25A, 25B and 25C show multiple views of a metering sub-system of an illustrative embodiment of a patch pump in accordance with the present invention, during a valve state change after a discharge stroke;

FIGS. 27A and 27B show multiple views of a metering sub-system of an illustrative embodiment of a patch pump in accordance with the present invention, during an intake stroke;

FIGS. 29A and 29B show multiple views of a metering sub-system of an illustrative embodiment of a patch pump in accordance with the present invention, in an intake rotational stop position;

FIGS. 30A, 30B and 30C show multiple views of a metering sub-system of an illustrative embodiment of a patch pump in accordance with the present invention, after a pump cycle is complete;

FIGS. 34A, 34B, 34C, 34D and 34E show an assembly of a sleeve into a manifold of an illustrative embodiment of a patch pump in accordance with the present invention;

FIGS. 36A, 36B and 36C show multiple cross sections of a valve state change of an illustrative embodiment of a patch pump in accordance with the present invention taken as the sleeve rotates;

FIGS. 37A, 37B, 37C and 37D show a sleeve rotational limit switch of an illustrative embodiment of a patch pump in accordance with the present invention;

FIGS. 38A and 38B show an exploded view of a pump assembly with elastomeric port and piston seals overmolded onto a manifold and pump piston respectively of an illustrative embodiment of a patch pump in accordance with the present invention;

FIGS. 39A, 39B, 39C and 39D show an exploded view of a pump assembly with an alternative rotational limit switch design of an illustrative embodiment of a patch pump in accordance with the present invention;

FIGS. 62 through 67 illustrate different perspective views of an improved pump plug;

Throughout the drawings, like reference numbers should be understood to refer to like elements, features and structures.

DETAILED DESCRIPTION OF THE ILLUSTRATIVE EMBODIMENTS

Figure 1:
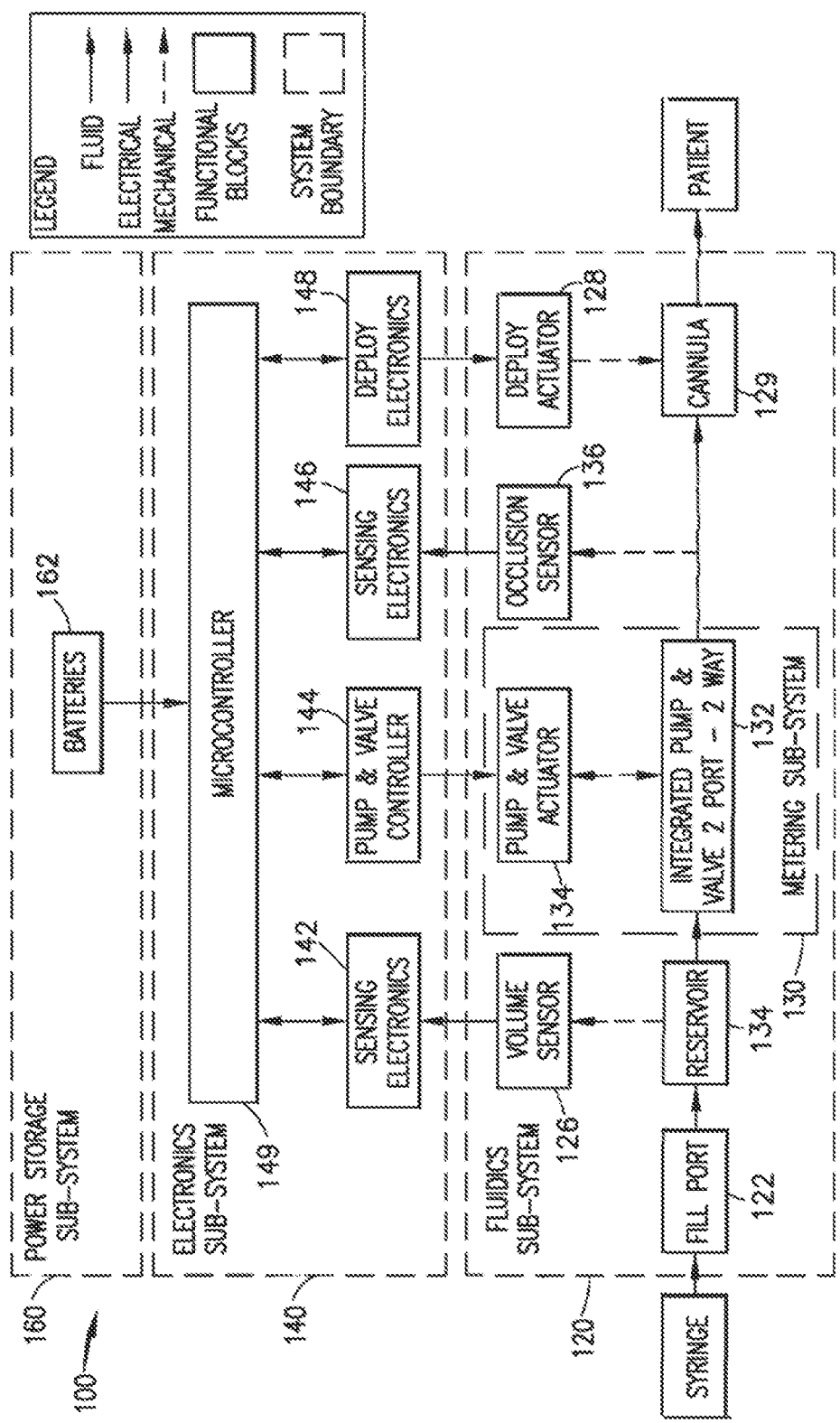
FIG. 1 shows a diagram of an architecture of an illustrative embodiment of a patch pump in accordance with the present invention.

As will be appreciated by one skilled in the art, there are numerous ways of carrying out the examples, improvements, and arrangements of a metering system in accordance with embodiments of the present invention disclosed herein. Although reference will be made to the illustrative embodiments depicted in the drawings and the following descriptions, the embodiments disclosed herein are not meant to be exhaustive of the various alternative designs and embodiments that are encompassed by the disclosed invention, and those skilled in the art will readily appreciate that various modifications may be made, and various combinations can be made, without departing from the invention.

Although various persons, including, but not limited to, a patient or a healthcare professional, can operate or use illustrative embodiments of the present invention, for brevity an operator or user will be referred to as a "user" hereinafter.

Although various fluids can be employed in illustrative embodiments of the present invention, for brevity the liquid in an injection device will be referred to as "fluid" hereinafter.

Illustrative embodiments in accordance with the present invention are depicted in FIGS. 1-30. In an illustrative embodiment according to the present invention, a metering system is provided for use in a wearable insulin infusion patch. For example, in illustrative embodiments of the present invention, the metering system is part of a larger fluidics sub-system that includes a flexible reservoir for storing insulin and a cannula assembly for delivering the insulin into sub-cutaneous tissue. The metering system draws a small dose of fluid from the reservoir and then pushes it down the cannula line and into the patient. The fluid dose is small relative to the reservoir volume, such that many pump strokes are required to completely empty the reservoir.

FIG. 1 shows a diagram of an architecture of a patch pump 100 in accordance with an exemplary embodiment of the present invention. The patch pump 100 includes a fluidics sub-system 120, an electronics sub-system 140 and a power storage sub-system 160.

The fluidics sub-system 120 includes a fill port 122 in fluid communication with a reservoir 124. The reservoir 124 is adapted to receive fluid from a syringe, through the fill port.

The fluidics sub-system 120 further includes a volume sensor 126 mechanically coupled to the reservoir 124. The volume sensor 126 is adapted to detect or determine the fluidic volume of the reservoir.

The fluidics sub-system 120 further includes a metering subsystem 130, which includes an integrated pump and valve system 132 mechanically coupled to a pump and valve actuator 134. The integrated pump and valve system 132 is in fluid communication with the reservoir 124 of the fluidics sub-system 120, and is actuated by the pump and valve actuator 134.

The fluidics sub-system 120 further includes a cannula mechanism having a deployment actuator 128 mechanically coupled to a cannula 129. The deployment actuator 128 is adapted to insert the cannula 129 into a user. The cannula 129 is in fluid communication with the integrated pump and valve system 132 of the metering sub-system 130.

The fluidics sub-system 120 further includes an occlusion sensor 136 mechanically coupled to a fluid pathway between the cannula 129 and the integrated pump and valve system 132. The occlusion sensor 136 is adapted to detect or determine an occlusion in the pathway between the cannula 129 and the integrated pump and valve system 132.

The electronics sub-system 140 includes volume sensing electronics 142 electrically coupled to the volume sensor 126 of the fluidics sub-system 120, a pump and valve controller 144 electrically coupled to the pump and valve actuator 134 of the metering sub-system 130, occlusion sensing electronics 146 electrically coupled to the occlusion sensor 136 of the fluidics sub-system 120, and optional deployment electronics 148 electrically coupled to the cannula 129 of the fluidics subsystem. The electronics sub-system 140 further includes a microcontroller 149 electrically coupled to the volume sensing electronics 142, the pump and valve controller 144, the occlusion sensing electronics 146, and the deployment electronics 148.

The power storage sub-system 160 includes batteries 162 or any other electrical power source known in the art. The batteries 162 can be adapted to power any element or electronic component of the patch pump 100.

Figure 2:
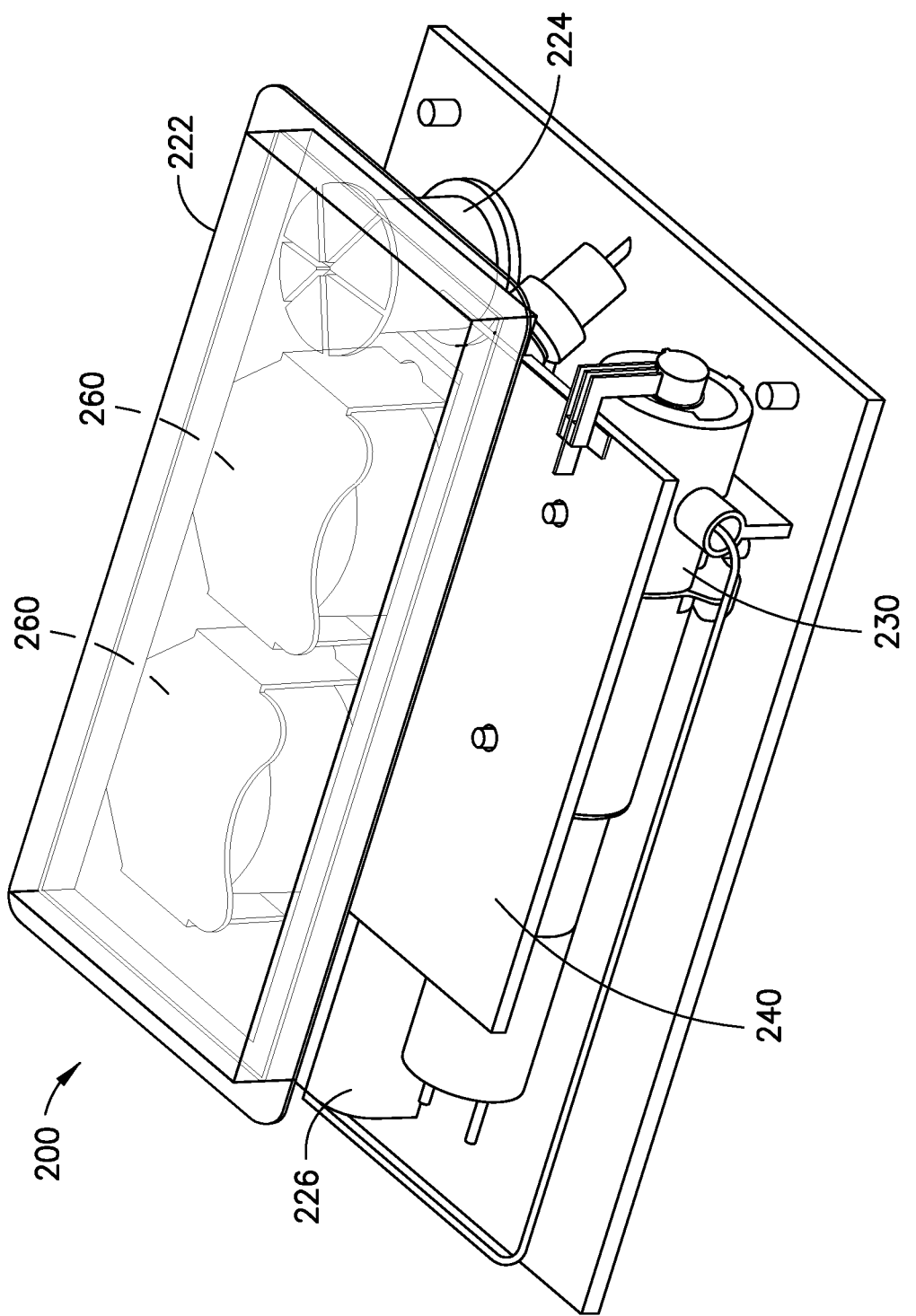
FIG. 2 shows the layout of fluidic and metering system components of an illustrative embodiment of a patch pump in accordance with the present invention.

FIG. 2 shows the layout of fluidic and metering system components of a patch pump 200 in accordance with an exemplary embodiment of the present invention. The patch pump 200 includes a metering sub-system 230, control electronics 240, batteries 260, a reservoir 222, a fill port 224 and a cannula mechanism 226. The elements of patch pump 200 are substantially similar to and interact substantially similarly to the elements of illustrative patch pump 100 that are referred to by similar reference numbers.

Figure 3:
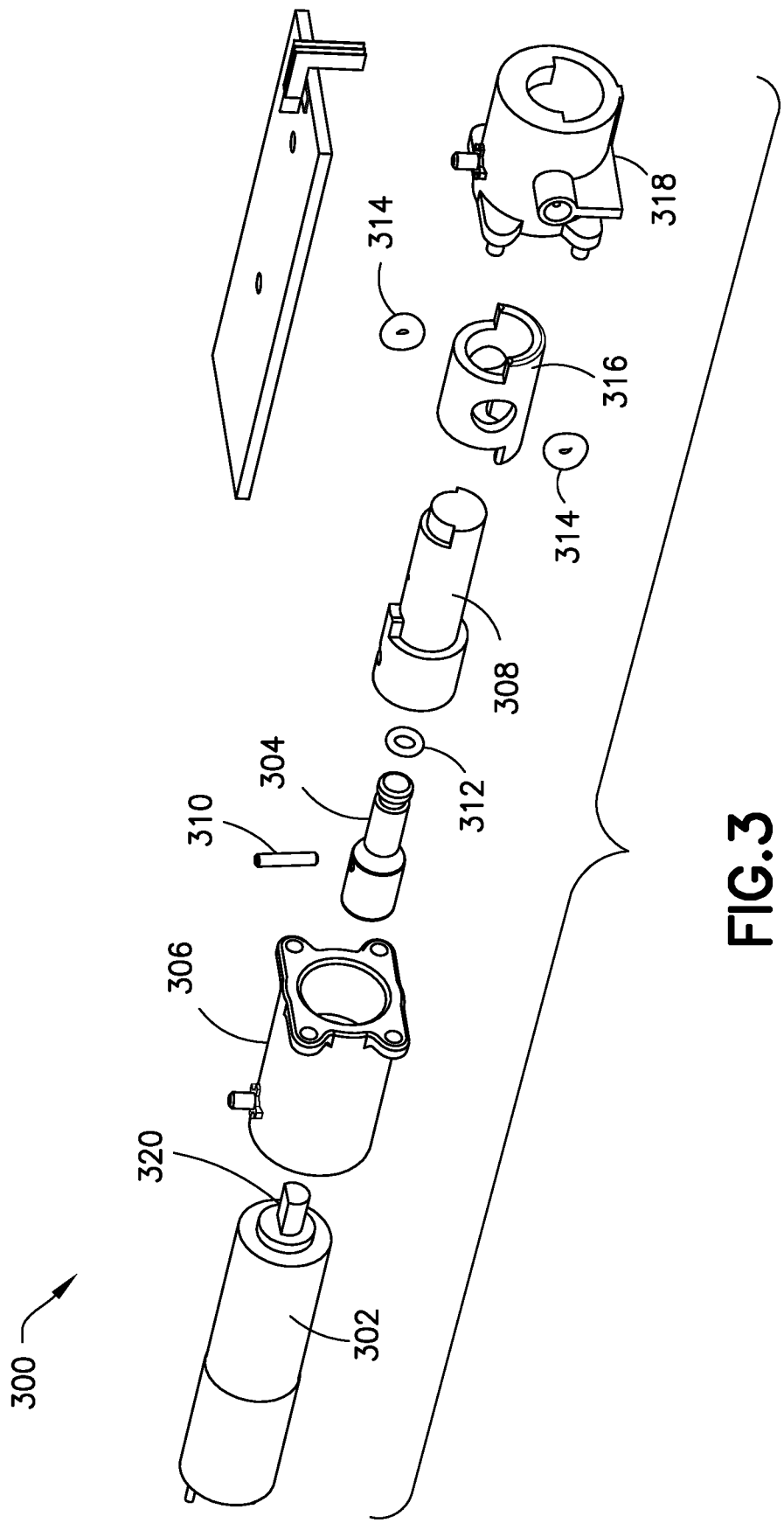
FIG. 3 shows a schematic exploded view of a metering sub-system of an illustrative embodiment of a patch pump in accordance with the present invention.

FIG. 3 is an exploded view of a metering sub-system 300 of a patch pump in accordance with an exemplary embodiment of the present invention. The metering sub-system 300 includes a DC gear motor 302 mechanically coupled to a pump piston 304 disposed within a pump casing 306. The pump piston 304 is mechanically coupled to a pump housing 308 by a coupling pin 310. The metering sub-system 300 further includes a pump seal 312 between the pump piston 304 and the pump housing 308. The metering sub-system 300 further includes port seals 314 on a seal carriage 316 disposed within a valve housing 318.

In an exemplary embodiment of the present invention, the output shaft 320 of the DC gear motor can rotate 360° in either direction. The pump piston 304 can rotate 360° in either direction and can translate by about 0.050 inches. The pump housing 308 can rotate 180° in either direction. The pump casing 306, the port seals 314, the seal carriage 316 and the valve housing 318 are preferably stationary.

The metering sub-system 300 includes a positive displacement pump with integrated flow control valve & mechanical actuator and drive system. The pump includes a piston 304 and rotationally actuated selector valve. The metering system pulls a precise volume of insulin from a flexible reservoir into a pump volume 320 formed between the piston 304 and the pump housing 308 (see FIG. 5), and then expels this insulin volume through a cannula into a patient's subcutaneous tissue, administering insulin in small, discrete doses. The pump stroke creates positive and negative pressure gradients within the fluid path to induce flow. The stroke and internal diameter of the pump volume determine the nominal size and accuracy of the dose. The fluid control valve is actively shuttled between the reservoir and cannula fluid ports at each end of the pump stroke to alternately block and open the ports to ensure that fluid flow is unidirectional (from the reservoir to the patient) and that there is no possibility of free flow between the reservoir and the patient.

Figure 4:
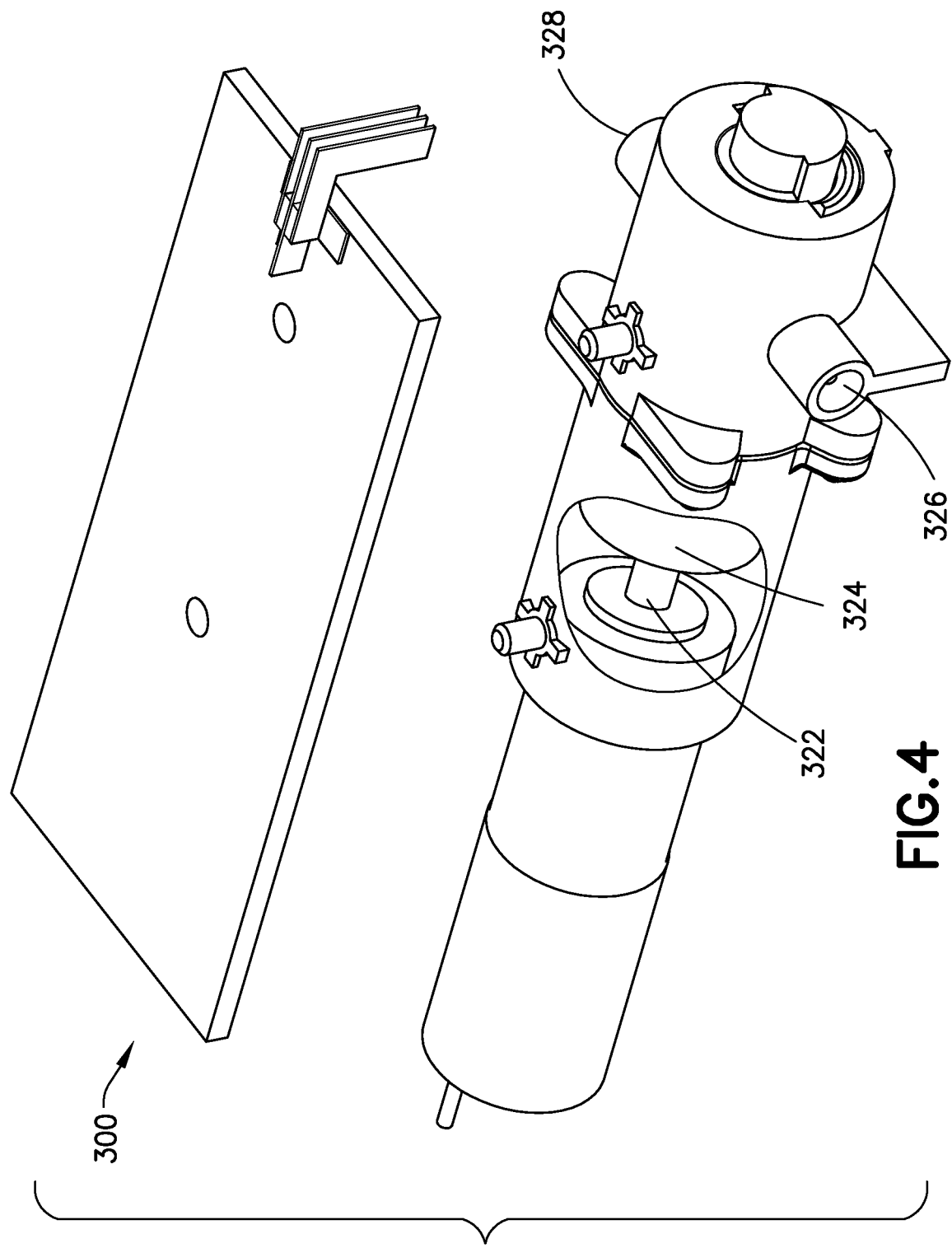
FIG. 4 shows the layout of a metering sub-system of an illustrative embodiment of a patch pump in accordance with the present invention.

FIG. 4 is an assembly view of the metering sub-system 300 according to an exemplary embodiment of the present invention. Also illustrated are a motor to piston coupling 322, a piston to pump housing coupling 324, a reservoir port 326 and a cannula port 328.

Figure 5:
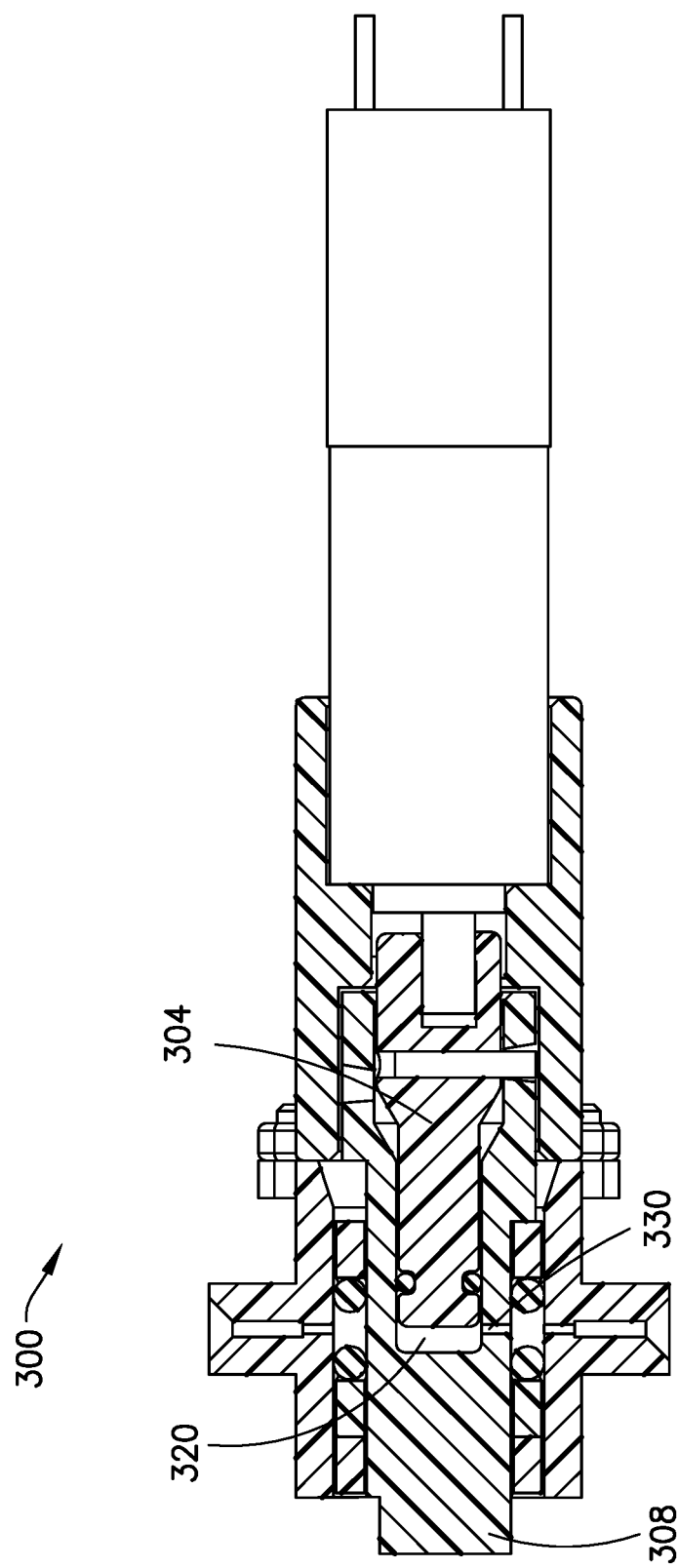
FIG. 5 shows a schematic cross-sectional view of a metering sub-system of an illustrative embodiment of a patch pump in accordance with the present invention.

FIG. 5 is a cross-sectional view of the metering sub-system 300 of an exemplary embodiment of the present invention. As illustrated, a pump volume 320 is formed between the piston and the pump housing 308. The pump housing includes a side port 330 that alternates in orientation between the reservoir port 326 and the cannula port 328 as the motor 302 reciprocates the pump, as will be described in greater detail below.

In operation, an illustrative cycle of a metering system according to the present invention includes 4 steps: a 180° pump intake (counterclockwise) (when viewing from the pump toward the motor); a 180° valve state change (counterclockwise); a 180° pump discharge (clockwise); and a 180° valve state change (clockwise). A complete cycle requires a full rotation (360°) in each direction.

Figure 6B:
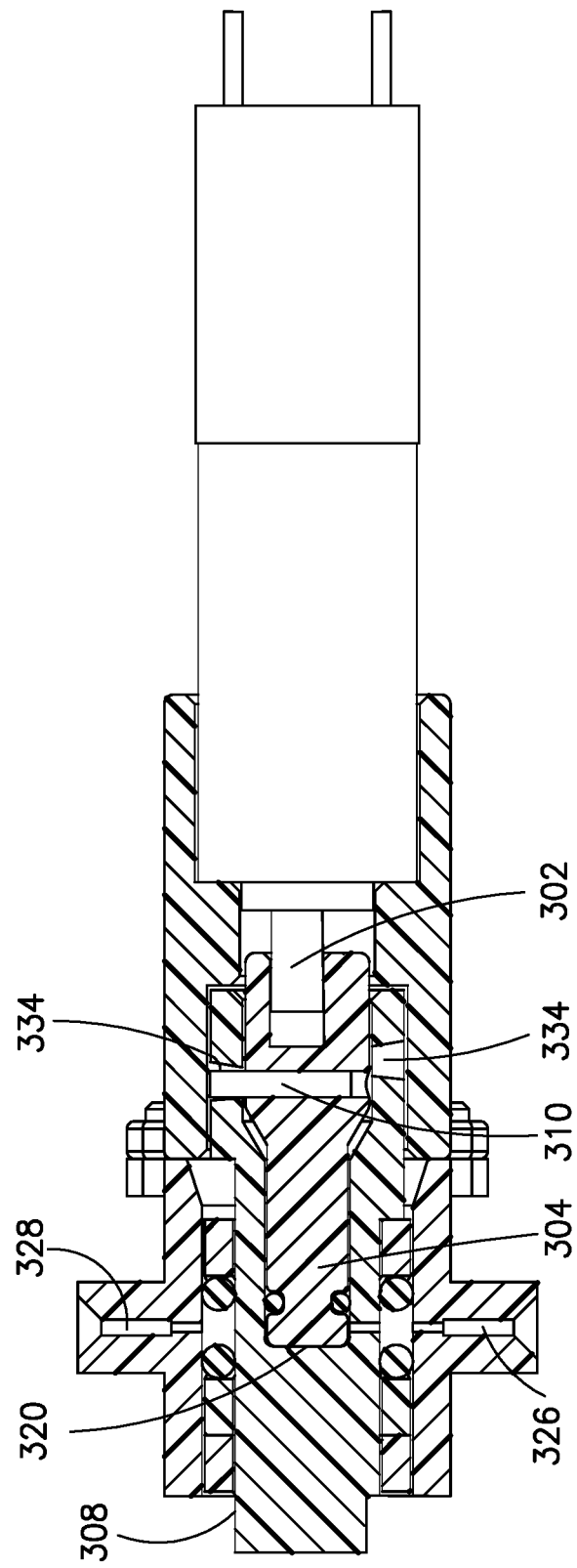

FIG. 6A is an isometric view, and FIG. 6B is a cross-section view of the metering sub-system 300 in a starting position. In the starting position, the pump piston 304 is fully extended, the pump housing blocks the cannula port flow path at the cannula port 328, and the reservoir port 326 is open to the side port 330 of the pump housing 308, and a rotational limit sensor 332 is engaged. Pump housing 308 includes a helical groove 334 which receives coupling pin 310. Piston 304 is in sliding engagement with pump housing 308 such that as piston 304 rotates within pump housing 308 (by rotational force of the motor 302), coupling pin 310 slides along helical groove 334 to force piston 304 to translate axially with reference to pump housing 308. In this embodiment, the helical groove 334 is formed into pump housing 308 and provides for 180° of rotation for coupling pin 310.

Figure 7B:
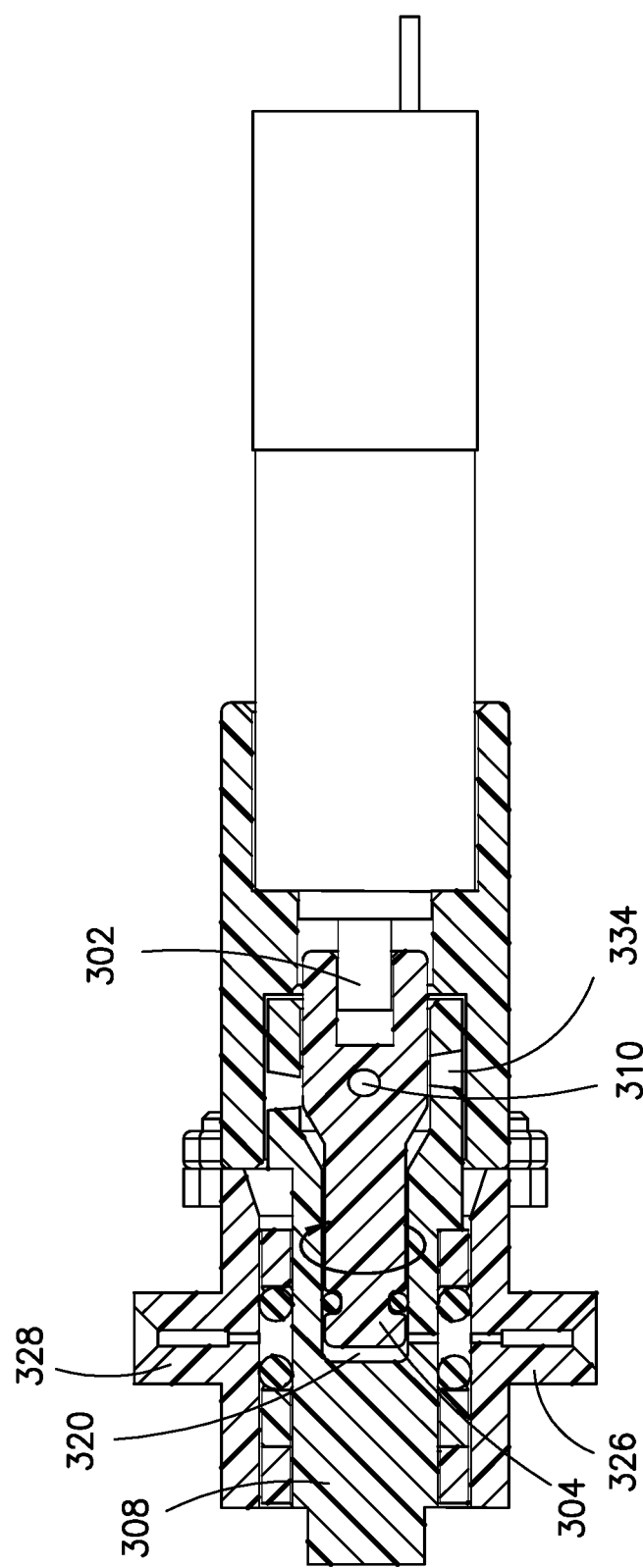

FIG. 7A is an isometric view, and FIG. 7B is a cross-section view of the metering sub-system 300 during an intake stroke. The DC motor 302 turns the pump piston 304, which is driven along the helical groove 334 (rotating and translating) of the pump housing 308 via the coupling pin 310. The pump piston 304 translates toward the DC motor 302, drawing fluid into the increasing pump volume 320. During the intake stroke, friction between the seals and the outside diameter of the pump housing 308 is preferably be high enough to ensure that the pump housing 308 does not rotate. The pump housing 308 is stationary, while the pump volume 320 is expanding. The cannula port 328 is blocked, while the reservoir port 326 is open to fluid flowing into the expanding pump volume 320. There is a sliding engagement between the motor 302 and the pump piston 304.

Figure 8B:
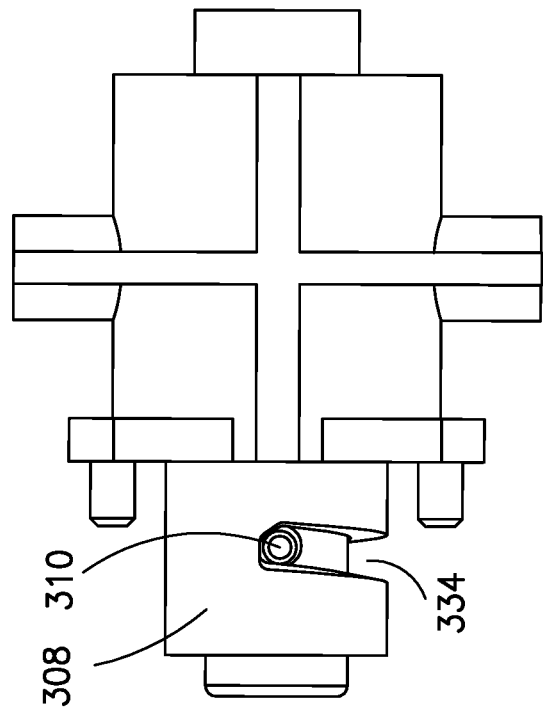
FIGS. 8A, 8B and 8C show multiple views of a metering sub-system of an illustrative embodiment of a patch pump in accordance with the present invention, during a valve state change after an intake stroke.
Figure 8A:
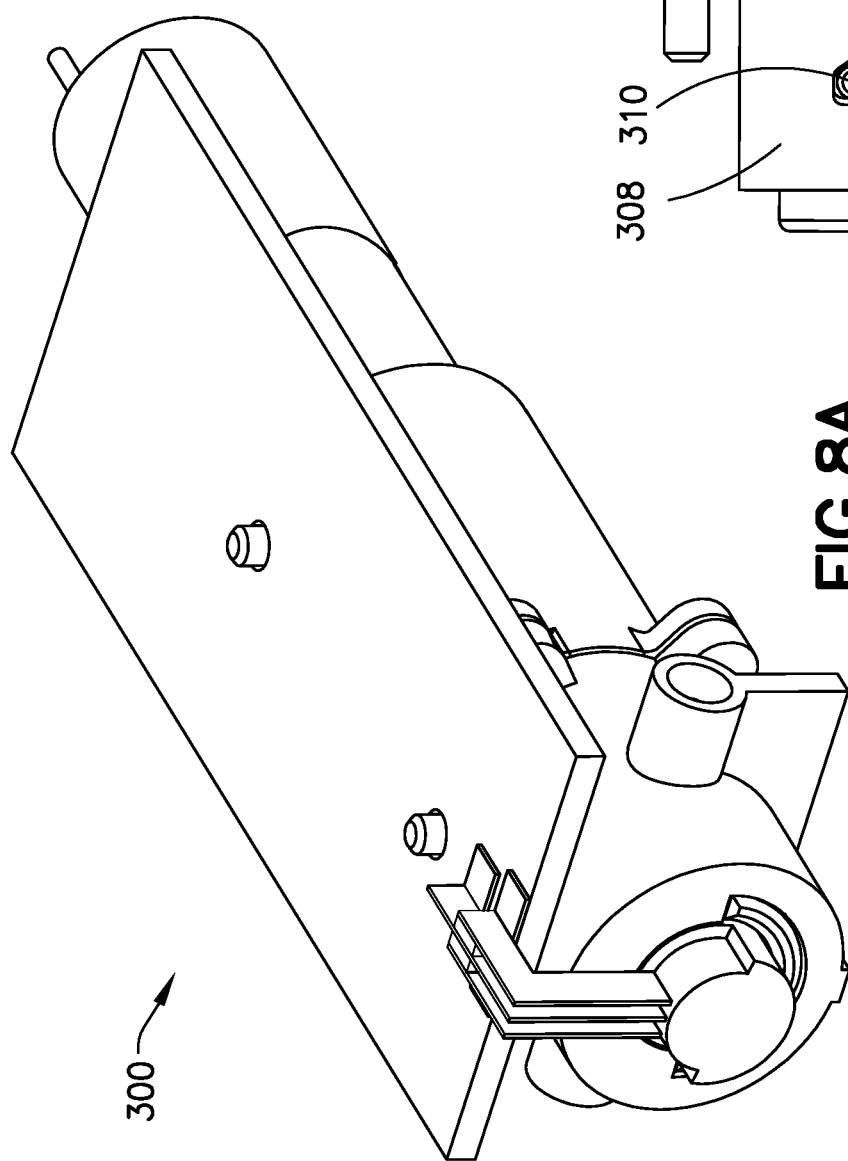
Figure 8C:
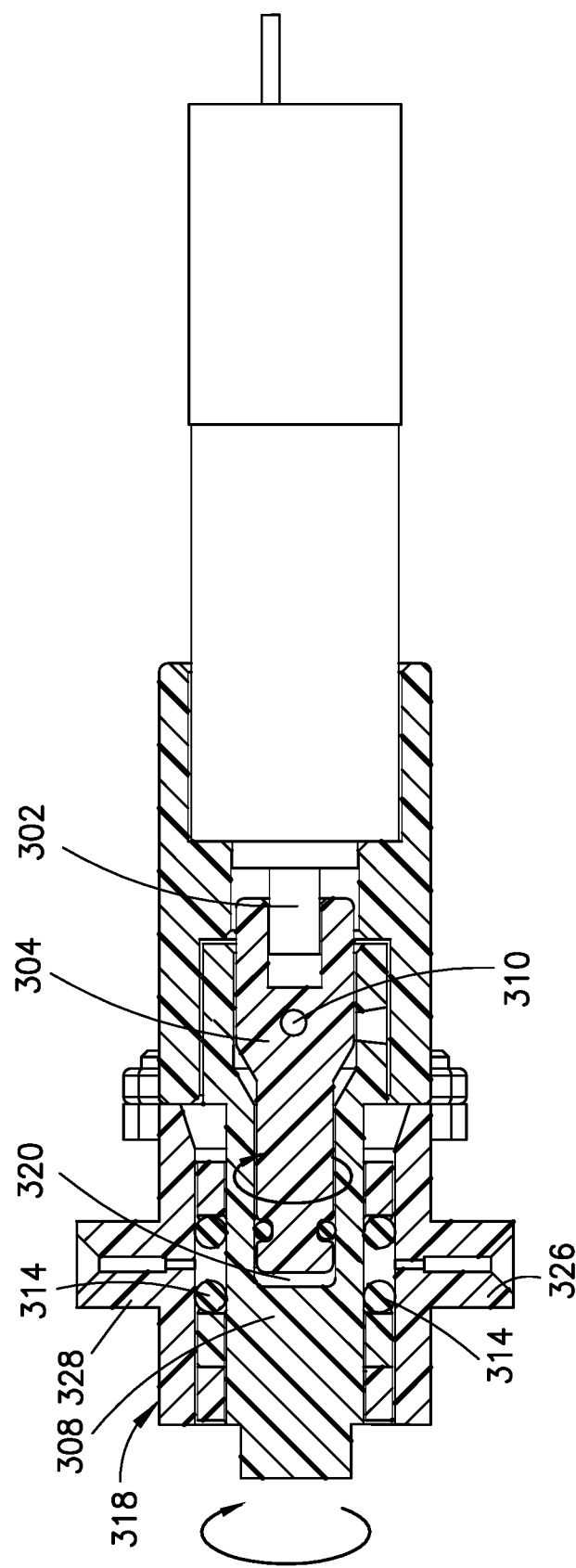

FIG. 8A is an assembly view, FIG. 8B is a detail view, and FIG. 8C is a cross-section view of the patch pump during a valve state change after an intake stroke. Torque is transmitted from the drive shaft of the motor 302, to the pump piston 304, and then to the pump housing 308 via the coupling pin 310. Once the coupling pin 310 rotates to the end of the helical groove 334, further rotation of motor 302 causes the coupling pin 310 to rotate pump housing 308 and pump piston 304 together as a unit without relative axial translation. The side port 330 on the pump housing 308 rotates between the reservoir port 326 and the cannula port 328. Surface tension of the pump housing 308 side port 330 holds the fluid in the pump volume 320. The pump housing side port 330 moves out of alignment with the reservoir port 326 and into alignment with the cannula port 328 over the next 180° rotation of the motor 302. In between, both the cannula port 328 and the reservoir port 326 are blocked. The coupling pin 310 is at the end of the helical groove 334 and transmits torque to the pump housing 308. The coupling pin 310 locks the pump piston 304 and the pump housing 308 together to prevent relative axial motion between the two components. The pump piston 304 and the pump housing 308 therefore rotate as a unit and do not translate relative to each other. The pump housing 308 rotates while the pump volume 320 is fixed and the pump piston 304 rotates. The seals 314, the seal carriage and the valve housing 318 are preferably stationary.

Figure 9B:
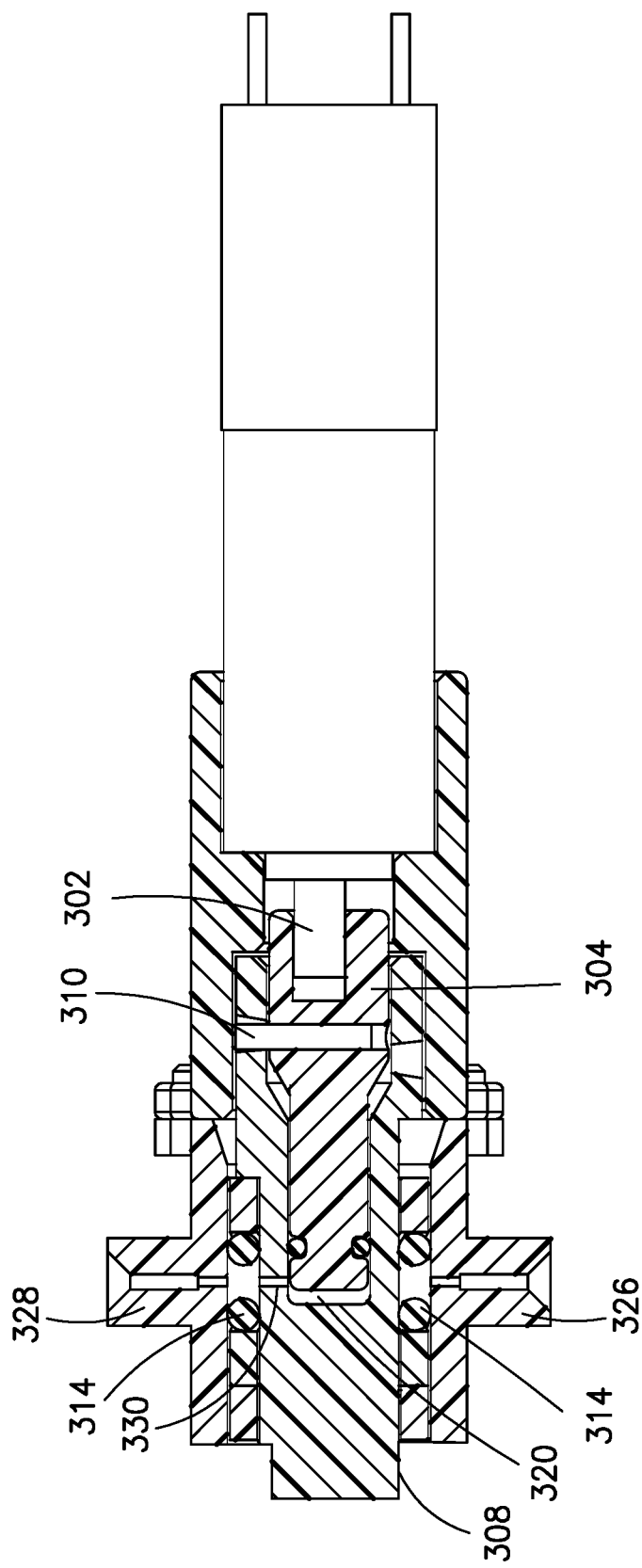

FIG. 9A is an assembly view, and FIG. 9B is a cross-section view of the metering sub-system in an intake travel stop position, ready to infuse. As illustrated, the side port 330 of the pump housing 308 is aligned with the cannula port 328, the pump volume 320 is expanded, and the reservoir port 326 is blocked. The rotational limit sensor 332 is engaged by a feature on the rotating pump housing 308. The motor 302, the pump piston 304, and the pump housing 308 are stationary.

Figure 10A:
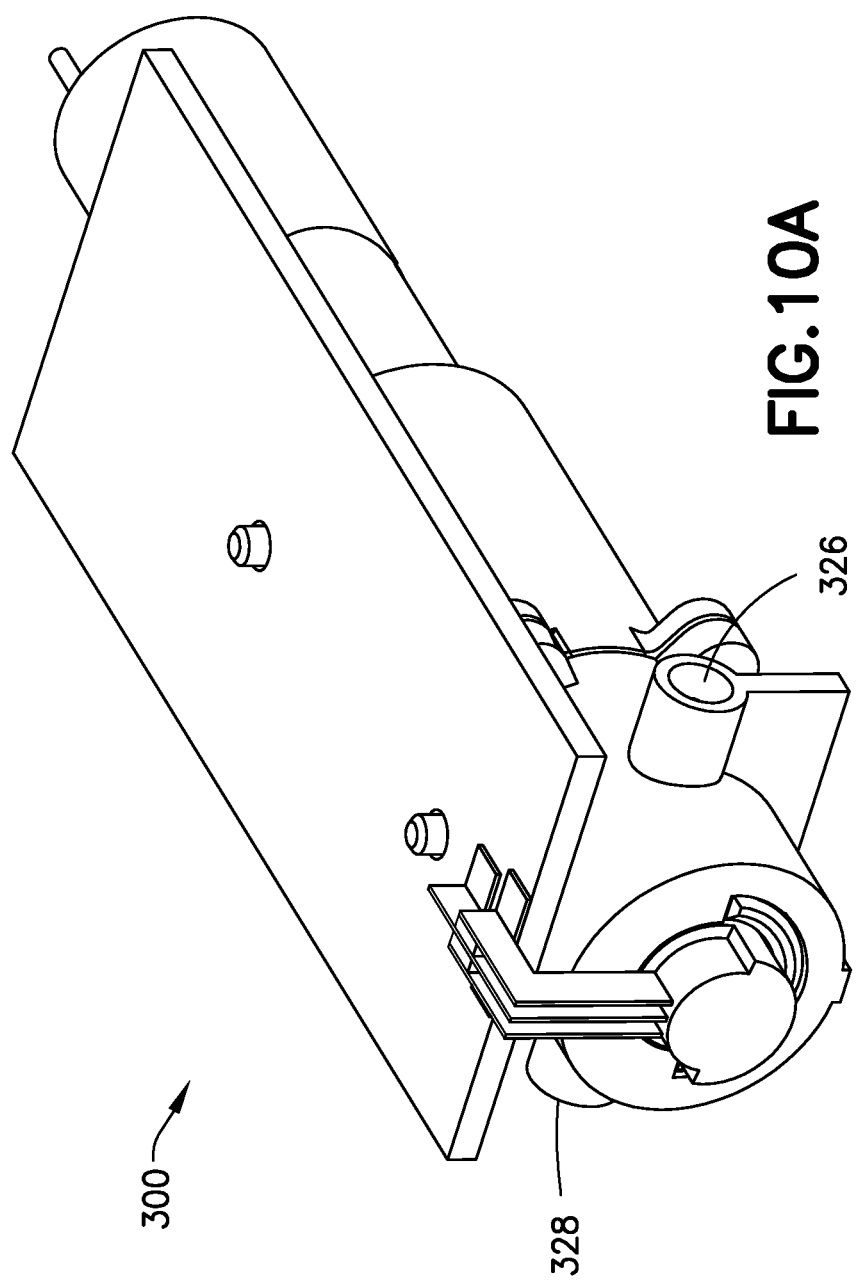
FIGS. 10A and 10B show multiple views of a metering sub-system of an illustrative embodiment of a patch pump in accordance with the present invention, during a discharge stroke.
Figure 10B:
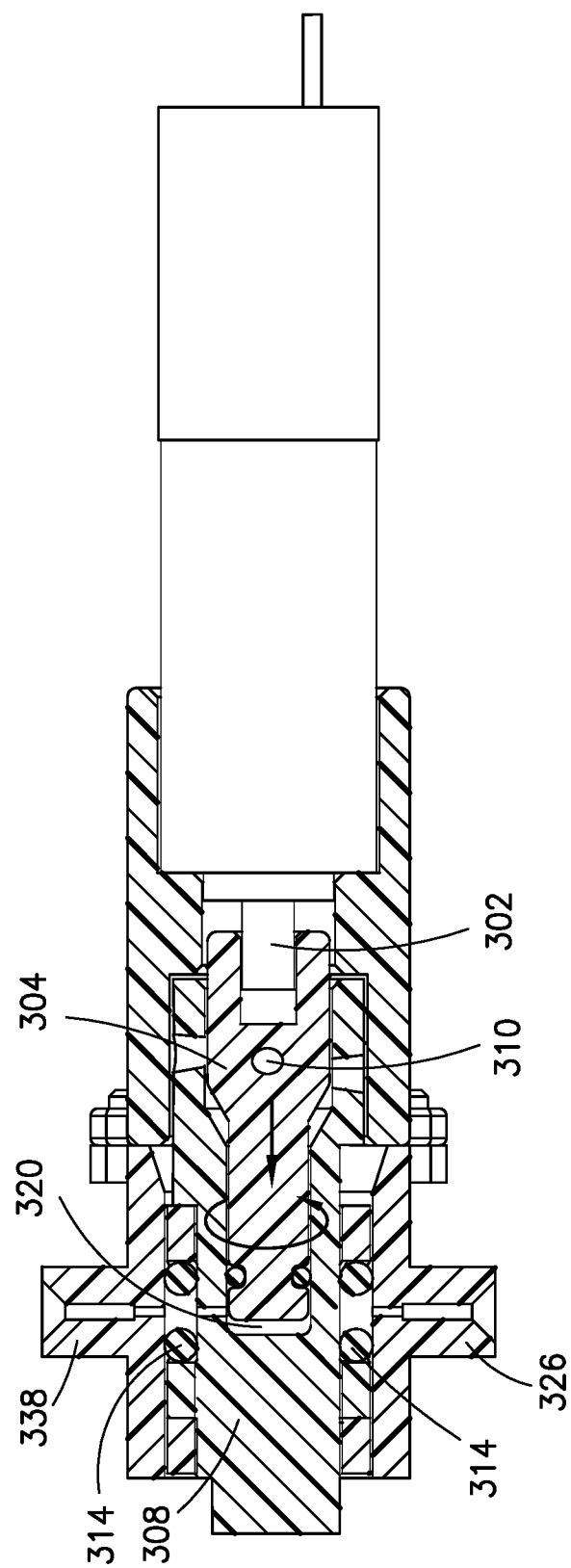

FIG. 10A is an assembly view, and FIG. 10B is a cross-section view of the metering sub-system 300 during a discharge stroke. At the end of the intake stroke the pump housing 308 engages the limit switch 332, which causes the DC motor 302 to switch directions. Accordingly, the motor 302 turns the piston 304 and drives the coupling pin 310 down the helical groove 334 of the pump housing 308, causing the piston 304 to translate axially. The pump piston 304 translates axially away from the DC motor 302, pushing fluid from the pump volume 320 and out of the cannula port 328 to the cannula. During the discharge stroke, friction between the seals 314 and the outside diameter of the pump housing 308 is preferably high enough to ensure that the pump housing 308 does not rotate. The cannula port 328 is open to fluid flowing out of the collapsing pump volume 320. The reservoir port 326 is blocked. The pump housing 308 is stationary while the pump volume 320 is collapsing and the pump piston 304 rotates and translates in a helical motion. The motor is slidingly connected to the piston 304 to accommodate the translation motion of the piston as it rotates in the helical groove 334.

FIG. 11A is an assembly view, FIG. 11B is a detail view, and FIG. 11C is a cross-section view of the metering sub-system 300 during a valve state change after a discharge stroke. Torque is transmitted from the drive shaft of the motor 302, to the pump piston 304, and then to the pump housing 308 via the coupling pin 310. The pump housing 308 and pump piston 304 rotate as a unit with no relative axial motion. The side port 330 on the pump housing 308 rotates between the reservoir port 326 and the cannula port 328, both of which are blocked during the rotation. Surface tension of the pump housing 308 side port 330 holds the fluid in the pump volume 320. The coupling pin 310 locks the pump piston 304 and the pump housing 308 together to prevent relative axial motion between the two components. Therefore, the pump piston 304 and the pump housing 308 rotate as a unit and do not translate relative to each other. The pump housing 308 rotates while the pump volume 320 is fixed. The seals 314, the seal carriage and the valve housing 318 are preferably stationary.

Figure 12A:
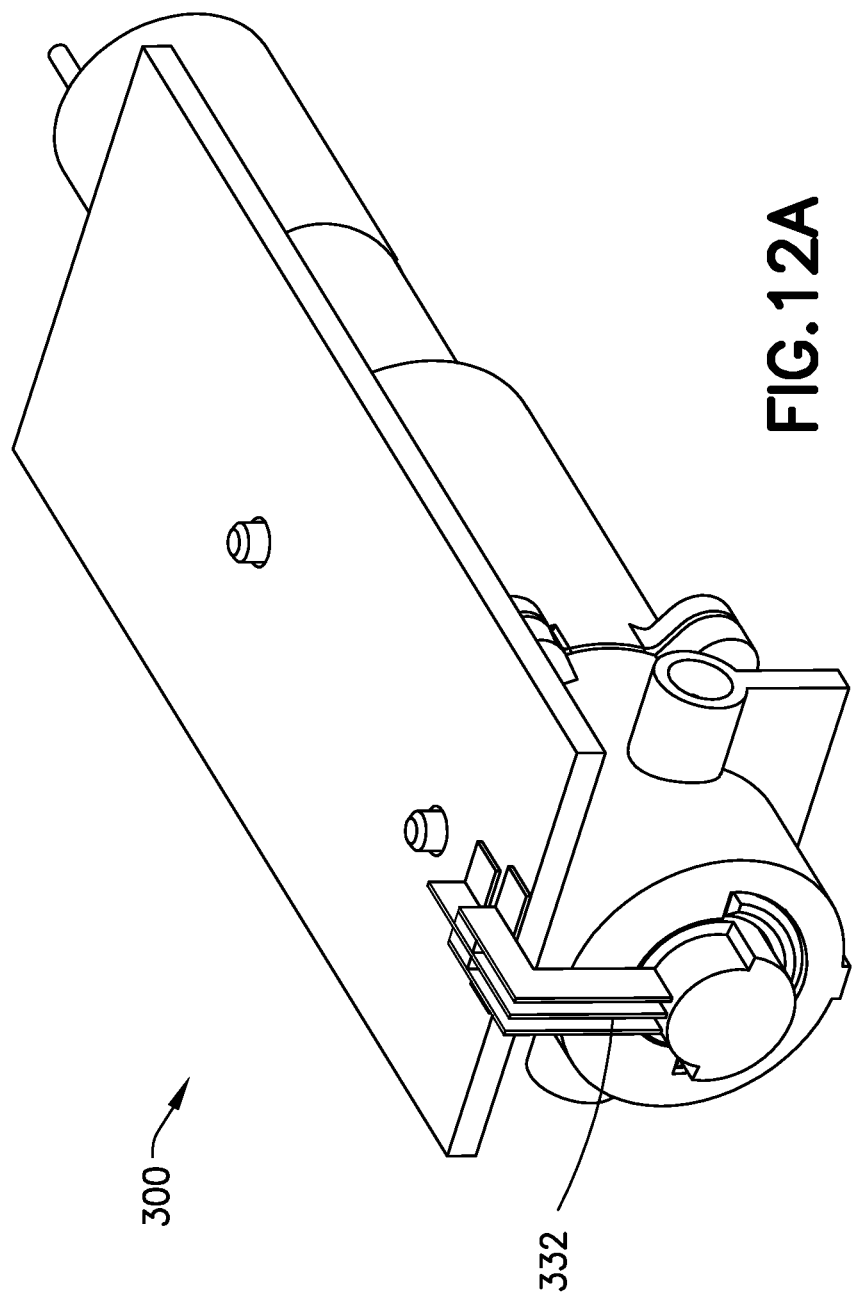

FIG. 12A is an assembly view, and FIG. 12B is a cross-section view of the metering sub-system 300 after a pump cycle is complete. The pump mechanism (piston 304) is fully extended, completing the pump cycle. The rotational limit sensor 332 is engaged to reverse the motor 302 and begin the pump cycle again. The cannula port 328 is blocked, while the reservoir port 326 is open to the flow path from the reservoir.

In the foregoing exemplary embodiment, the pump piston both rotates and translates, the pump housing rotates, and the valve housing is stationary. However, it should be appreciated that in other embodiments, the system may be configured so that the pump piston rotates, the pump housing both rotates and translates, and the valve housing translates, or any other combination of motions causing the pump volume to increase and decrease, and a port in communication with the pump volume to move from alignment with the reservoir port to alignment with the cannula port.

In the foregoing exemplary embodiment, the pump stroke and valve state change are configured with 180° rotational actuation from the motor. However, it should be appreciated that any suitable angle may be selected for the segments of the pump cycle.

In the foregoing exemplary embodiment, there is an atmospheric break between the cannula and reservoir ports during the valve state change. However, it should be appreciated that in other embodiments, the seals may be configured, or additional seals may be added, to eliminate the atmospheric break and seal the pump and valve system during the state change.

In the foregoing exemplary embodiment, a DC gear motor is used to drive the pump and valve. However, in other embodiments, any suitable drive mechanism may be provided to drive the pump and valve. For example, solenoids, nitinol wire, voice coil actuators, piezo motors, wax motors, and/or any other type of motor known in the art can be used to drive the pump.

In the foregoing exemplary embodiment, the pump uses full discharge strokes. However, it should be appreciated that in other embodiments, a system with sequential incremental discharge strokes may be used to dispense finer doses.

In the foregoing exemplary embodiment, the pump uses on/off limit switches to determine the state of the system at the limits of rotational travel. However, it should be appreciated that in other embodiments, other sensors with the capability to determine intermediate states, such as an encoder wheel and optical sensor, may be used to improve the resolution of the sensing scheme.

It should be appreciated that the internal diameter of the pump may be adjusted to change the nominal output per cycle.

In the foregoing exemplary embodiment, the pump uses elastomeric O-ring seals. However, it should be appreciated that other arrangements may also be used. For example, fluid seals may be molded directly onto the seal carriage, other elastomeric seals such as quad rings could be used, or other seal materials such as Teflon or polyethylene lip seals are used.

In alternate embodiments of the invention, the motion of the pump can be used to initiate or trigger the deployment of the cannula.

In the foregoing exemplary, the system advantageously uses a bi-directional actuation. The motor rotation is reversed to alternate between intake and discharge strokes. This provides a safety feature that prevents runaway in the event of a malfunctioning motor. The motor must reciprocate in order for the pump to continue delivering medication from the reservoir. However, it should be appreciated that in other embodiments, the metering system is designed to use a unidirectional actuator.

In the foregoing exemplary embodiment, the system uses a pouch reservoir with two flexible walls. However, in other embodiments, the reservoir can be formed in any suitable manner, including with one rigid and one flexible wall.

Figure 13:
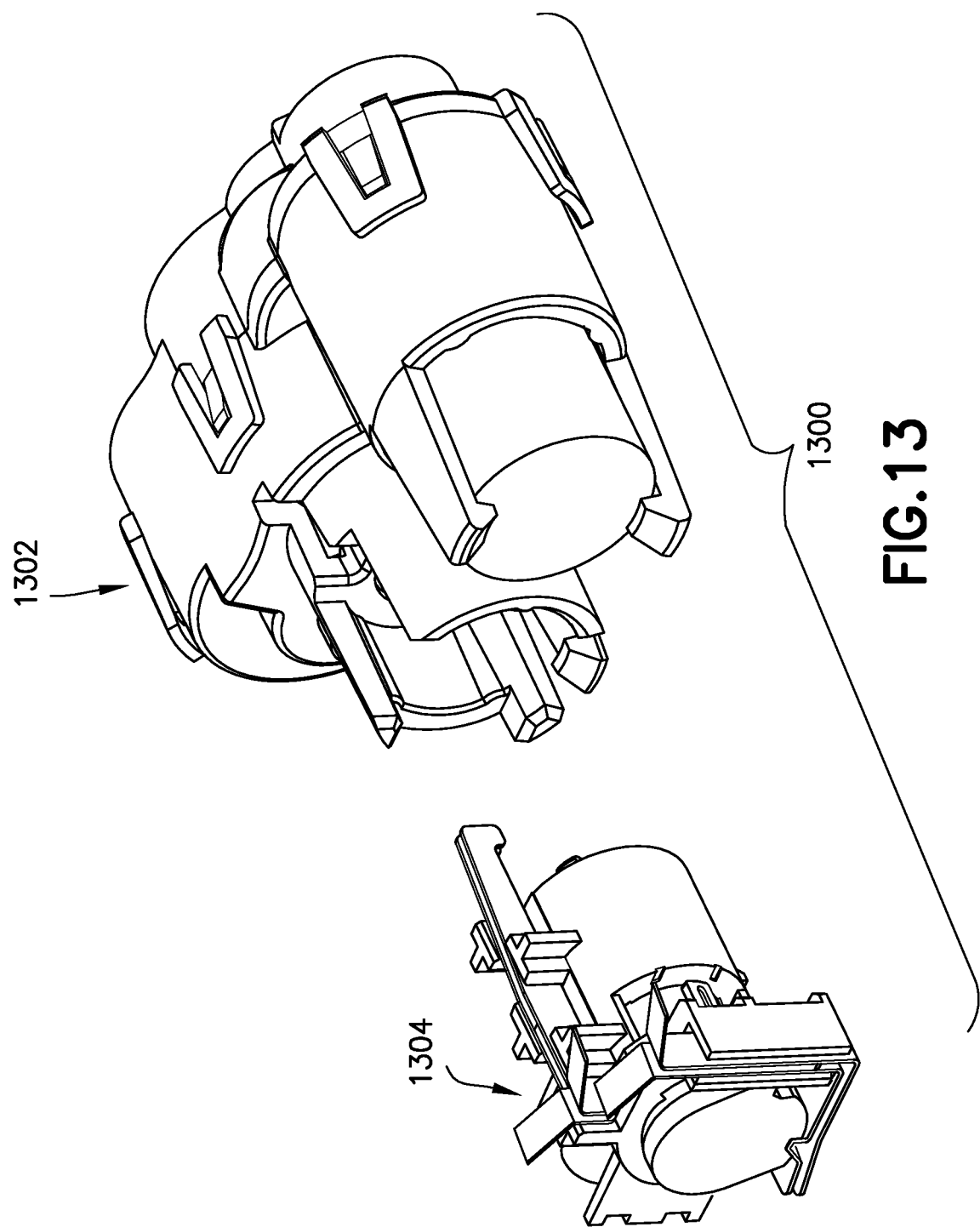
FIG. 13 shows an exploded view of a metering sub-system of an illustrative embodiment of a patch pump in accordance with the present invention.

FIG. 13 is an exploded view of a metering sub-system 1300 for a patch pump in accordance another illustrative embodiment of the present invention. The metering sub-system 1300 includes a motor and gearbox assembly 1302 and a pump assembly 1304.

Figure 14:
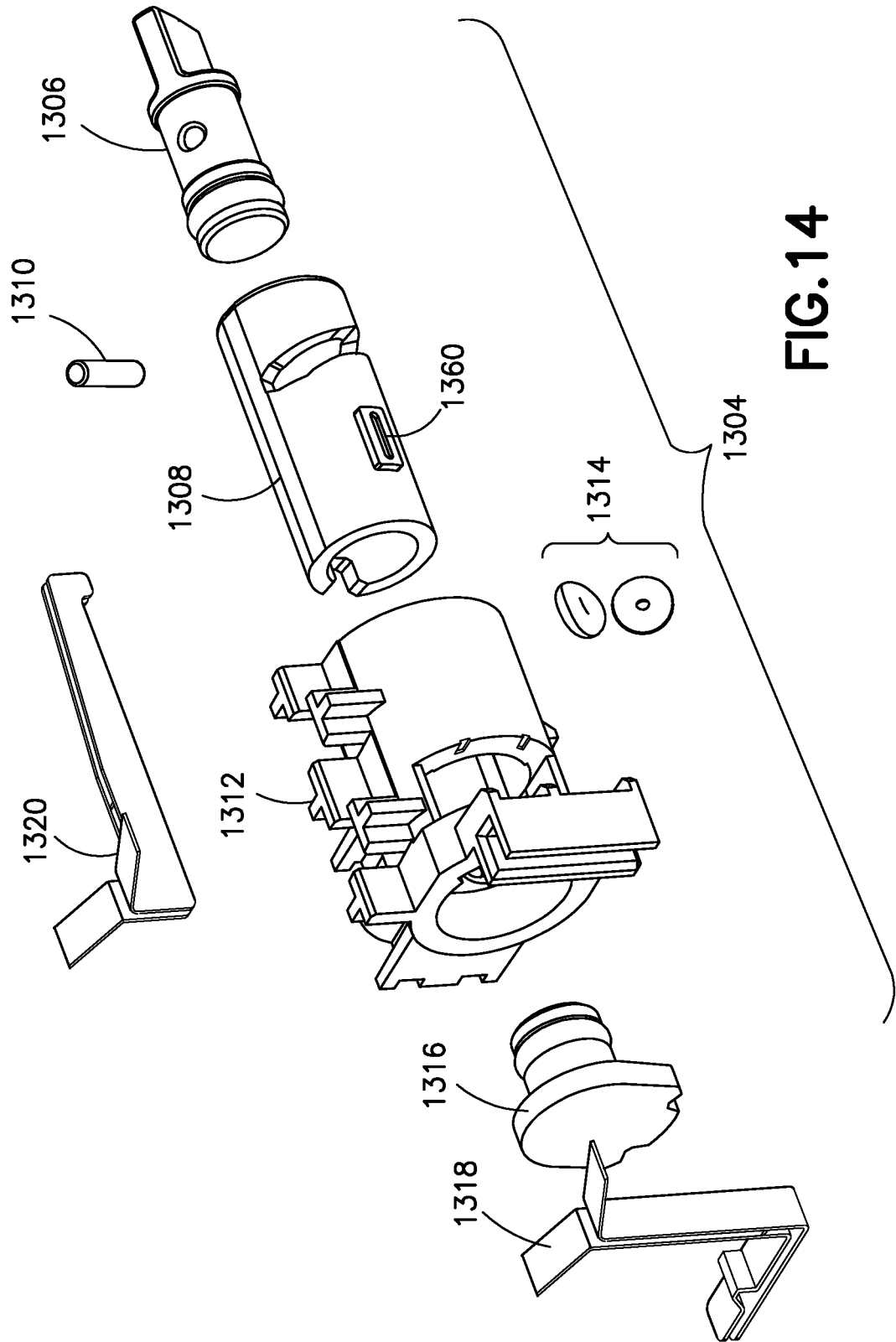
FIG. 14 shows a schematic exploded view of a pump assembly of an illustrative embodiment of a metering pump in accordance with the present invention.

FIG. 14 is an exploded view of the pump assembly 1304. The pump assembly 1304 includes a piston 1306 mechanically coupled to a sleeve 1308 through a coupling pin 1310, within a pump manifold 1312. The pump assembly 1304 further includes port seals 1314, a plug 1316, a sleeve rotational limit switch 1318 and an output gear rotational limit switch 1320.

The piston 1306 rotates a total of 196° in either direction and can translate by about 0.038 inches. The sleeve 1308 and the plug 1316 rotate together (as a pair) 56° in either direction. The pump manifold 1312 and the port seals 1314 are stationary.

Figure 15:
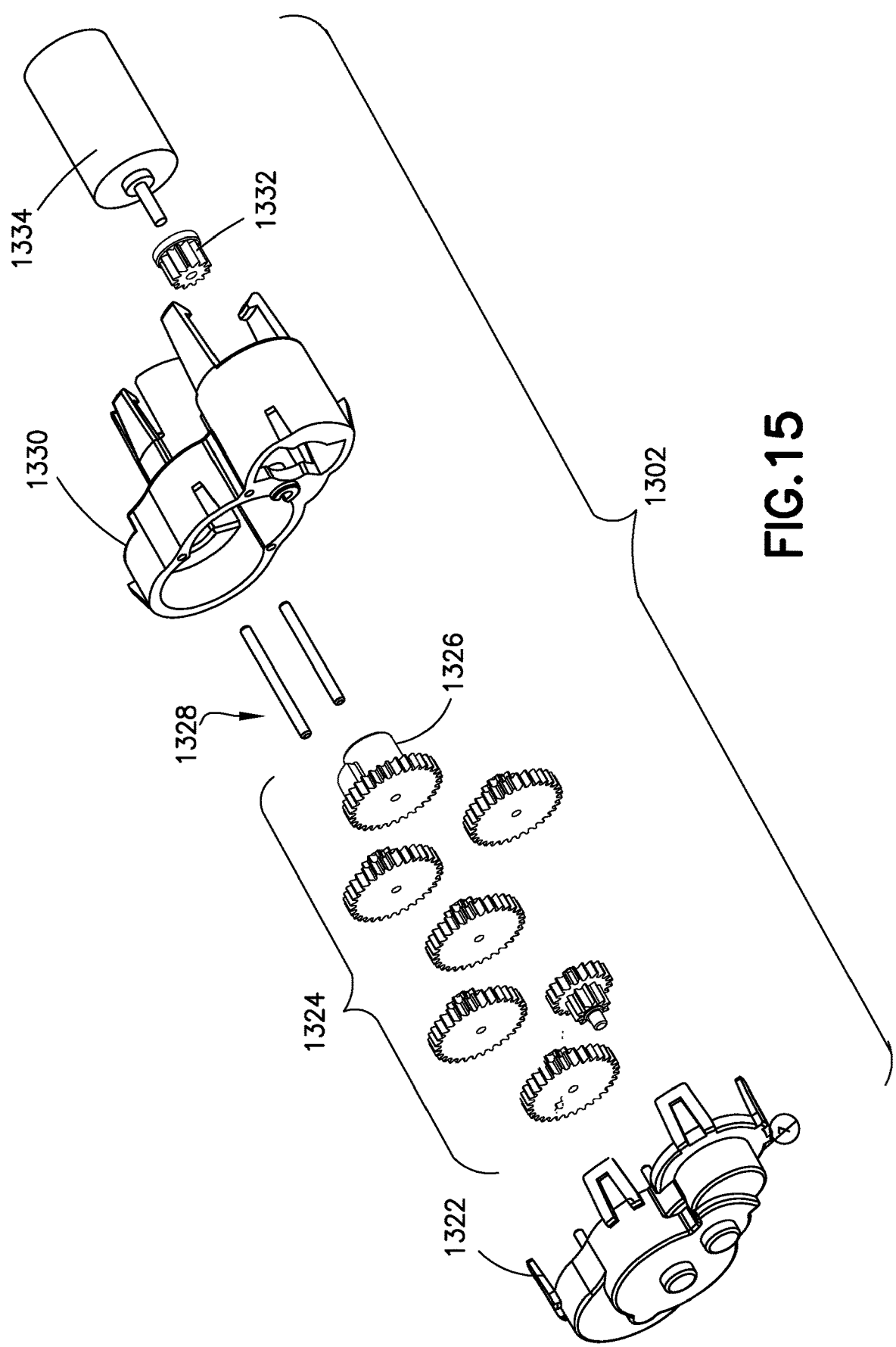
FIG. 15 shows a schematic exploded view of a motor and gearbox assembly of an illustrative embodiment of a metering pump in accordance with the present invention.

FIG. 15 is an exploded view of the motor and gearbox assembly 1302. The motor and gearbox assembly 1302 includes a gearbox cover 1322, compound gears 1324, an output gear 1326, axles 1328, a gearbox base 1330, a motor pinion gear 1332 and a DC motor 1334.

Figure 16A:
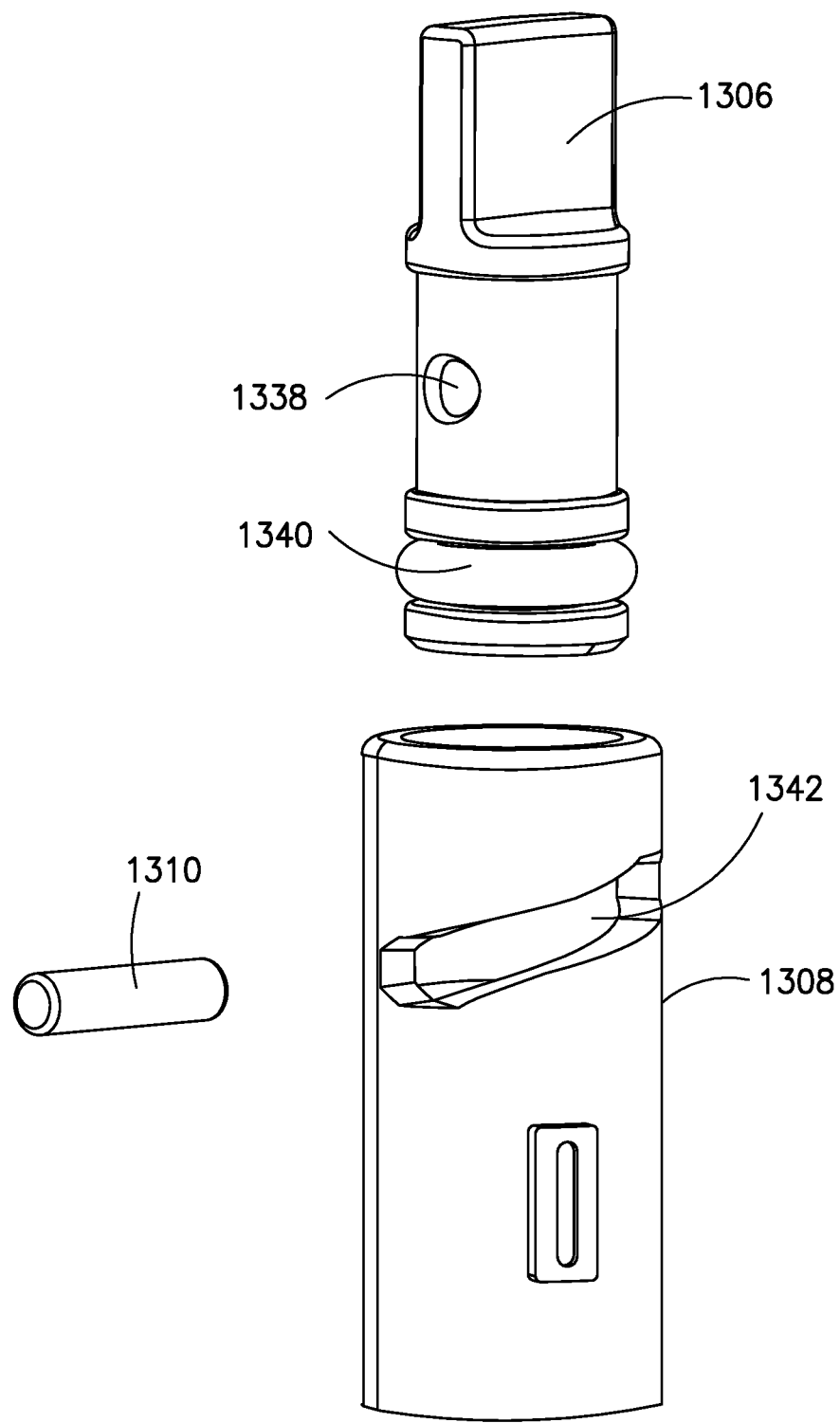
FIGS. 16A, 16B, 16C and 16D show multiple schematic views illustrating a method of assembly of a piston into a sleeve in accordance with the present invention.
Figure 16B:
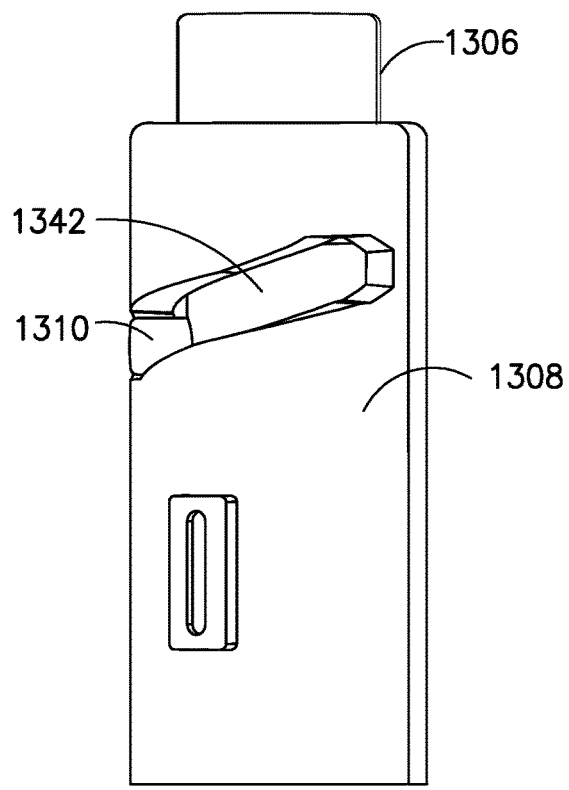
Figure 16C:
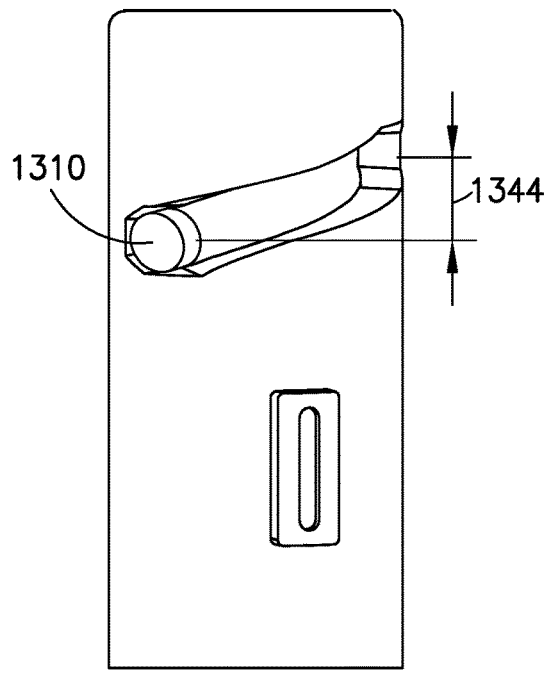
Figure 16D:
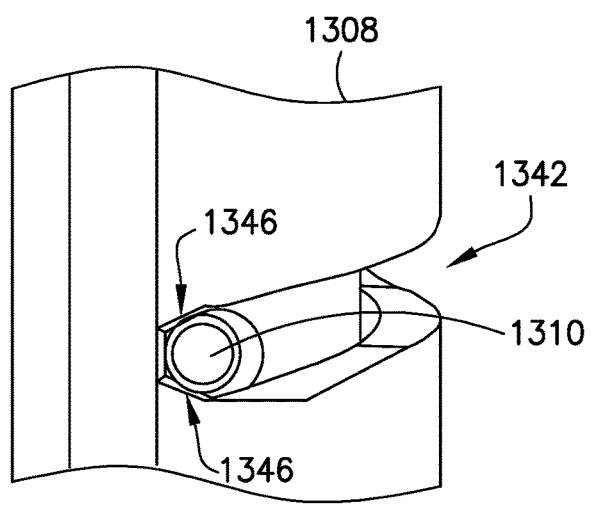

FIGS. 16A-16D illustrate the assembly and operation of the piston 1306, sleeve 1308 and coupling pin 1310. FIG. 16A illustrates the piston 1306, which includes a press fit hole 1338 which receives the coupling pin 1310, as well as a piston seal 1340, which tightly seals the piston within the sleeve 1308. Sleeve 1308 includes a helical groove 1342. Piston 1306 is pressed axially into sleeve 1308, and then coupling pin 1310 is press fit into hole 1338 through the helical groove 1342. This provides operation similar to the above described embodiment, where rotation of the piston 1306 causes axial translation of the piston 1306 relative to the sleeve 1308 due to interaction of the coupling pin 1310 and the helical groove 1342. FIG. 16B illustrates the piston 1306, sleeve 1308 and coupling pin 1310 assembled, with coupling pin 1310 shown at the lower end of helical groove 1342. FIG. 16C illustrates the axial stroke length 1344 of the piston 1306 relative to the sleeve 1308 as a result of the helical groove 1342. FIG. 16D illustrates tapered faces 1346 that are preferably provided at the ends of the helical groove 1342 to center the coupling pin 1310 within the groove 1342.

Figure 17A:
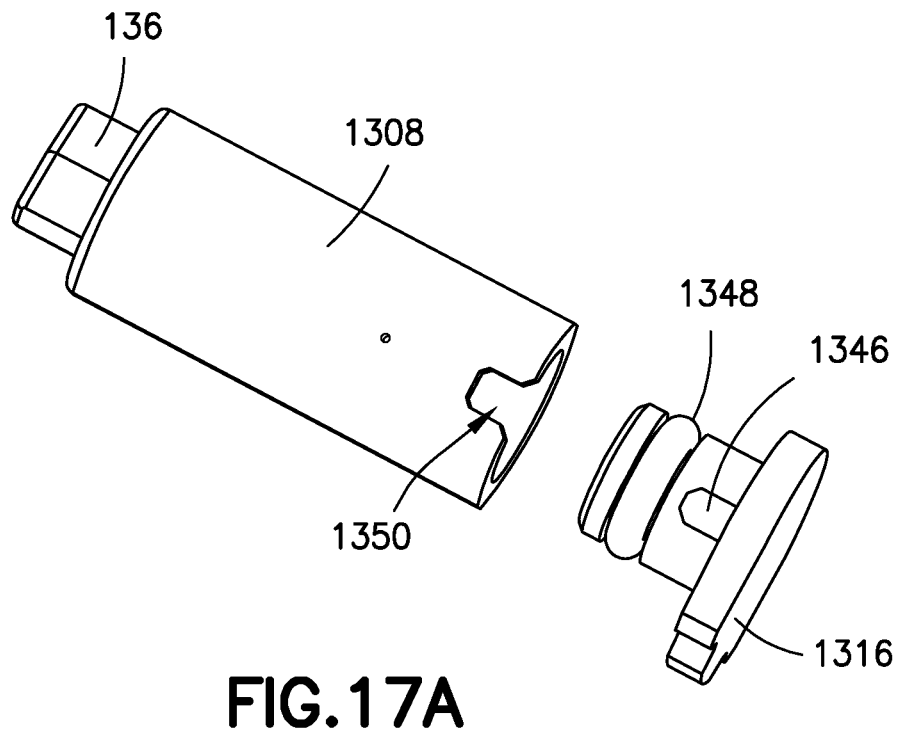
FIGS. 17A, 17B and 17C show multiple schematic views illustrating a method of assembly of a plug into a sleeve in accordance with the present invention.

FIG. 17A illustrates assembly of the plug 1316 with sleeve 1308. As shown, plug 1316 includes a key 1346, and a seal 1348. Seal 1348 provides a tight fit for the plug within sleeve 1308. Sleeve 1308 is provided with a recess 1350 adapted to receive key 1346. The key 1346 locks plug 1316 in rotational engagement with sleeve 1308. The plug 1316 is pressed against the end face of the (advanced) piston 1306 during assembly in order to minimize air in the pump chamber. Friction between seal 1348 and the inner surface of sleeve 1308 retain the plug 1316 axially. With appropriate selection of seal diameters, squeeze, and materials, the plug 1316 can also serve as an occlusion or overpressure sensor. Pump pressures greater than the threshold value will cause the plug 1316 to move axially and disengage with the sleeve rotational limit switch 1318. Friction holds the plug 1316 in position against pressures below a desired threshold. FIGS.

Figures 17B, 17C:
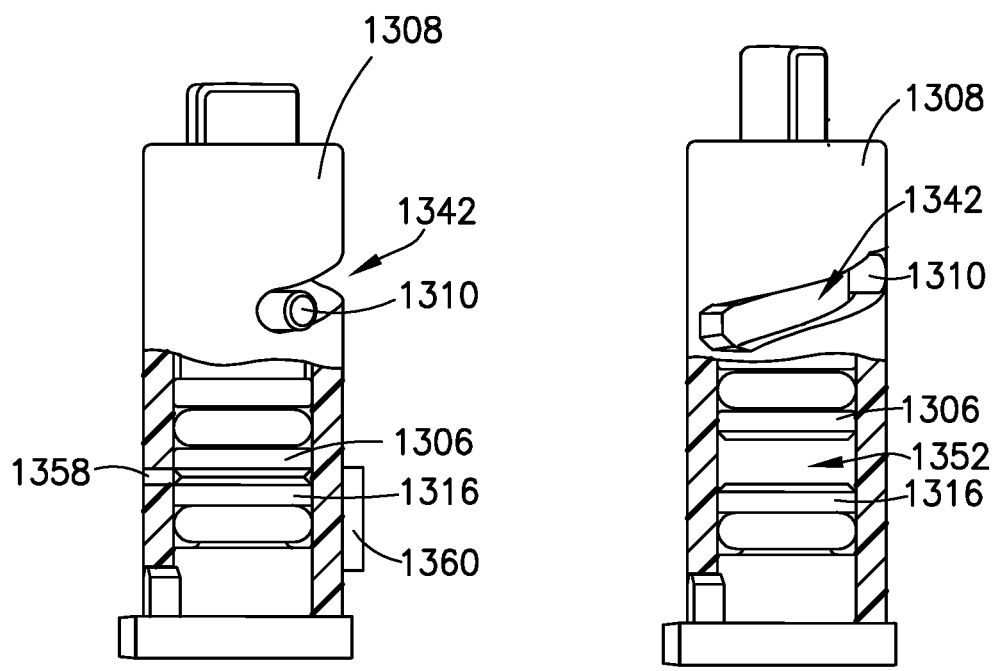

17B and 17C illustrate axial movement of the piston 1306 within sleeve 1308. FIG. 17B illustrates the piston 1306 in a first state with minimal or no pump volume between piston 1306 and plug 1316. As shown, coupling pin 1310 is abutted against the lowest end of helical groove 1342. FIG. 17C illustrates the piston 1306 in a second state with maximum pump volume 1352 between piston 1306 and plug 1316. As shown, coupling pin 1310 is abutted against the highest end of helical groove 1342.

Figure 18A:
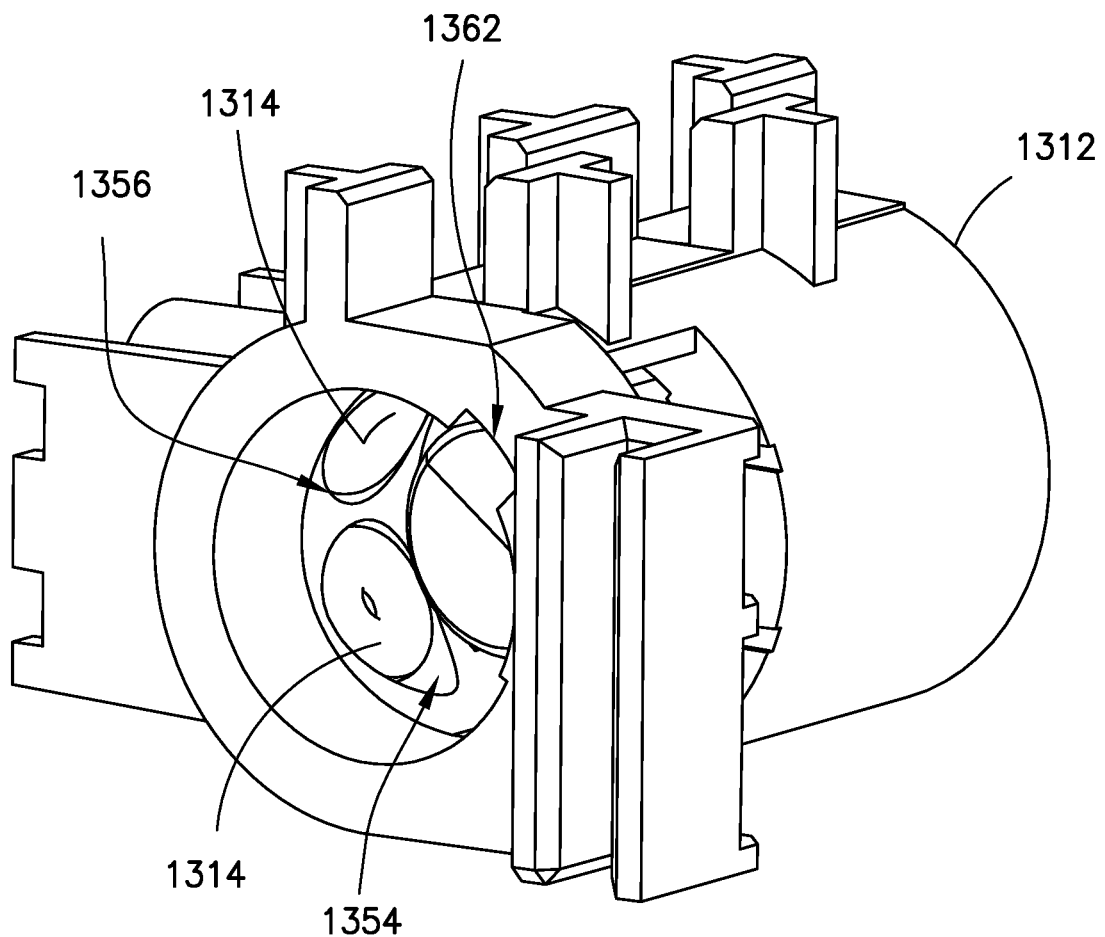
FIGS. 18A, 18B, 18C and 18D show multiple schematic views illustrating a method of assembly of a sleeve into a manifold in accordance with the present invention.
Figure 18B:
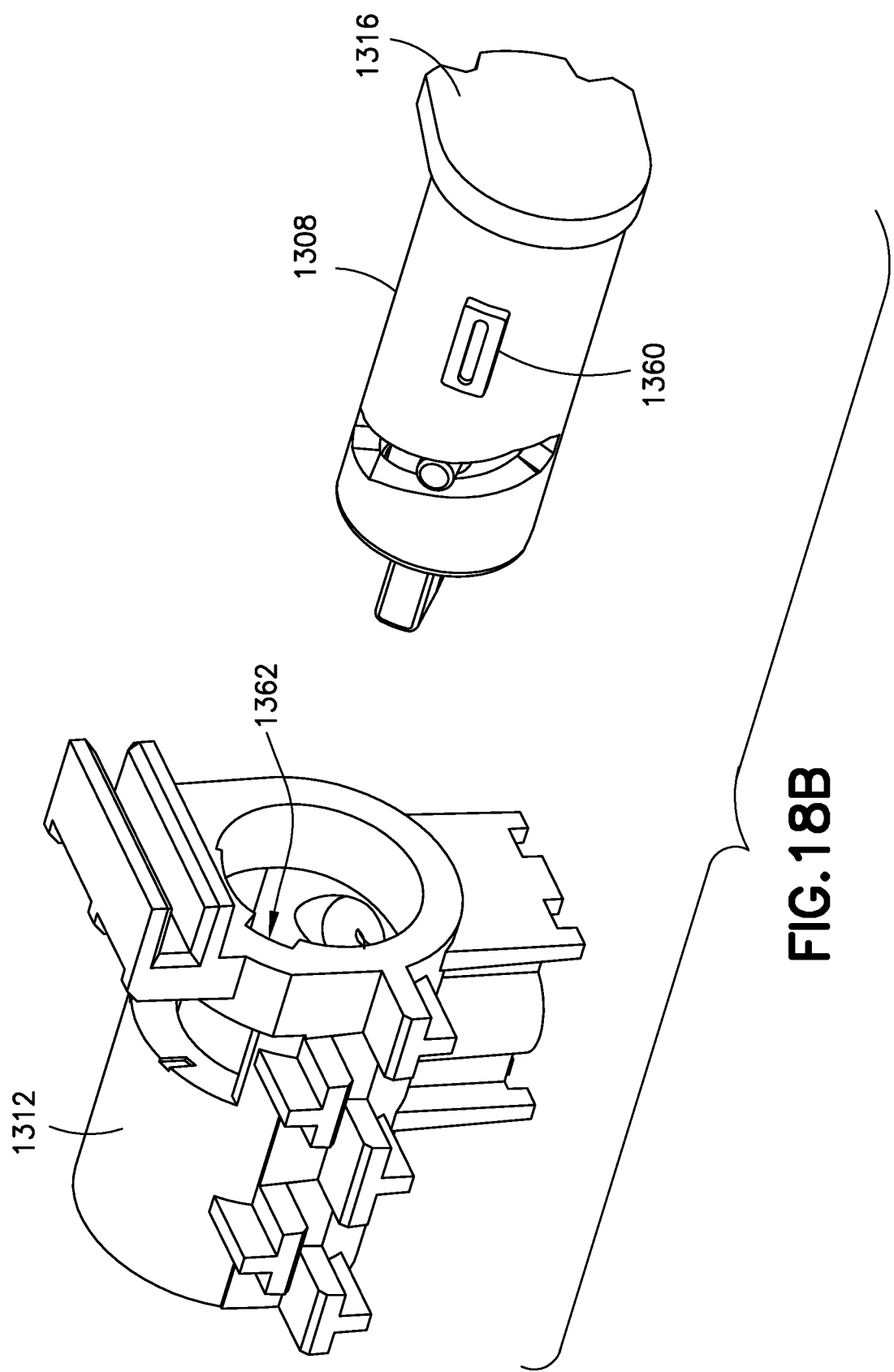
Figure 18D:
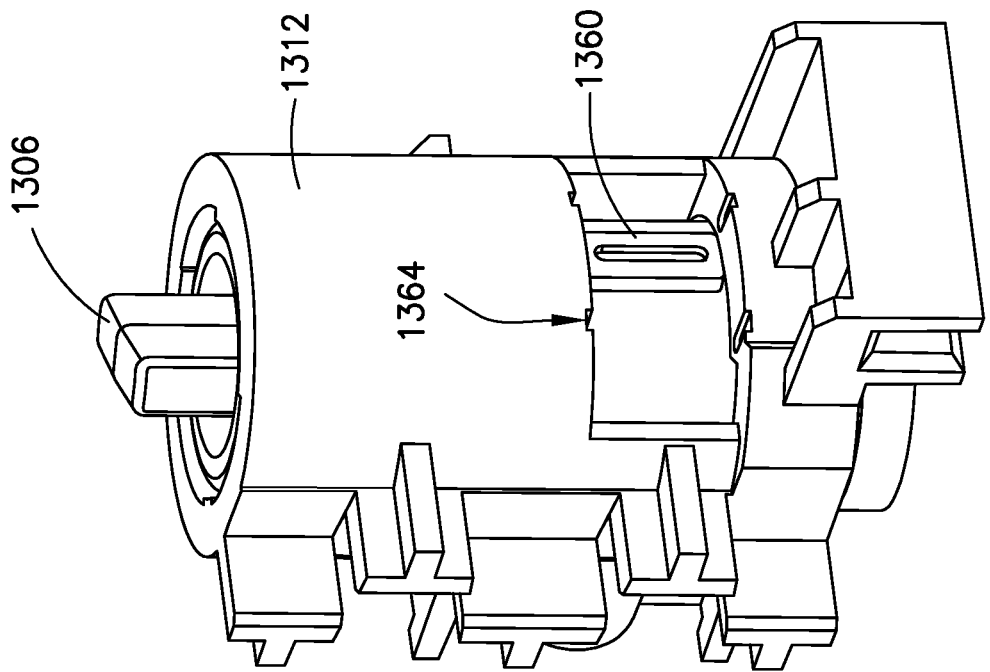
Figure 18C:
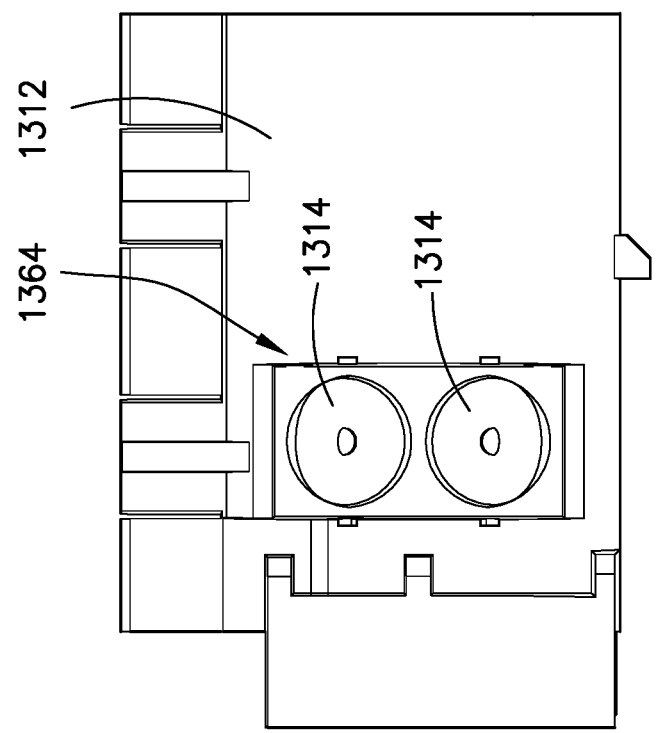

FIGS. 18A-18D illustrate the assembly of the sleeve 1308 into manifold 1312. As illustrated in FIG. 18A, manifold 1312 includes port seals 1314 to seal a reservoir port 1354 and a cannula port 1356, respectively. A small side hole 1358 (See FIG. 17B) on the sleeve rotationally shuttles back and forth between the two ports, which are 56 degrees apart. As shown in FIG. 18B, sleeve 1308 includes a tab 1360, and manifold 1312 includes a corresponding slot 1362 to permit sleeve 1308 to be assembled into the manifold 1312. FIG. 18C illustrates a manifold window 1364 provided in the manifold. Tab 1360 is received within and travels in window 1364 when the sleeve 1308 is assembled into manifold 1312. Tab 1360 and window 1364 interact to permit sleeve 1308 to rotate between two positions while preventing axial translation of the sleeve 1308 relative to the manifold 1312. Sleeve 1308 rotates between a first position in which side hole 1358 is aligned with the reservoir port 1354 and a second position in which the side hole 1358 is aligned with the cannula port 1356. FIG. 18D illustrates the sleeve 1308 assembled into the manifold 1312, with tab 1360 located within manifold window 1364.

Figure 19:
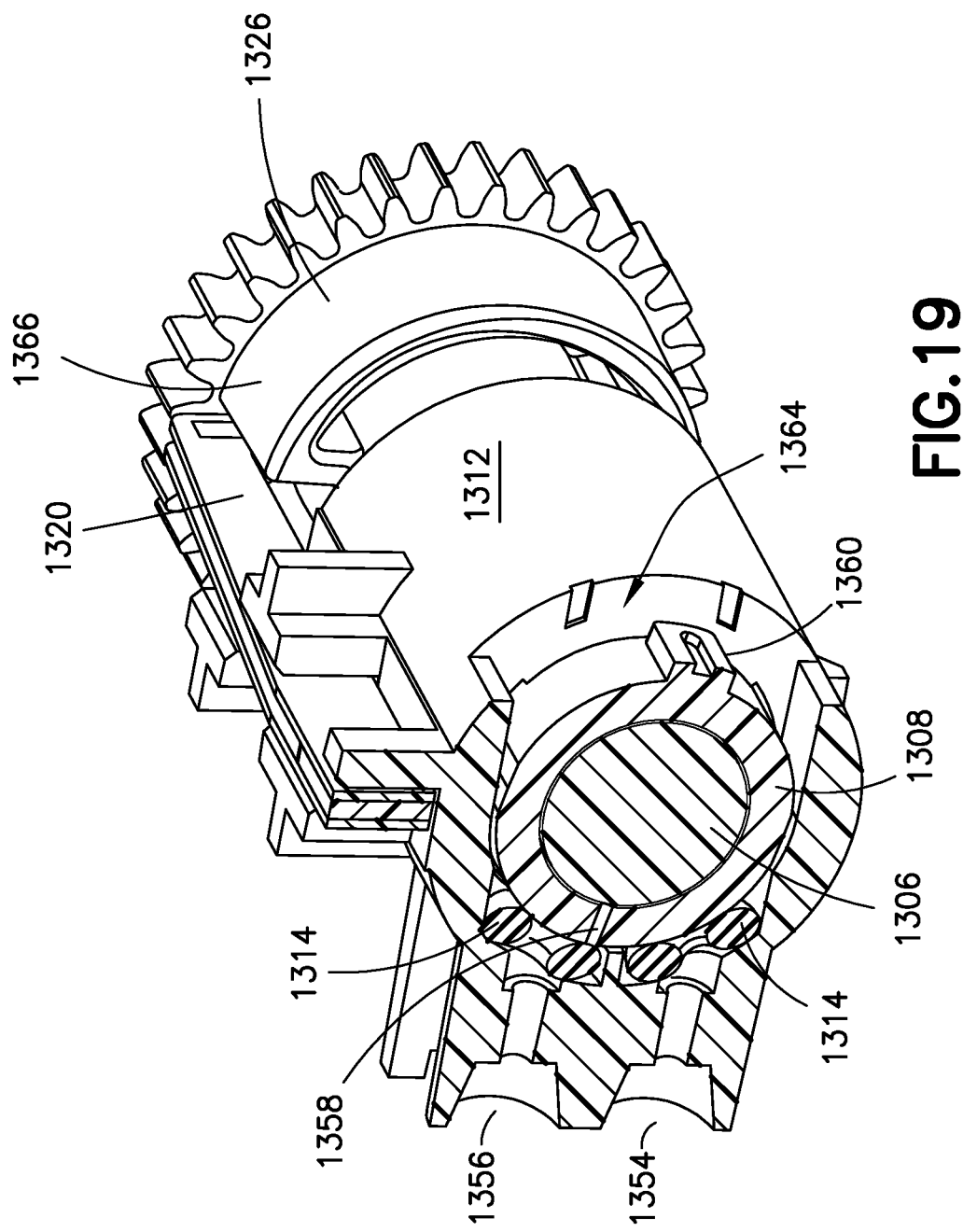
FIG. 19 is a schematic cross-sectional view of a pump assembly of an illustrative embodiment of a patch pump in accordance with the present invention.

FIG. 19 is a cross section of the assembled metering system. As illustrated, port seals 1314 are face seals which are compressed between the sleeve 1308 OD and recessed pockets in the manifold 1312. As also illustrated, tab 1360 is located within manifold window 1364, and side hole 1358 is shown in transition between the reservoir port 1354 and the cannula port 1356. Output gear 1326 includes a cam feature 1366 that engages rotational limit switch 1320 to signal the end of rotational movement of the piston 1306 and sleeve 1308 in either direction.

Figure 20A:
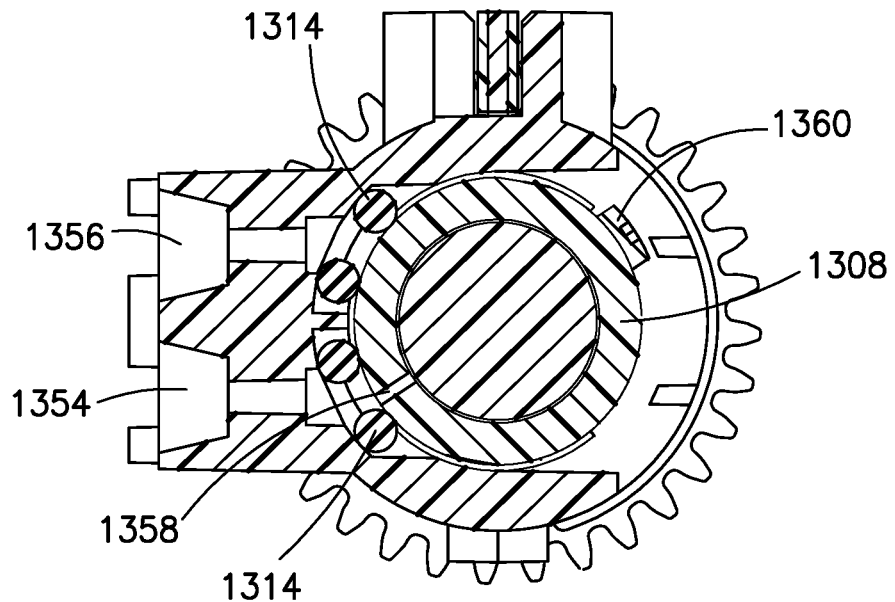
FIGS. 20A, 20B, 20C, 20D and 20E show multiple schematic cross-sectional views illustrating a method of valve state change in accordance with the present invention.
Figure 20B:
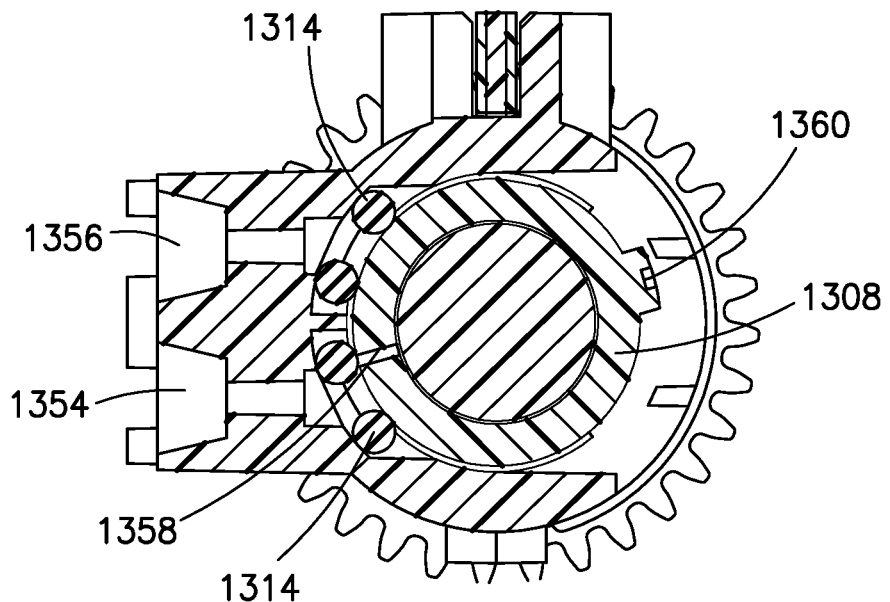
Figure 20C:
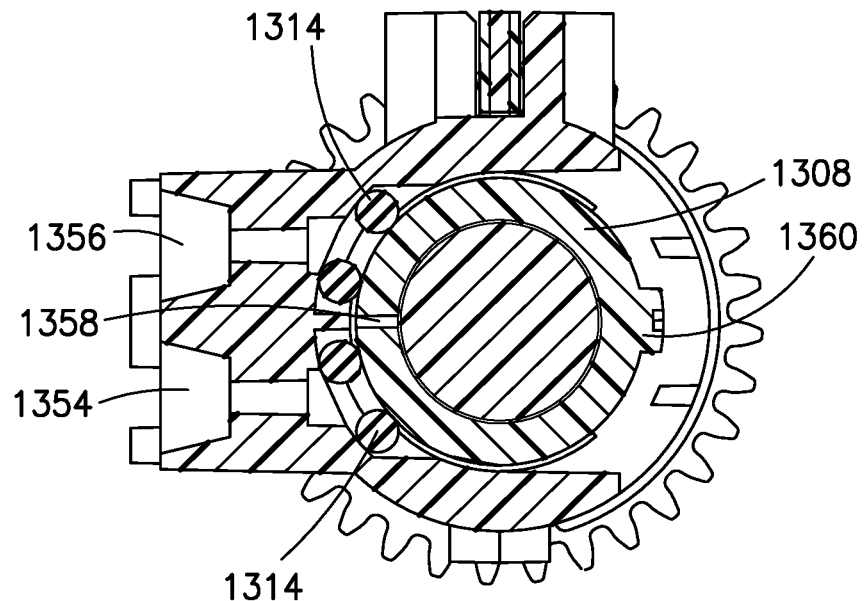
Figure 20D:
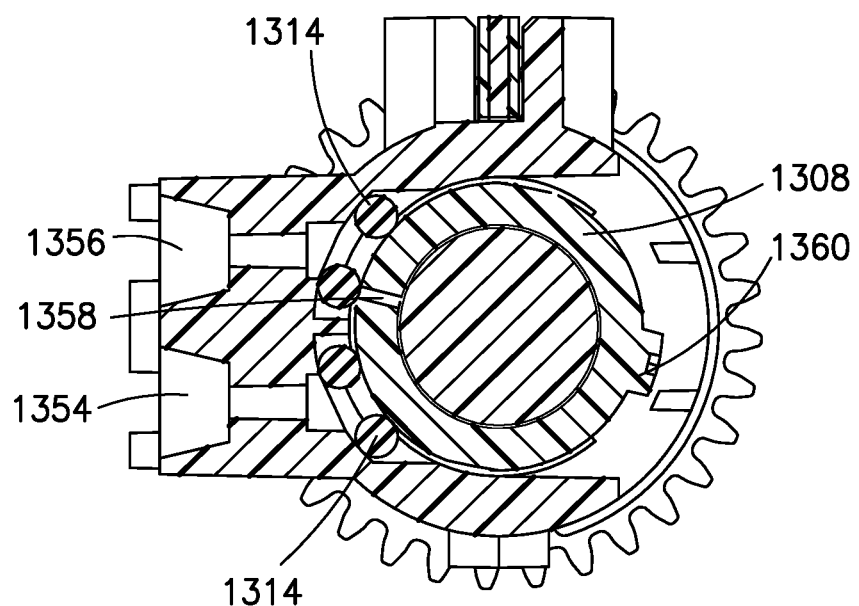
Figure 20E:
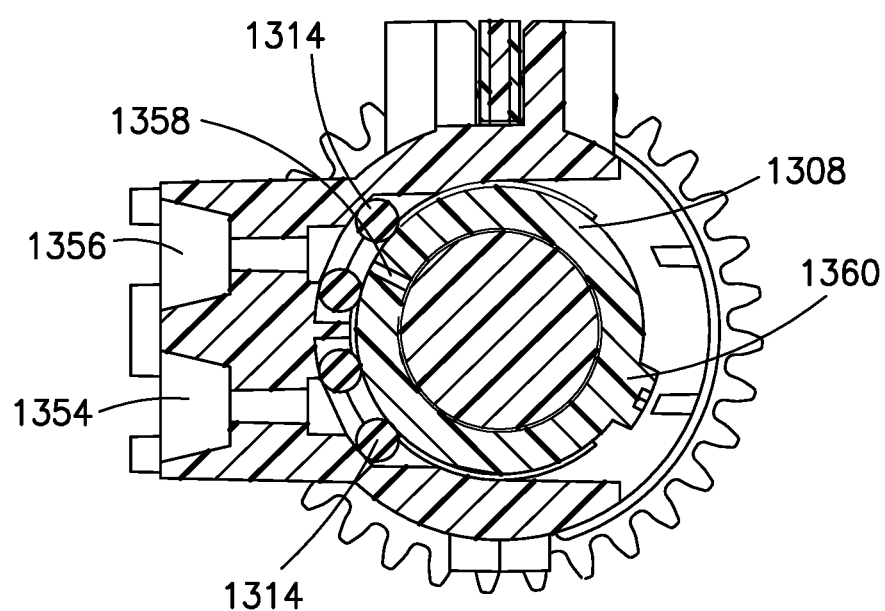

FIGS. 20A-20E are cross-section views illustrating rotation of the sleeve 1308 within manifold 1312 to move the side hole from alignment with reservoir port 1354 to alignment with cannula port 1356. FIG. 20A illustrates side hole 1358 aligned with the reservoir port 1354. While in this position, piston 1306 moves away from plug 1316 to fill volume 1352 with fluid from the reservoir. FIG. 20B illustrates the sleeve 1308 as it begins to rotate towards the cannula port 1356. In this position, the side hole 1358 is sealed by the seal 1314 on the reservoir port 1354. For this reason, the seal 1314 and the side hole 1358 diameter are preferably selected such that seal 1314 covers the opening of the side hole 1358. FIG. 20C illustrates the side hole 1358 of sleeve 1308 between the seal 1314 of the reservoir port 1354 and the seal 1314 of the cannula port 1356. In this position, neither seal 1314 blocks the side hole 1358, but surface tension of the liquid holds the liquid in the pump chamber. FIG. 20D illustrates the side hole 1358 rotated further to a position where the seal 1314 of the cannula port 1356 covers the opening of the side hole 1358. Finally, FIG. 20E illustrates the side hole 1358 rotated into alignment with the cannula port 1356. While in this position, the piston 1306 translates axially to reduce the volume 1352, forcing the fluid out of the cannula port 1356 and to the cannula.

Figure 21A:
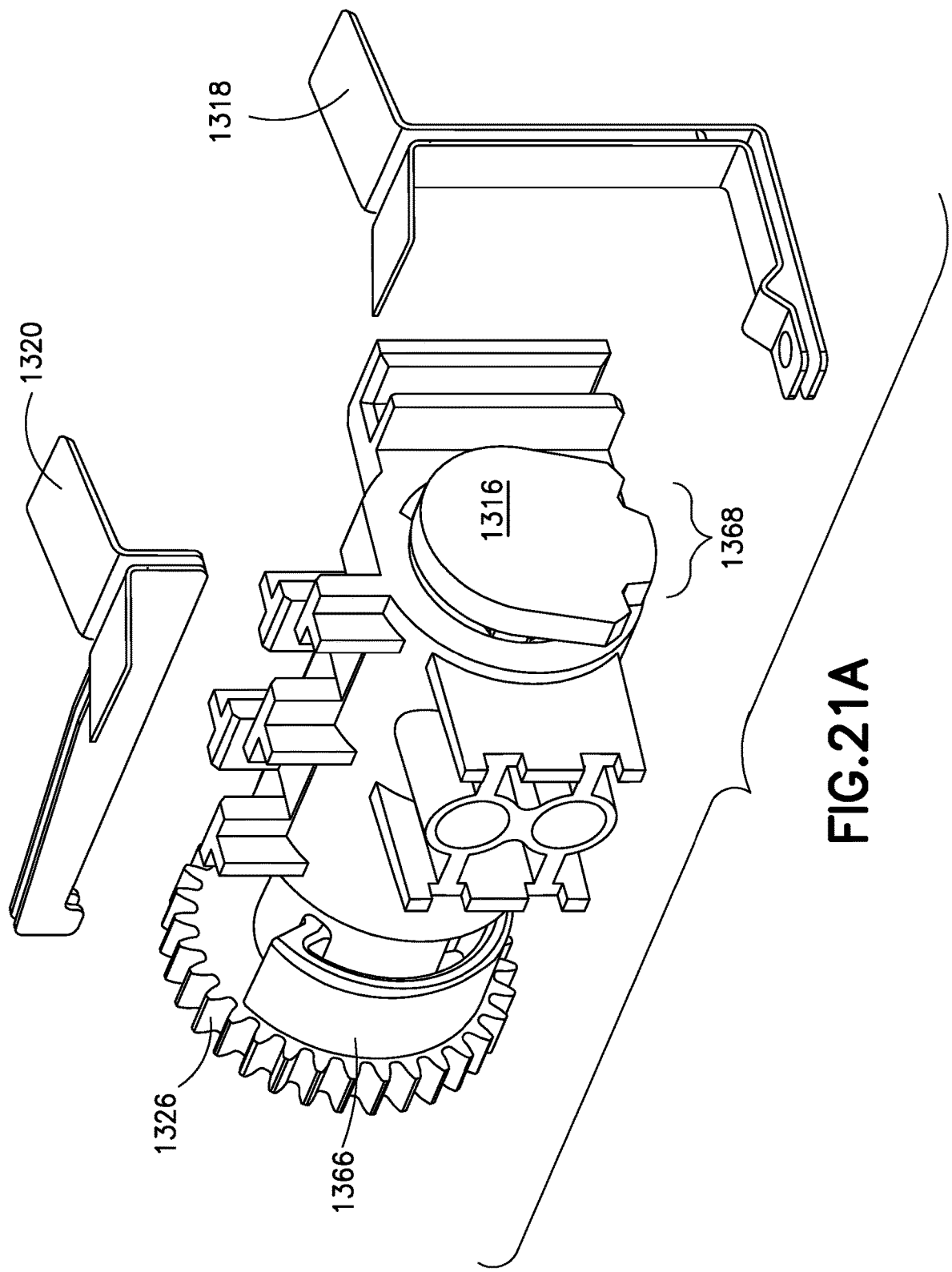
FIGS. 21A, 21B and 21C show multiple views of a limit switches for pump and sleeve rotation in a metering sub-system of an illustrative embodiment of a patch pump in accordance with the present invention.
Figure 21B:
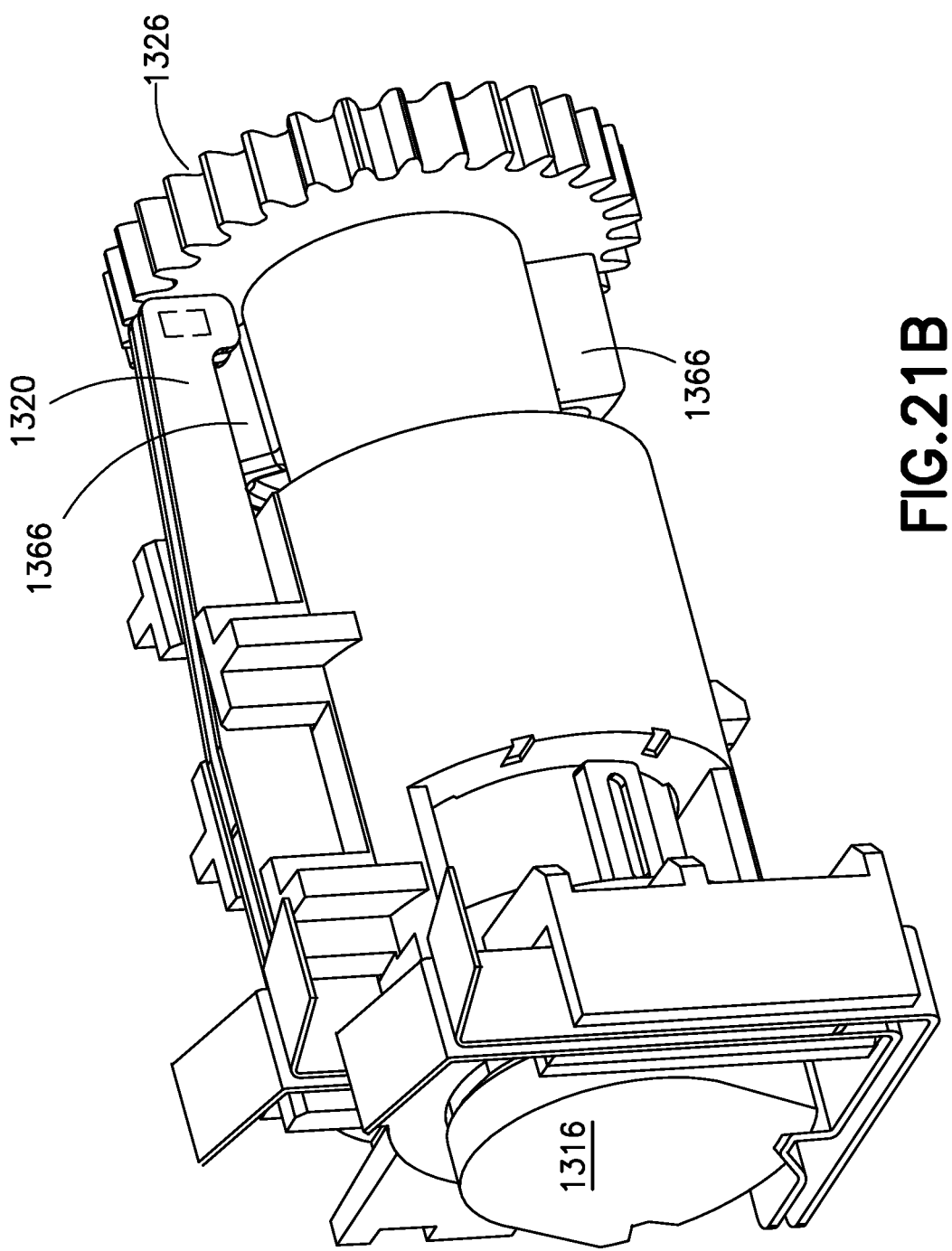
Figure 21C:
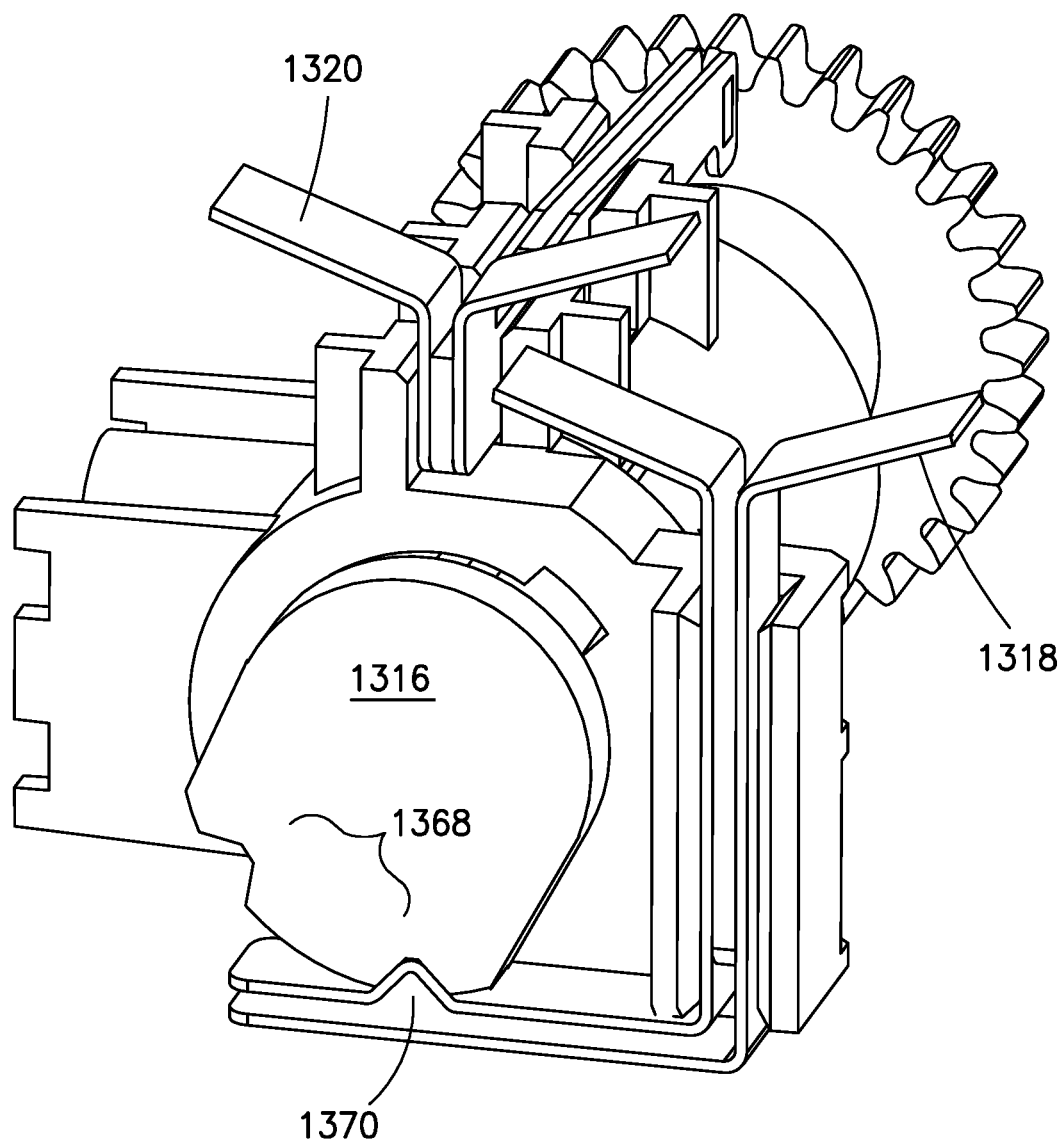

FIGS. 21A-21C illustrate operation of the limit switches. As shown in FIG. 21A, plug 1316 includes a cam feature 1368 that interacts with limit switch 1318. As the sleeve 1308 and plug 1316 rotate, the cam feature 1368 causes metal flexures of limit switch 1318 to come into contact with one another, until the plug 1316 has fully rotated to the next position. A bump 1370 in one of the flexures rests in the cam feature 1368 as illustrated in FIG. 21C when the plug 1316 is in either end point of the plug rotation. The limit switch 1318 opening and closing each rotation cycle signals that the plug 1316 remains in proper alignment with the limit switch 1318. Under overpressure or occlusion conditions, increased pressure will cause plug 1316 to slide out from sleeve 1308, and out of alignment with the limit switch 1318. Thus, overpressure conditions are detected. Limit switch 1320 is engaged by cam feature 1366 of output gear 1326 at each end of the rotation cycle. This signals the motor 1334 to reverse directions. With two metal flexures, as illustrated, it is not possible to determine from the limit switch which rotation cycle was completed. However, as will be appreciated, a third flexure would permit the direction of engagement to be determined.

Figure 22A:
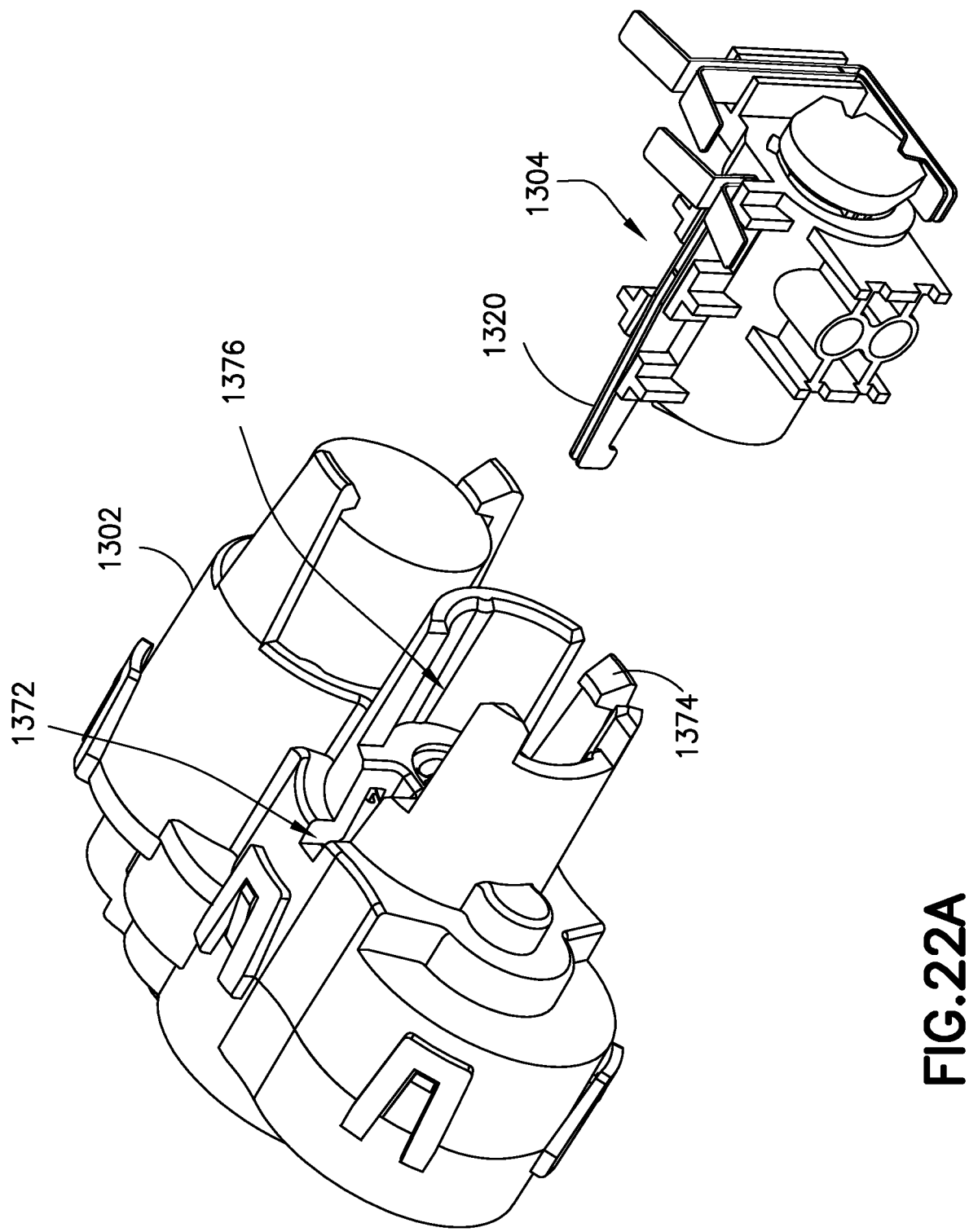
FIGS. 22A, 22B and 22C show multiple schematic cross-sectional views illustrating a method of assembly of a pump into a gearbox in accordance with the present invention.
Figure 22B:
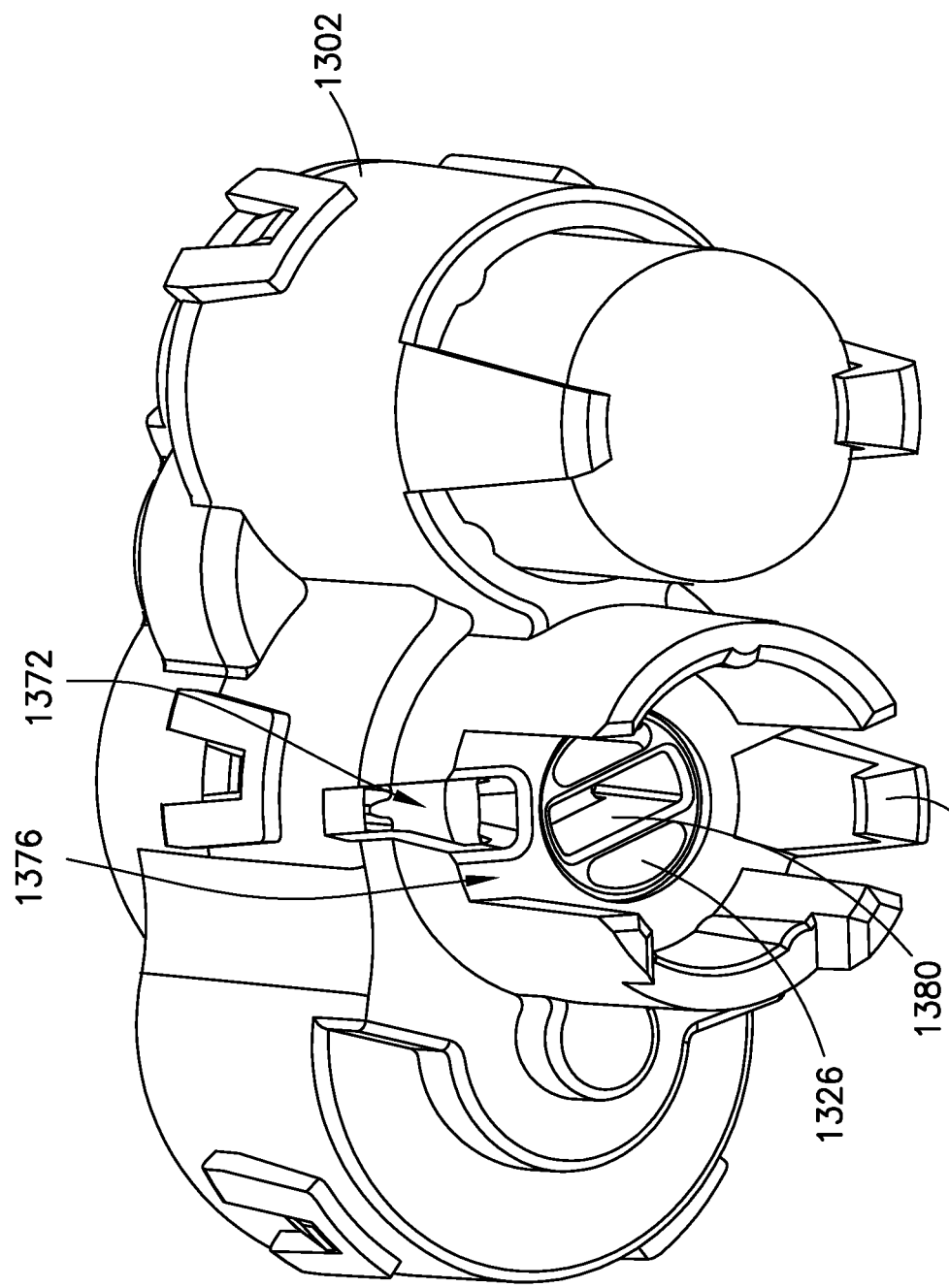
Figure 22C:
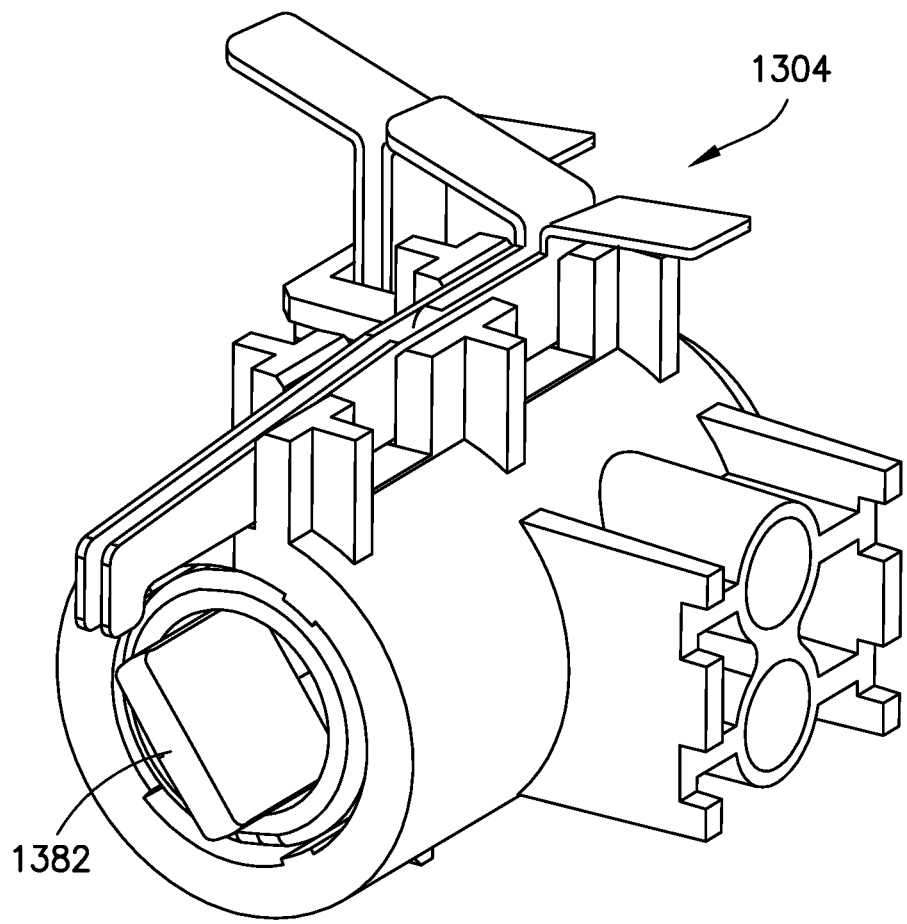

FIGS. 22A-22C illustrate the assembly of the motor and gearbox 1302 with the pump assembly 1304. As illustrated in FIGS. 22A and 22B, motor and gearbox 1302 includes an opening 1372 to receive rotational limit switch 1320. In this manner, output gear 1326, which is internal to the gearbox housing, can access and engage the flexures of limit switch 1320. Motor and gearbox 1302 also includes an axial retention snap 1374 so that the pump assembly 1304 may be snap-fit to the motor and gearbox 1302. Motor and gearbox 1302 includes a rotational key 1376 within a pump-receiving socket 1378 to receive pump assembly 1304 and to prevent rotation of the pump assembly 1304 relative to the motor and gearbox 1302. Output gear 1326 includes a slot 1380 (FIG. 22B) adapted to receive a tab 1382 (FIG. 22C) provided on the piston 1306. When assembled, tab 1382 is received into slot 1380 so that the output gear 1326 can transmit torque to the piston 1306. As the output gear 1326 rotates, the pump piston tab 1382 both rotates and slides axially in the slot. Metal spring flexures on the motor connections and limit switches are used to make electrical contact with pads on a circuit board during final assembly.

In operation, the pump cycle of the above described embodiment includes five steps. First, an approximately 120° pump discharge (counterclockwise when viewing from the pump toward the gearbox); a 56° valve state change (counterclockwise); a 140° pump intake (clockwise); a 56° valve state change (clockwise); and an approximate 20° jog (counterclockwise) to clear the limit switch. A total pump cycle requires 196 degrees of output gear rotation in each direction.

FIGS. 23A-30C illustrate a pump cycle. For the sake of clarity, only the output gear 1326 of the gearbox assembly 1302 is shown in the figures.

Figure 23A:
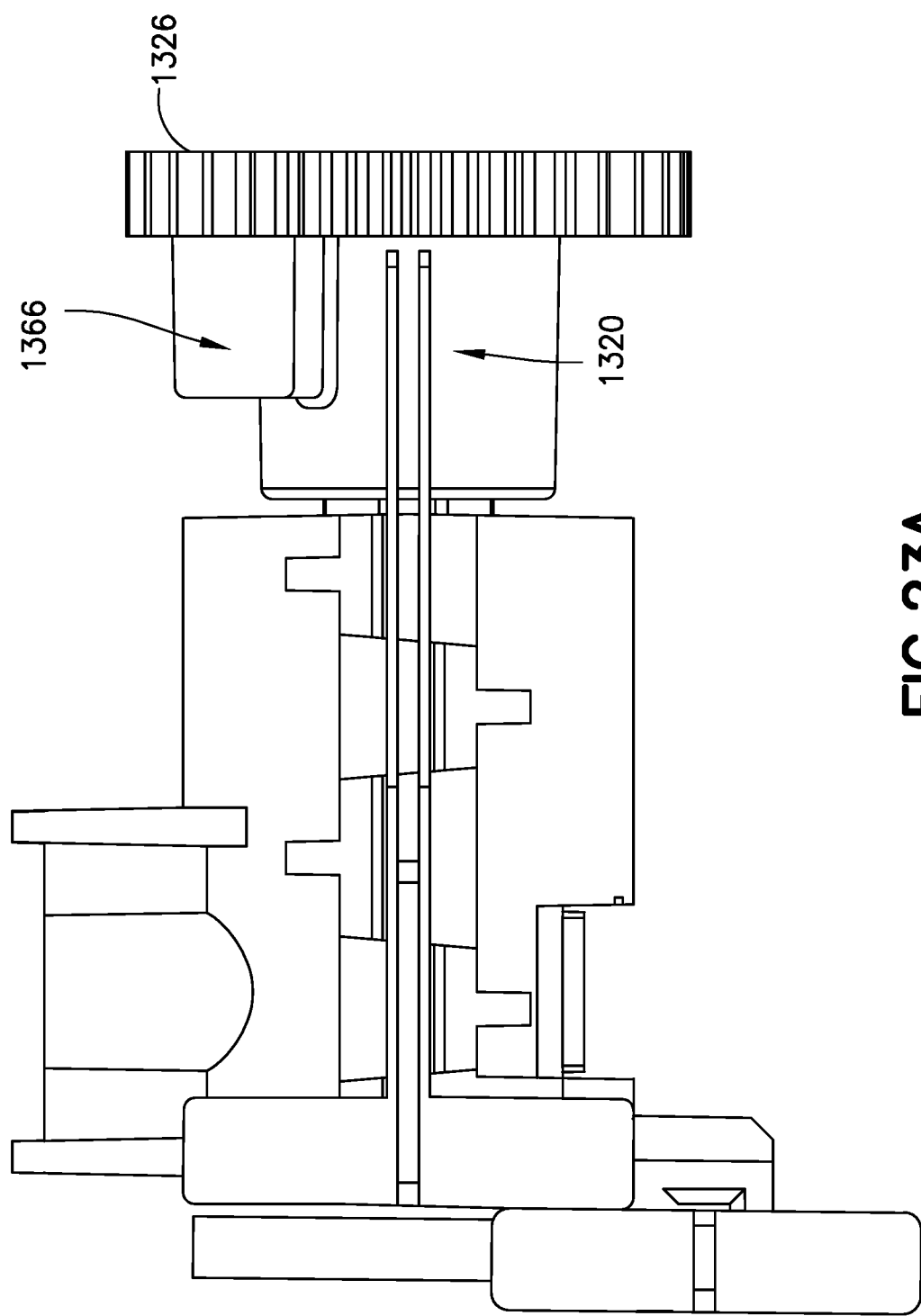
FIGS. 23A, 23B and 23C show multiple views of a metering sub-system of an illustrative embodiment of a patch pump in accordance with the present invention, in a starting position.
Figure 23B:
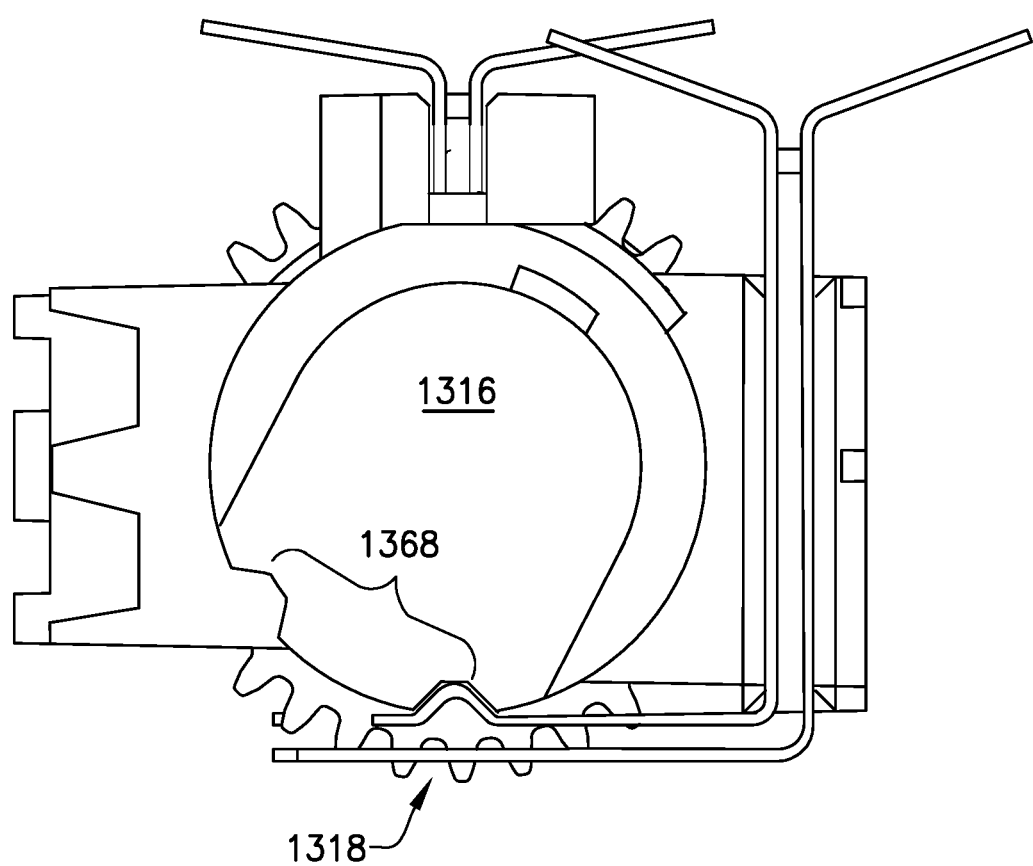
Figure 23C:
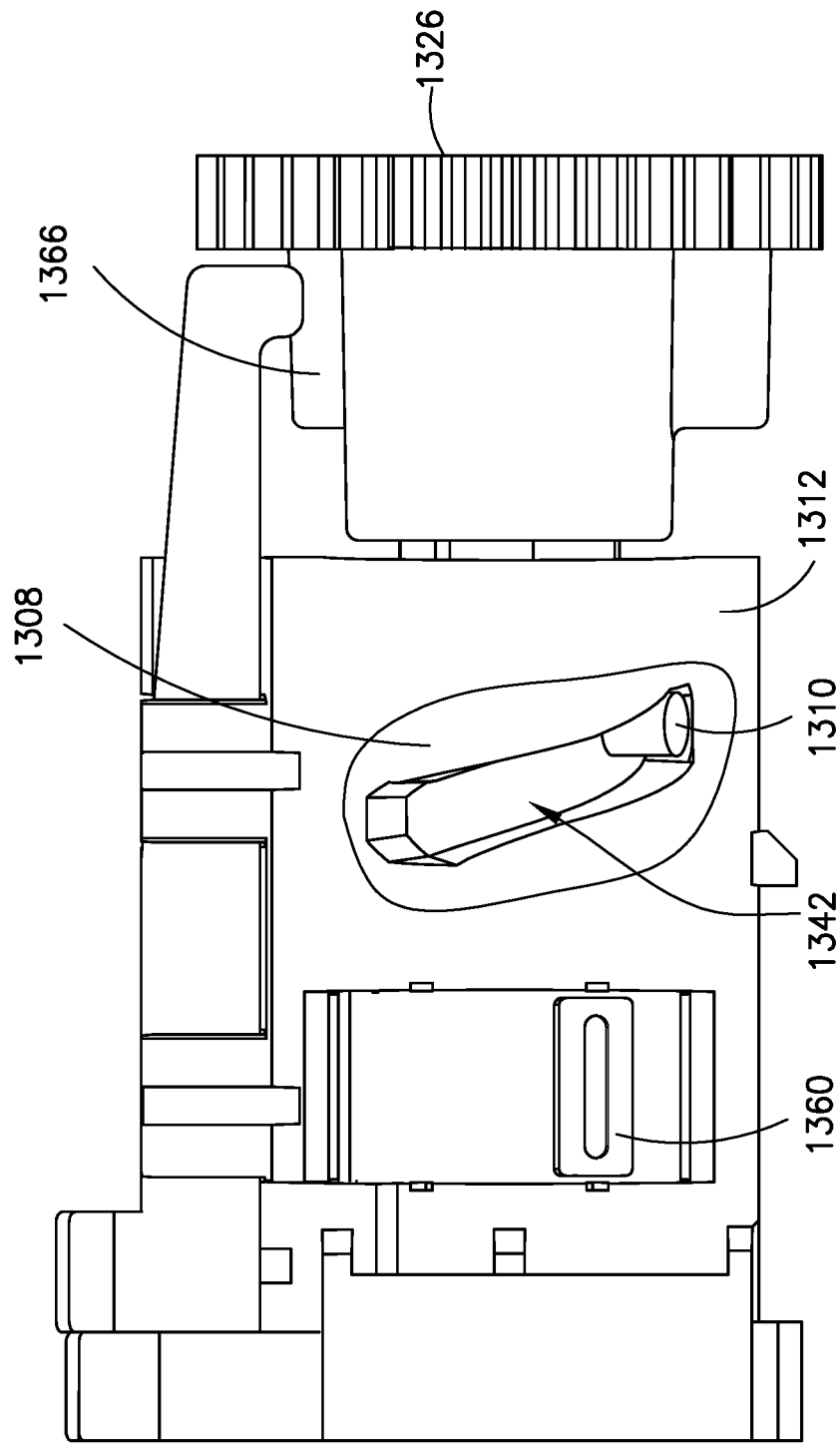

FIG. 23A illustrates a starting position. As shown, the cam 1366 of output gear 1326 is not in contact with rotational limit switch 1320, such that the flexures are not in contact with one another. The pump piston 1306 is retracted, as shown by the position of the coupling pin 1310 within helical groove 1342 in FIG. 22C. In this position, sleeve 1308 blocks the reservoir flow path, the cannula port 1356 is open to the side hole 1358 of the sleeve 1308, and the rotational limit sensor 1320 and the sleeve sensor 1318 (See FIG. 23B) are both open.

Figure 24B:
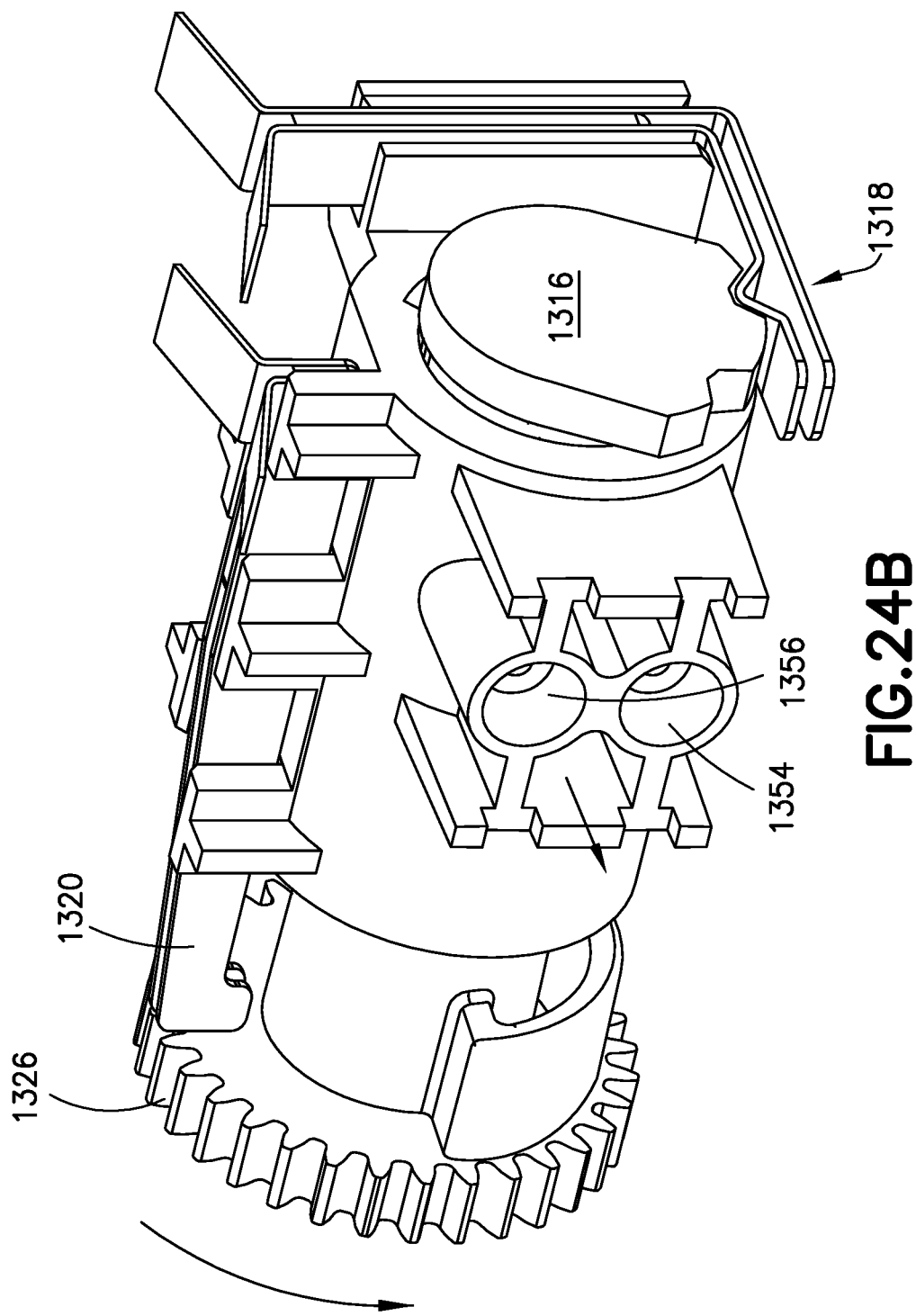

FIGS. 24A and 24B illustrate the metering sub-system during a discharge stroke. The output gear 1326 turns the pump piston 1306 in a first rotational direction (see arrow in FIG. 24B), which is driven along the helical path of the helical groove 1342 in the sleeve 1308 via the coupling pin 1310 (See FIG. 24A). The pump piston 1306 translates away from the gearbox while rotating, expelling fluid from the pump chamber 1352 and out of the cannula port 1356. During the discharge stroke, friction between the port seals 1314 and the outside diameter of the sleeve 1308 should be high enough to ensure that the sleeve 1308 does not rotate during this portion of the cycle.

Figure 25B:
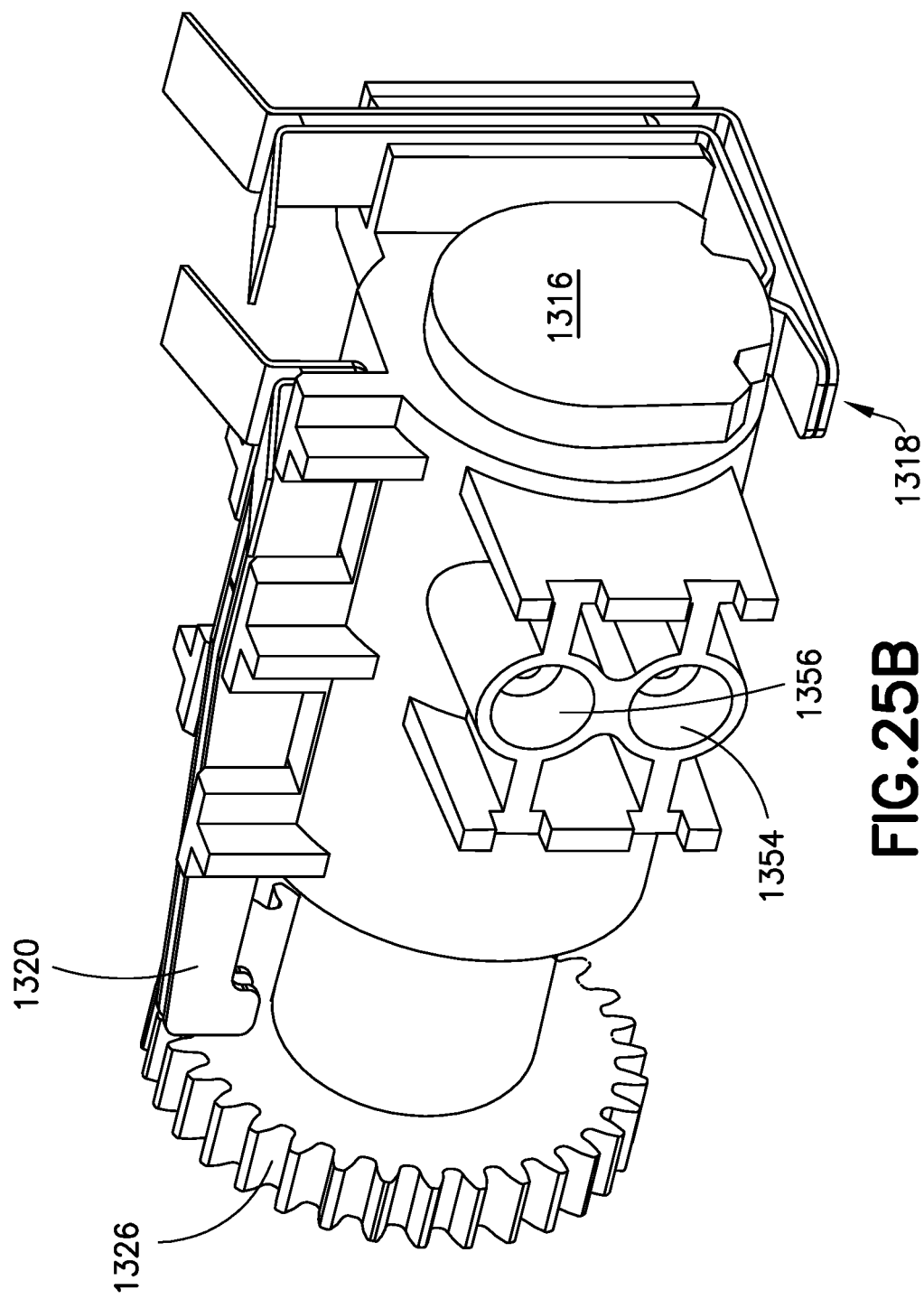
Figure 25C:
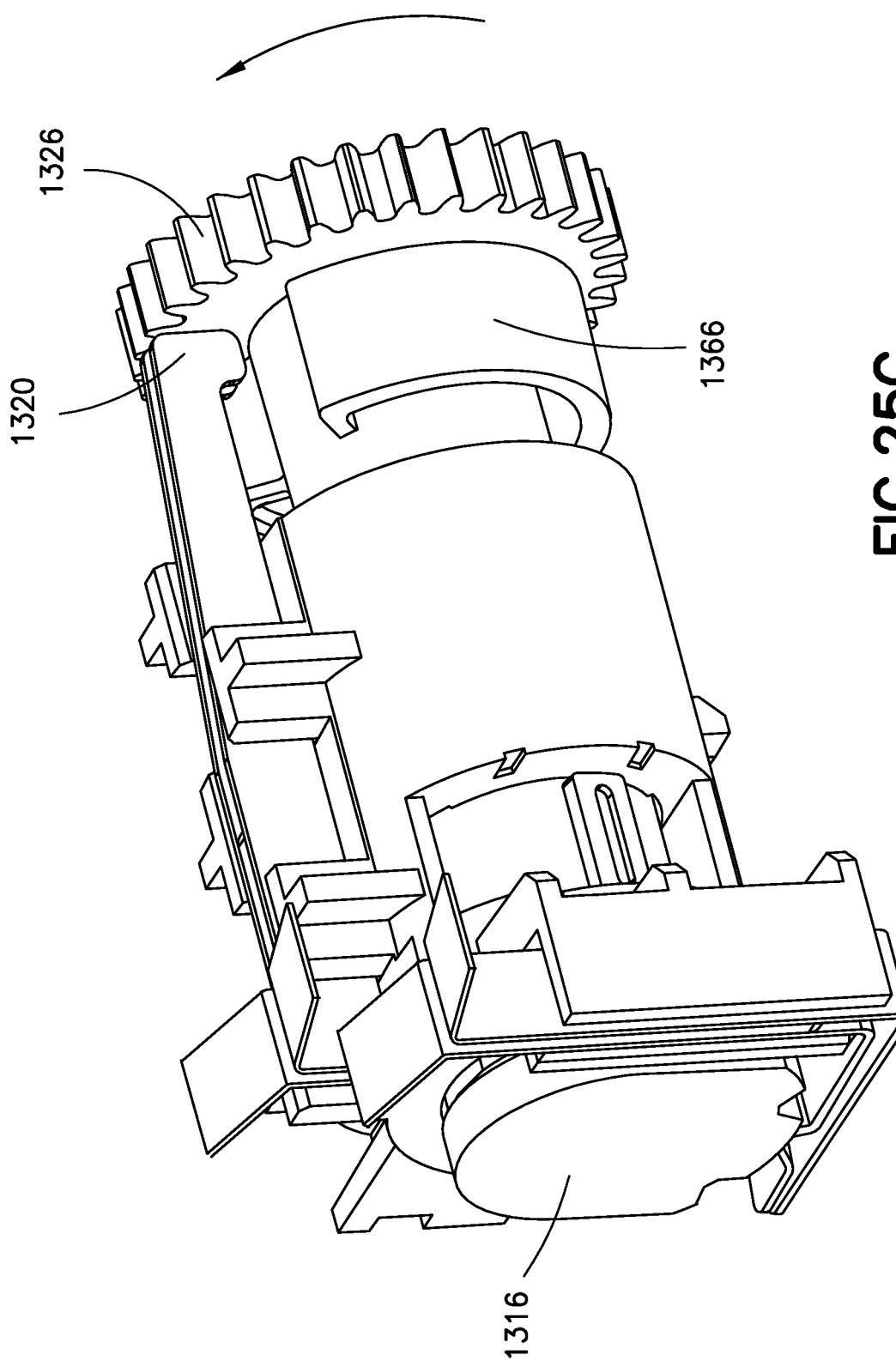

FIGS. 25A-25C illustrate the metering sub-system during a valve state change after a discharge stroke. As shown in FIG. 25A, after coupling pin 1310 reaching the distal end of helical groove 1342, torque continues to be transmitted from the output gear 1326, to the pump piston 1306, and to the sleeve 1308 via the coupling pin 1310. The sleeve 1308 and pump piston 1306 rotate as a unit with no relative axial motion. The side hole 1358 (not shown in FIGS. 25A-25C) on the sleeve 1308 moves between the reservoir port 1354 and the cannula port 1356. Tab 1360 moves in the direction shown by the arrow within the window 1364 of manifold 1312. As shown in FIG. 25B, sleeve limit switch 1318 is closed by the cam surface of plug 1316.

Figure 26A:
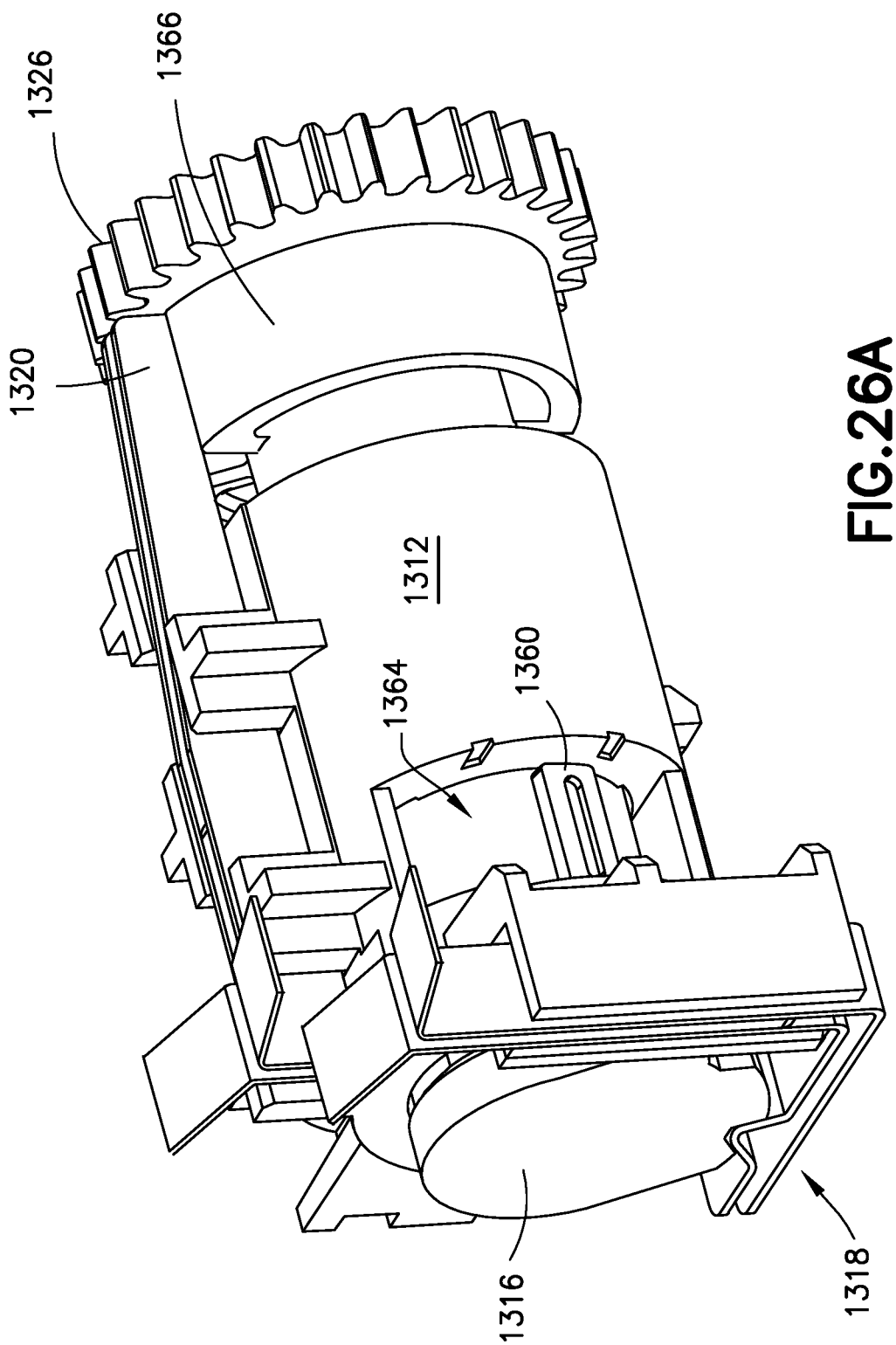
FIGS. 26A and 26B show multiple views of a metering sub-system of an illustrative embodiment of a patch pump in accordance with the present invention, in a discharge rotational stop position.
Figure 26B:
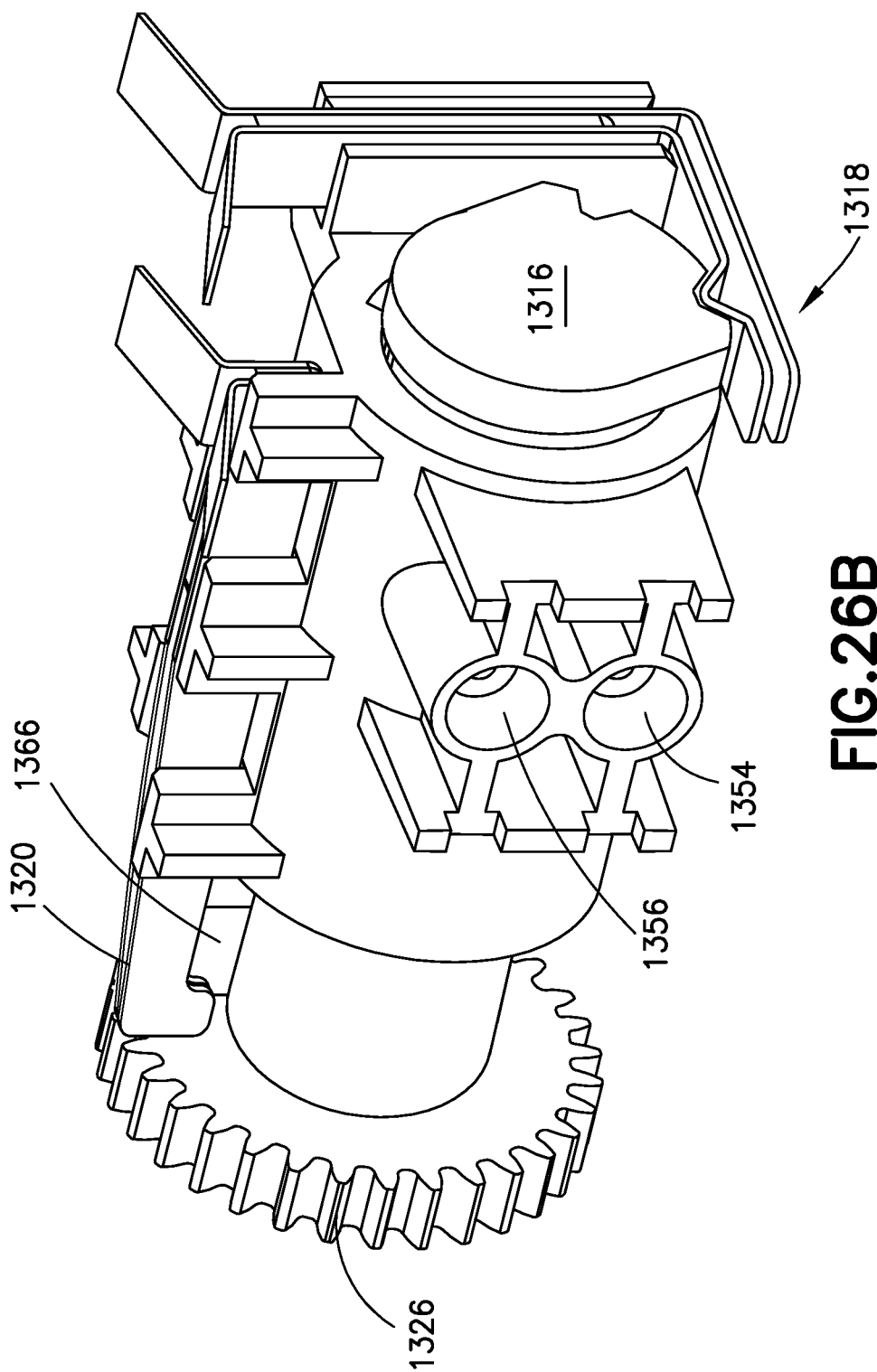

FIGS. 26A and 26B show the metering sub-system in a discharge rotational stop position. The side hole 1358 (not shown in FIG. 26A or 26B) of the sleeve is aligned with the reservoir port 1354, the pump volume 1352 is collapsed, and the cannula port 1356 is blocked. Plug 1316 in a stop position, and sleeve limit switch 1318 is open. Output gear cam 1366 contacts rotational limit switch 1320 to signal the end of the rotation, such that output gear 1326 stops to reverse direction.

Figure 27B:
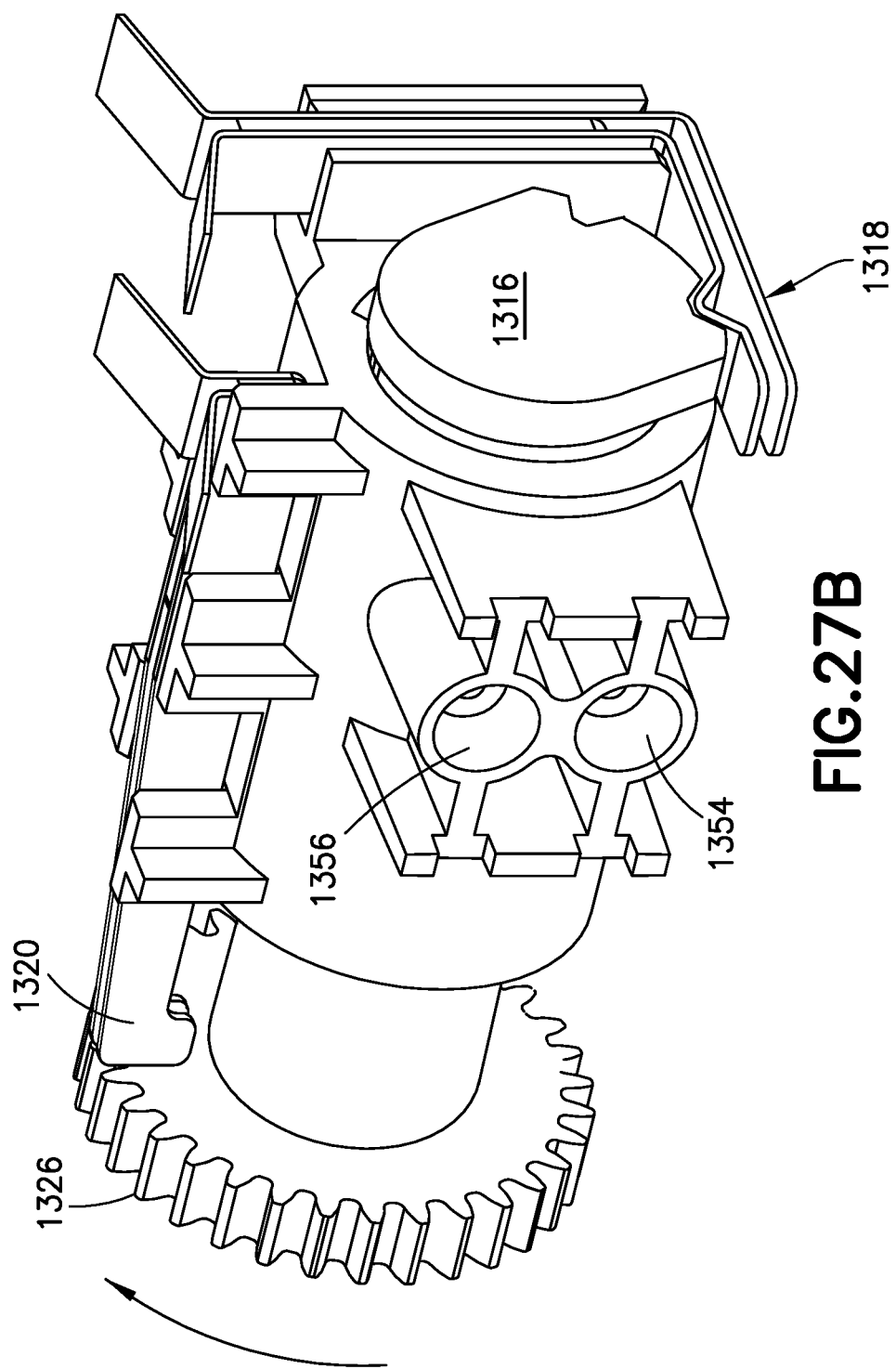

FIGS. 27A and 27B show the metering sub-system during an intake stroke. The output gear 1326 turns the pump piston 1306 in the direction shown by the arrow in FIG. 27B. The piston 1306 is translated axially relative to the sleeve 1308 due to interaction of the coupling pin 1310 within the helical groove 1364. The pump piston 1306 translates toward the gearbox, pulling fluid from the reservoir into the pump chamber 1352. During the intake stroke, friction between the seals and the outside diameter of the sleeve 1308 should be high enough to ensure that the sleeve 1308 does not rotate relative to the manifold 1312.

Figure 28A:
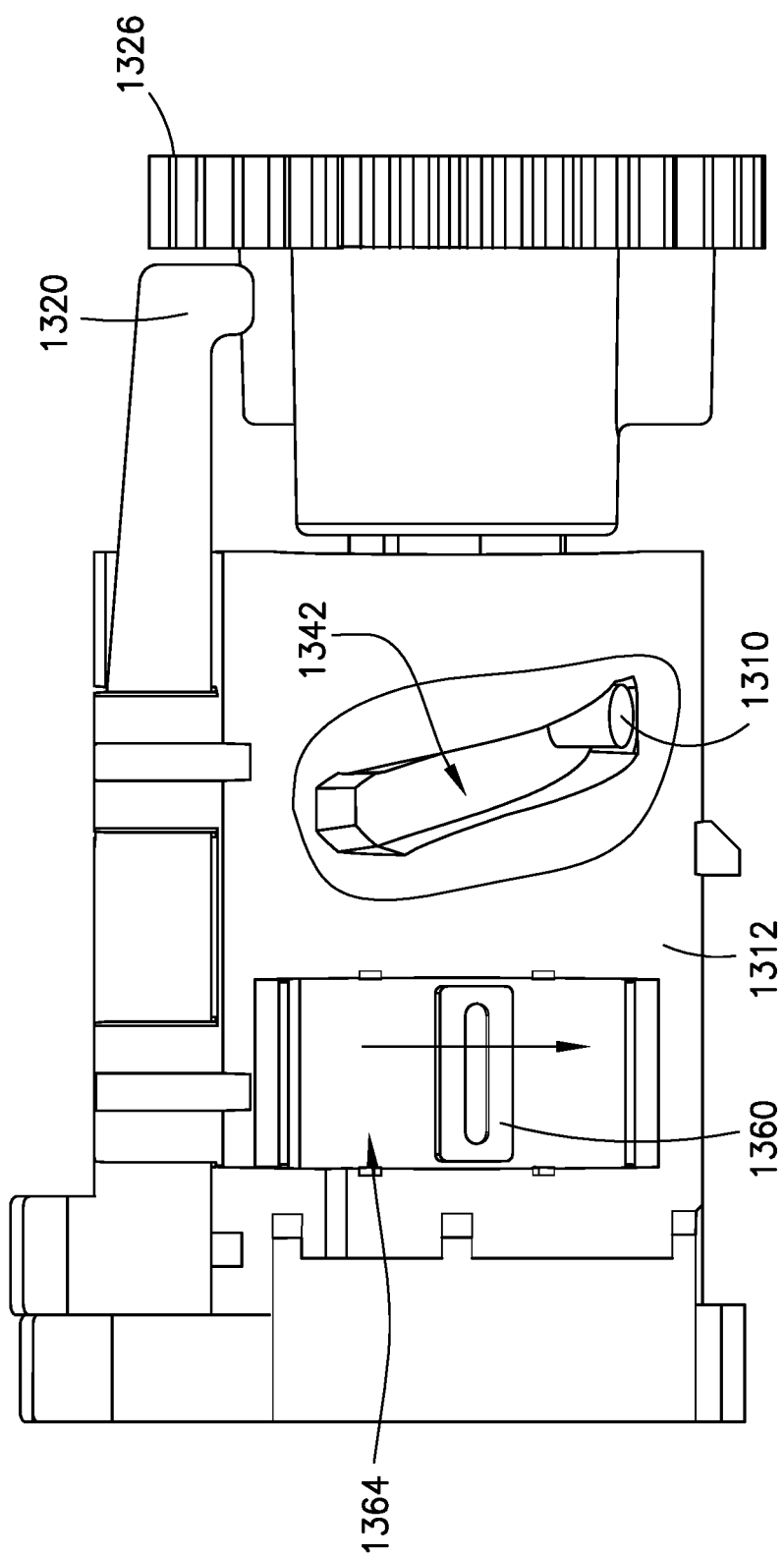
FIGS. 28A, 28B and 28C show multiple views of a metering sub-system of an illustrative embodiment of a patch pump in accordance with the present invention, during a valve state change after an intake stroke.
Figure 28B:
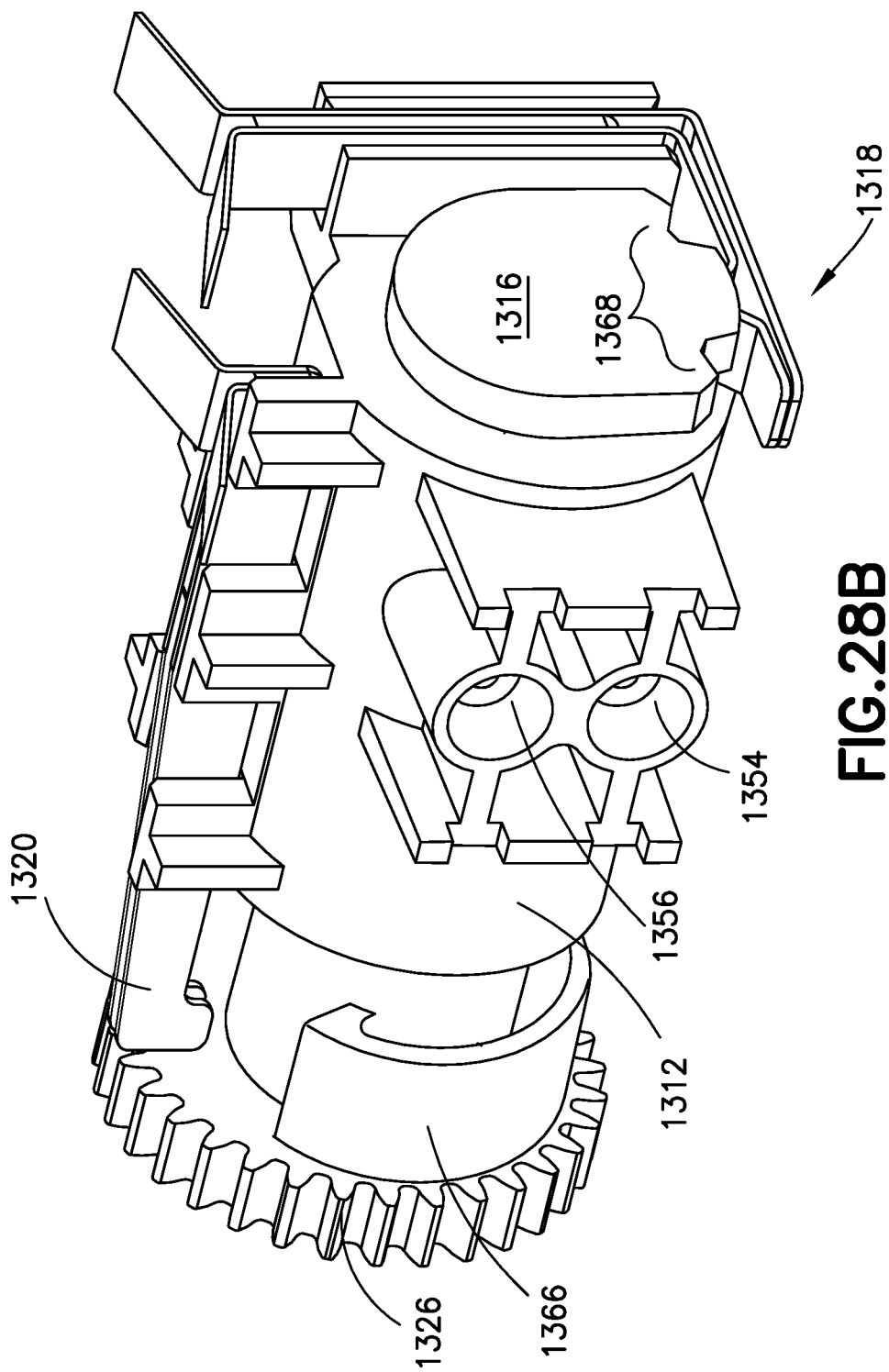
Figure 28C:
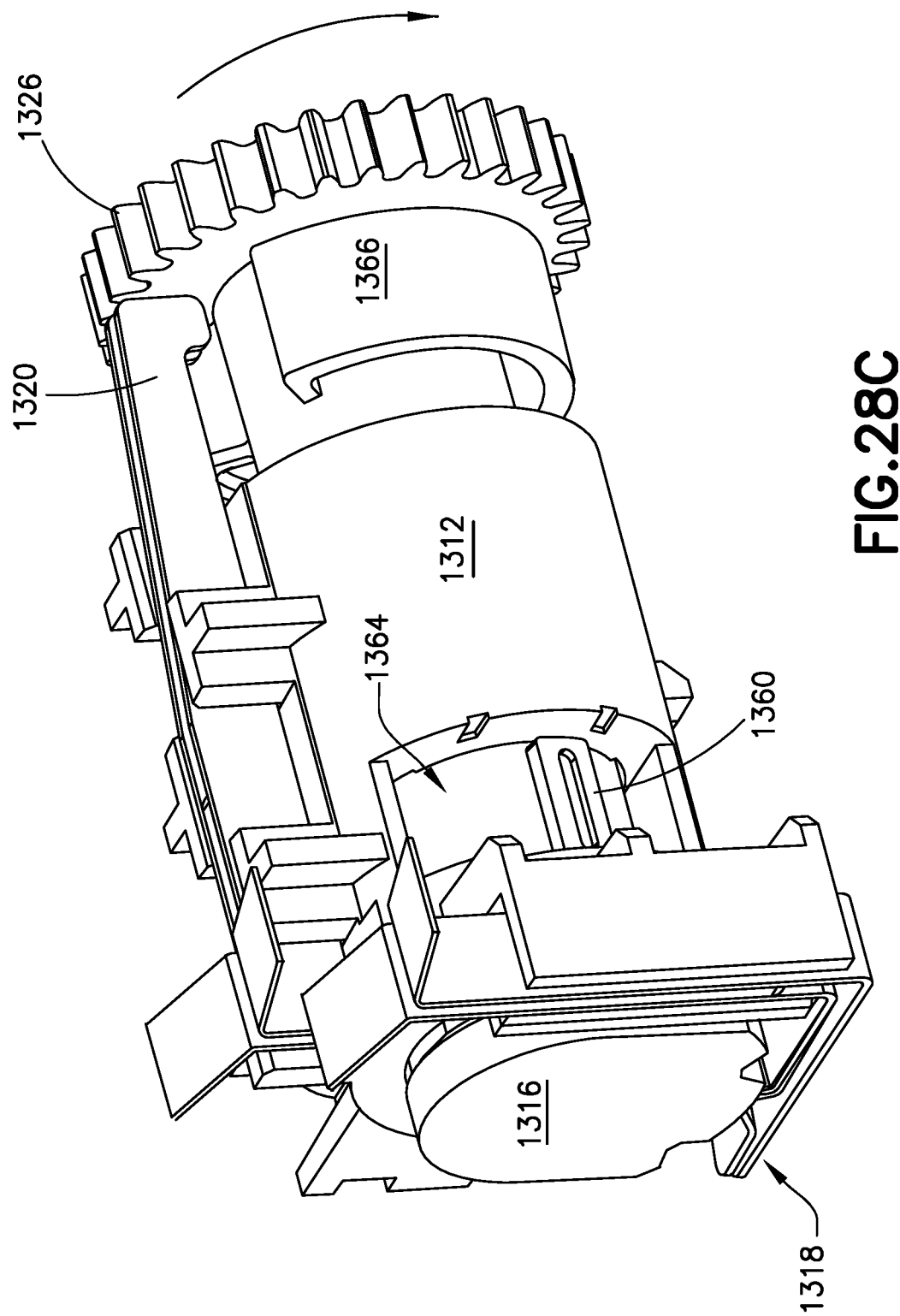

FIGS. 28A to 28C show the metering sub-system during a valve state change after an intake stroke. Coupling pin 1310 reaches the upper end of helical groove 1342, motor 1302 continues to deliver torque, causing the sleeve 1308 and piston 1306 to rotate together. Tab 1360 on sleeve 1308 moves in the direction shown in the arrow in FIG. 28A within the window 1364 in manifold 1312. Cam surface 1368 of plug 1316 closes sleeve limit switch 1318 as plug 1316 rotates together with sleeve 1308. The sleeve 1308 and pump piston 1306 rotate as a unit with no relative axial motion. During this rotation the side hole 1358 of the sleeve 1308 moves between the reservoir port 1354 and the cannula port 1356.

Figure 29A:
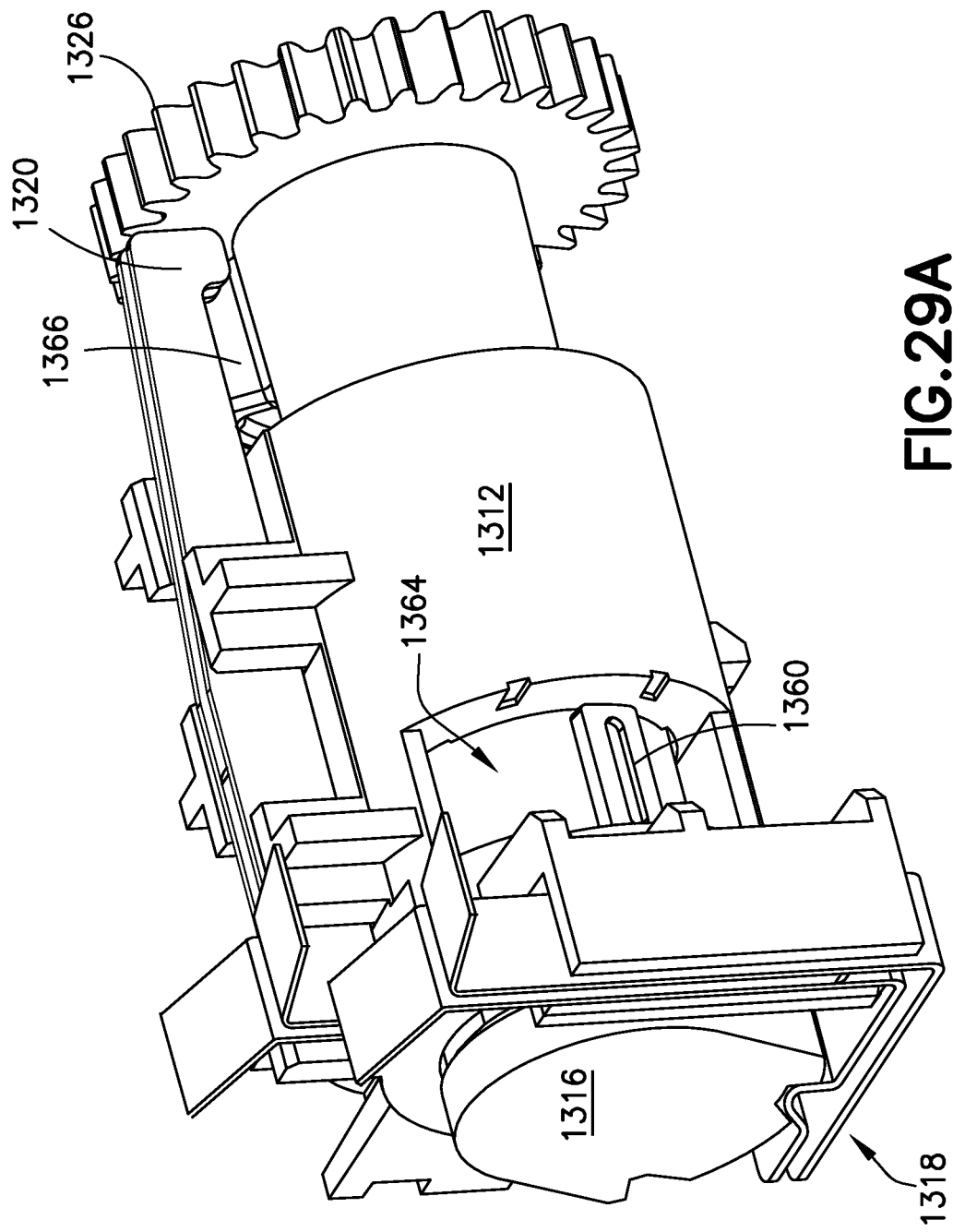

FIGS. 29A and 29B show the metering sub-system in an intake rotational stop position. In this position, the side hole 1358 of sleeve 1308 is aligned with the cannula port 1356, the pump volume 1352 is expanded, and the reservoir port 1354 is blocked. Cam 1366 of output gear 1326 engages rotational limit switch 1320 to signal that rotation is complete. Motor 1302 stops to reverse direction. Sleeve limit switch 1318 is open.

Figure 30A:
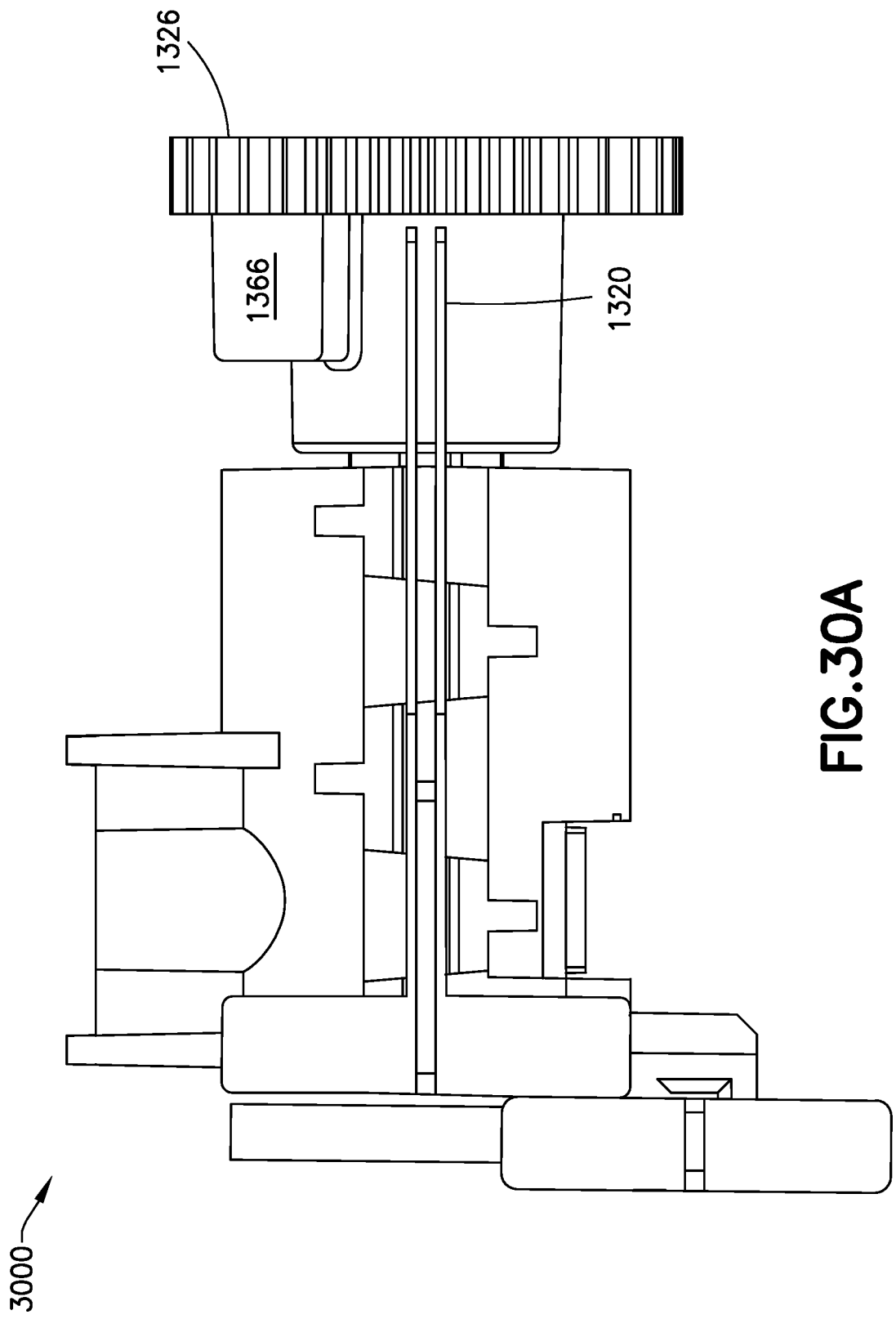
Figure 30B:
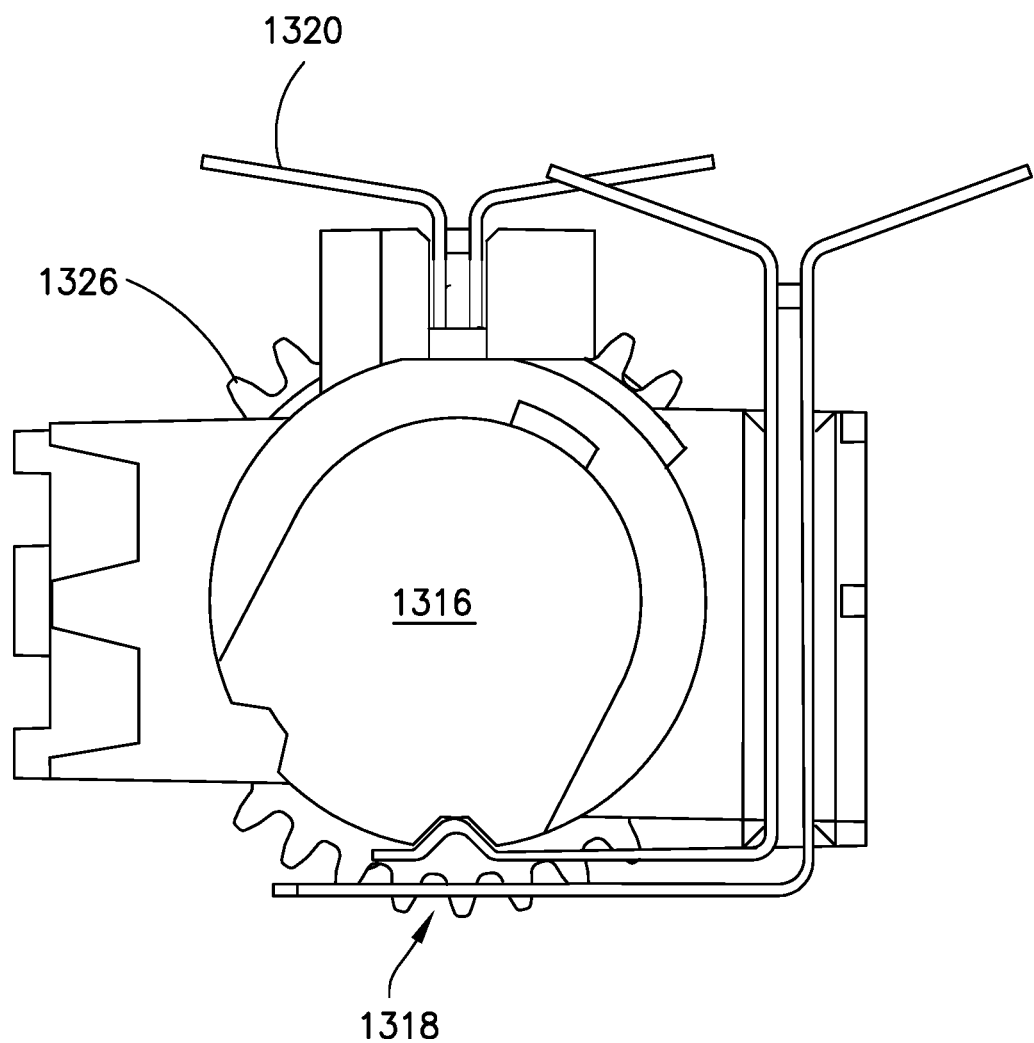

FIGS. 30A-30C show the metering sub-system after a pump cycle is complete. The output gear cam 1366 is jogged off of the rotational switch 1320 and ready to start another cycle.

Figure 31A:
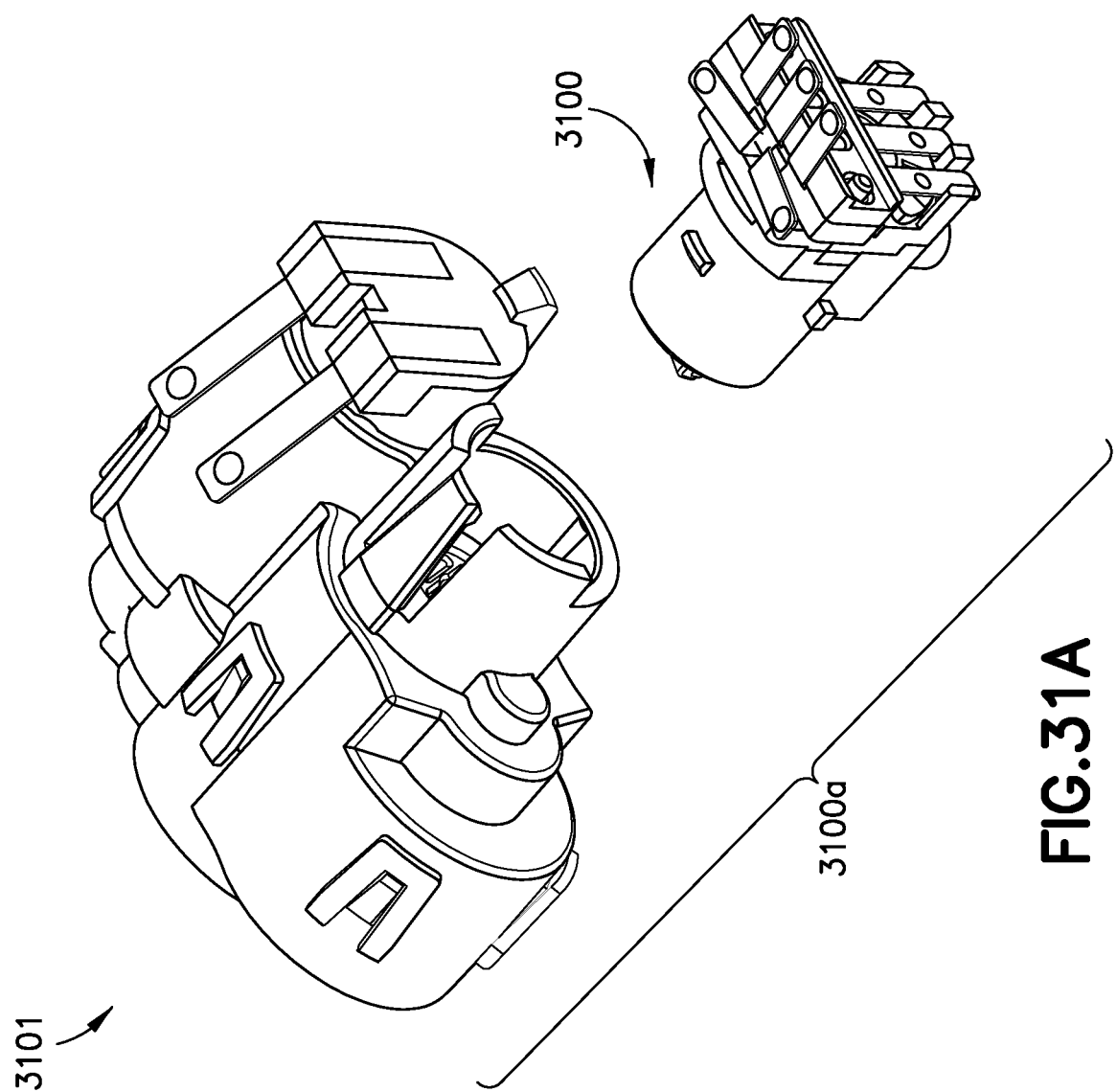
FIGS. 31A, 31B and 31C show multiple views of the motor and gearbox assembly as well as a modified pump assembly of an illustrative embodiment of a metering assembly in accordance with the present invention.
Figure 31B:
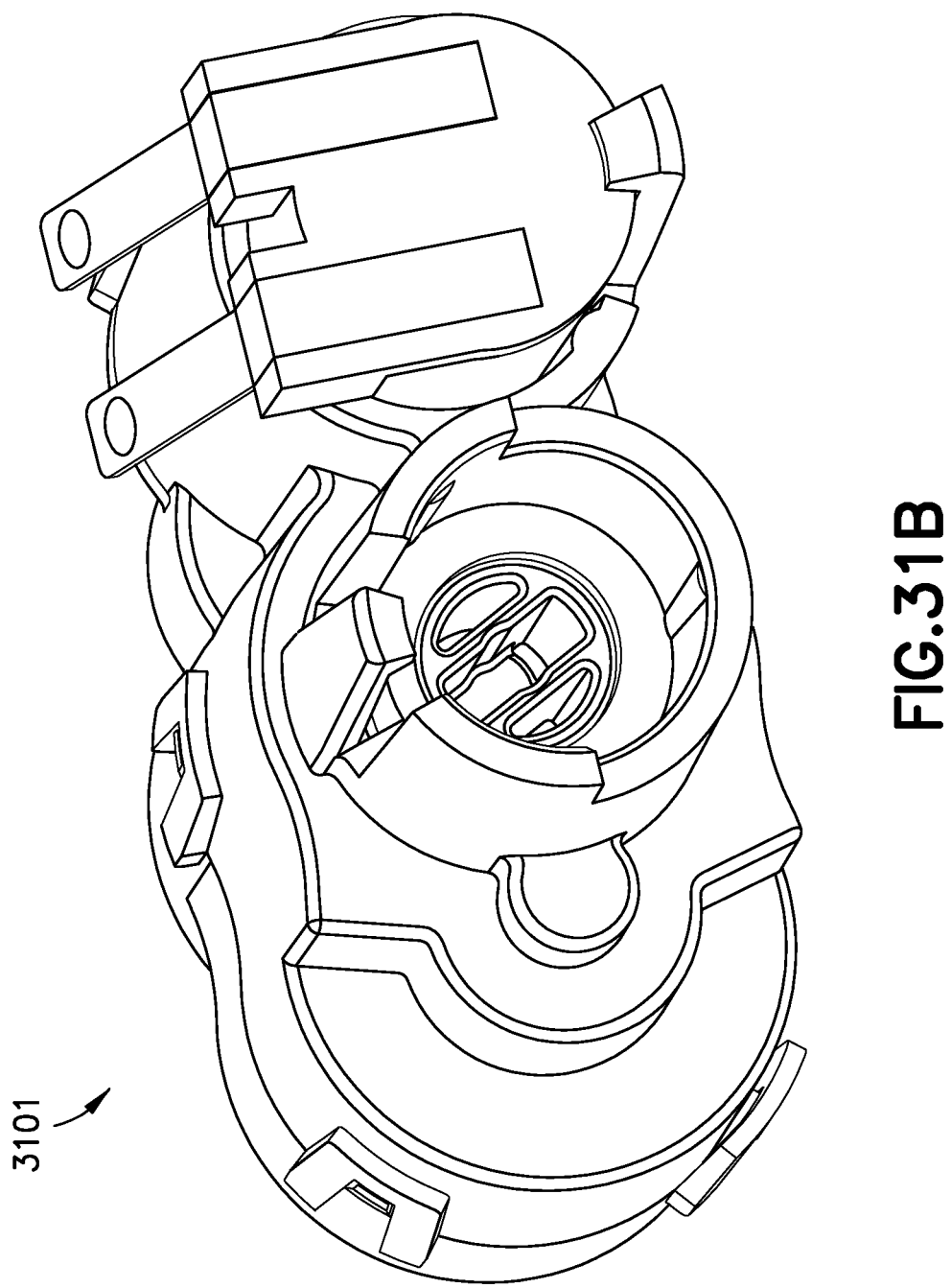
Figure 31C:
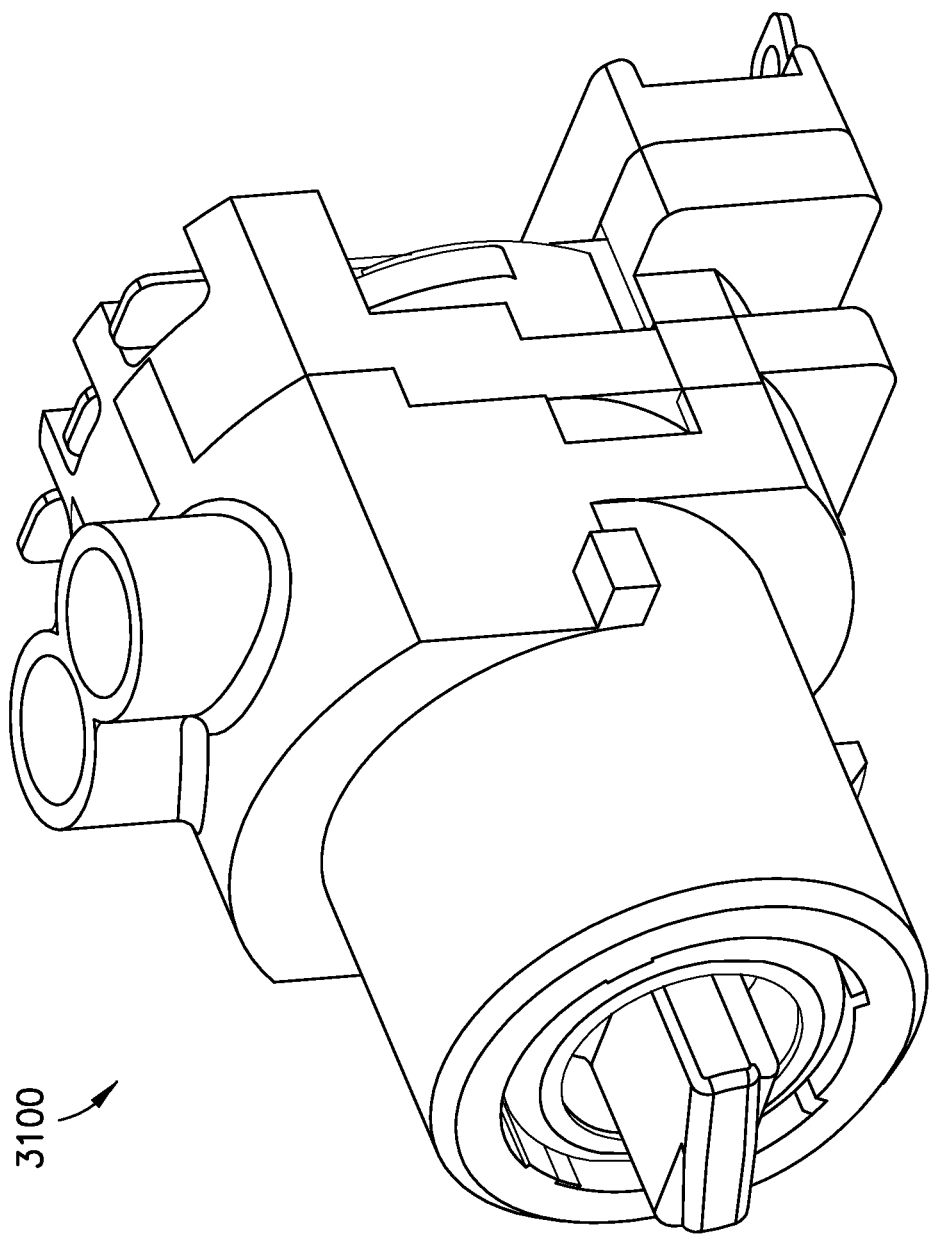

FIGS. 31A-31C illustrate another metering system 3100a according to an exemplary embodiment of the present invention. FIG. 31A shows the motor and gearbox assembly 3101 as well as a modified pump assembly 3100. The motor and gearbox assembly 3101 is substantially similar to the motor and gearbox assembly illustrated and described above in connection with FIGS. 13-30C.

Figure 32:
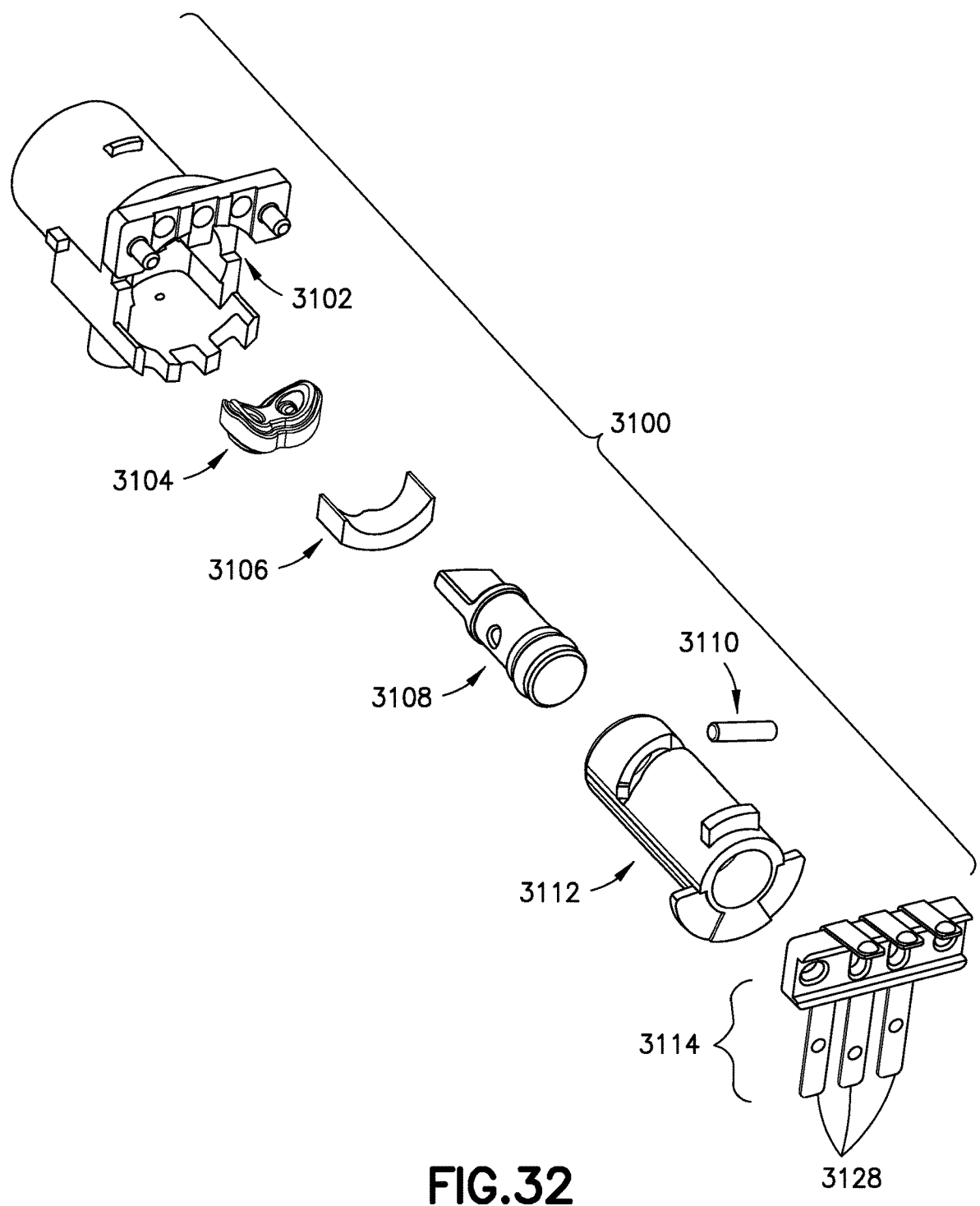
FIG. 32 shows an exploded view of a pump assembly of an illustrative embodiment of a metering assembly in accordance with the present invention.

FIG. 32 is an exploded view of the pump assembly 3100. The pump assembly 3100 includes a pump manifold 3102, a port seal 3104, a seal retainer 3106, a piston 3108 which rotates ±196° and translates axially ±0.038", a coupling pin 3110, a sleeve 3112 with conductive pads, and a sleeve rotational limit switch 3114 having flexure arms 3128. The sleeve 3112 with conductive pads rotates ±56° as illustrated.

The pump assembly 3100 includes three flexure arms 3128 that operate as a rotational travel limit switch 3114. The rotational travel limit switch 3114 will be described in further detail below. The rotational travel limit switch 3114 senses the position of the sleeve 3112 directly, rather than sensing the position of the output gear. This allows for more precise angular alignment of the sleeve 3112 with respect to the manifold 3102 and cannula port.

Figure 33A:
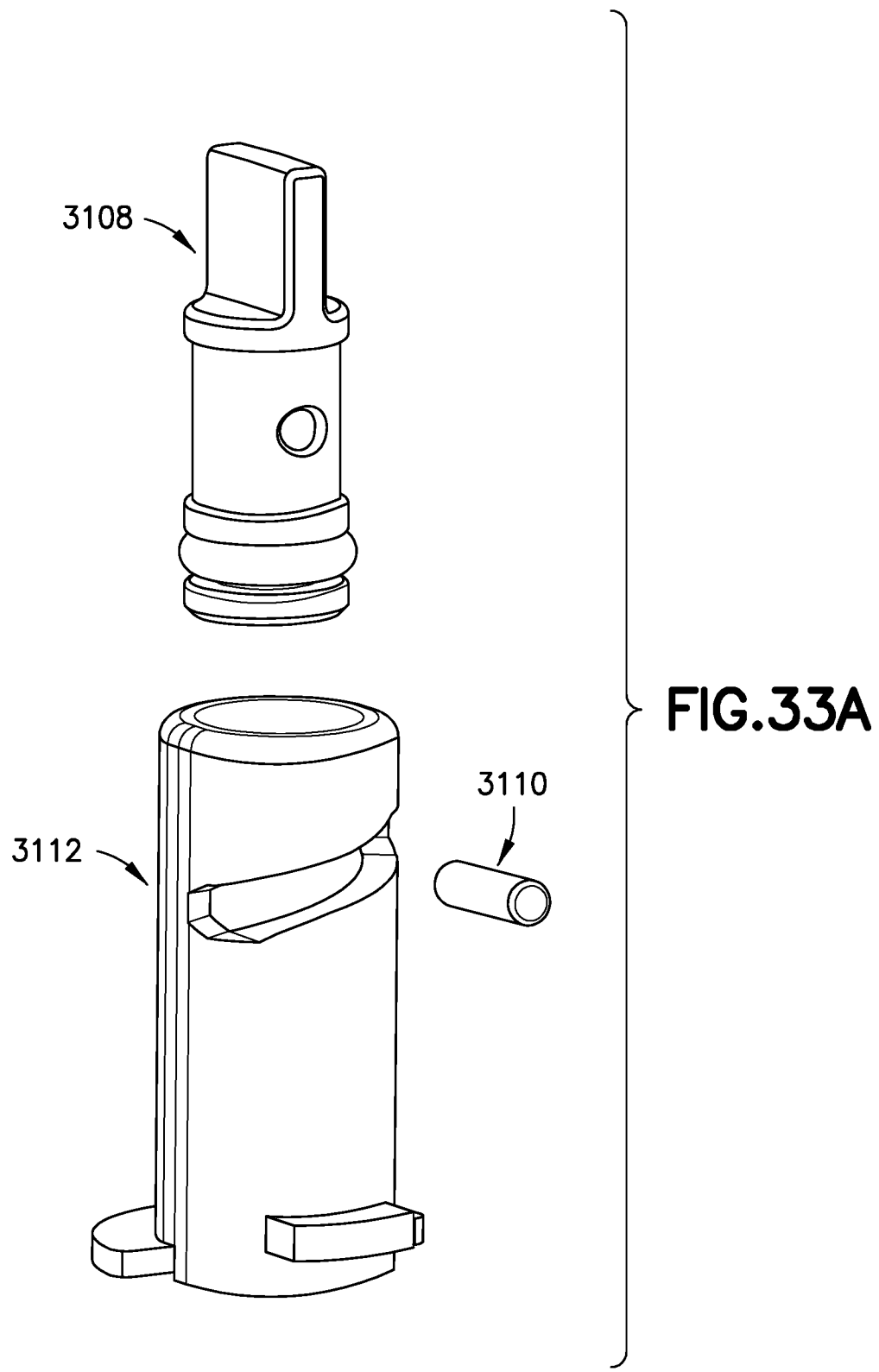
FIGS. 33A and 33B show an assembly of a piston into a sleeve of an illustrative embodiment of a patch pump in accordance with the present invention.
Figure 33B:
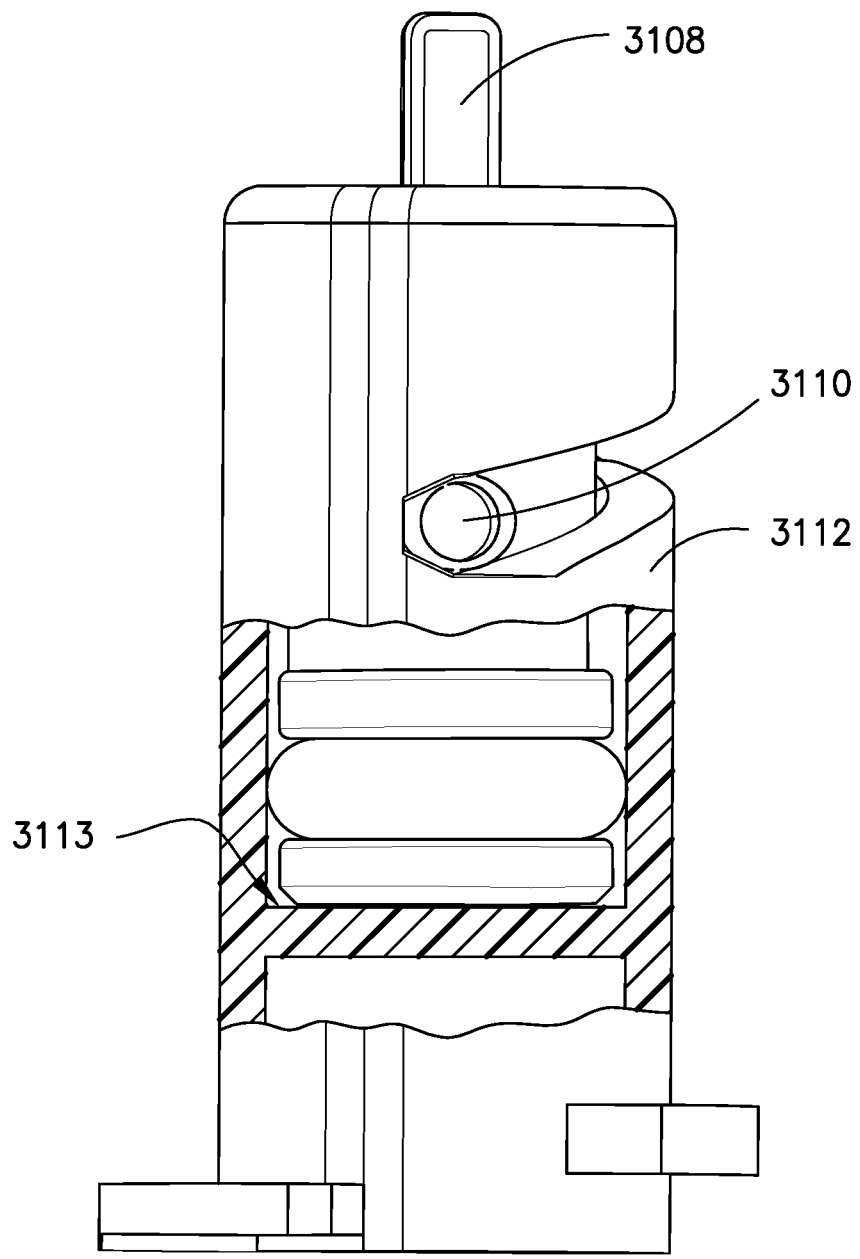
Figure 34B:
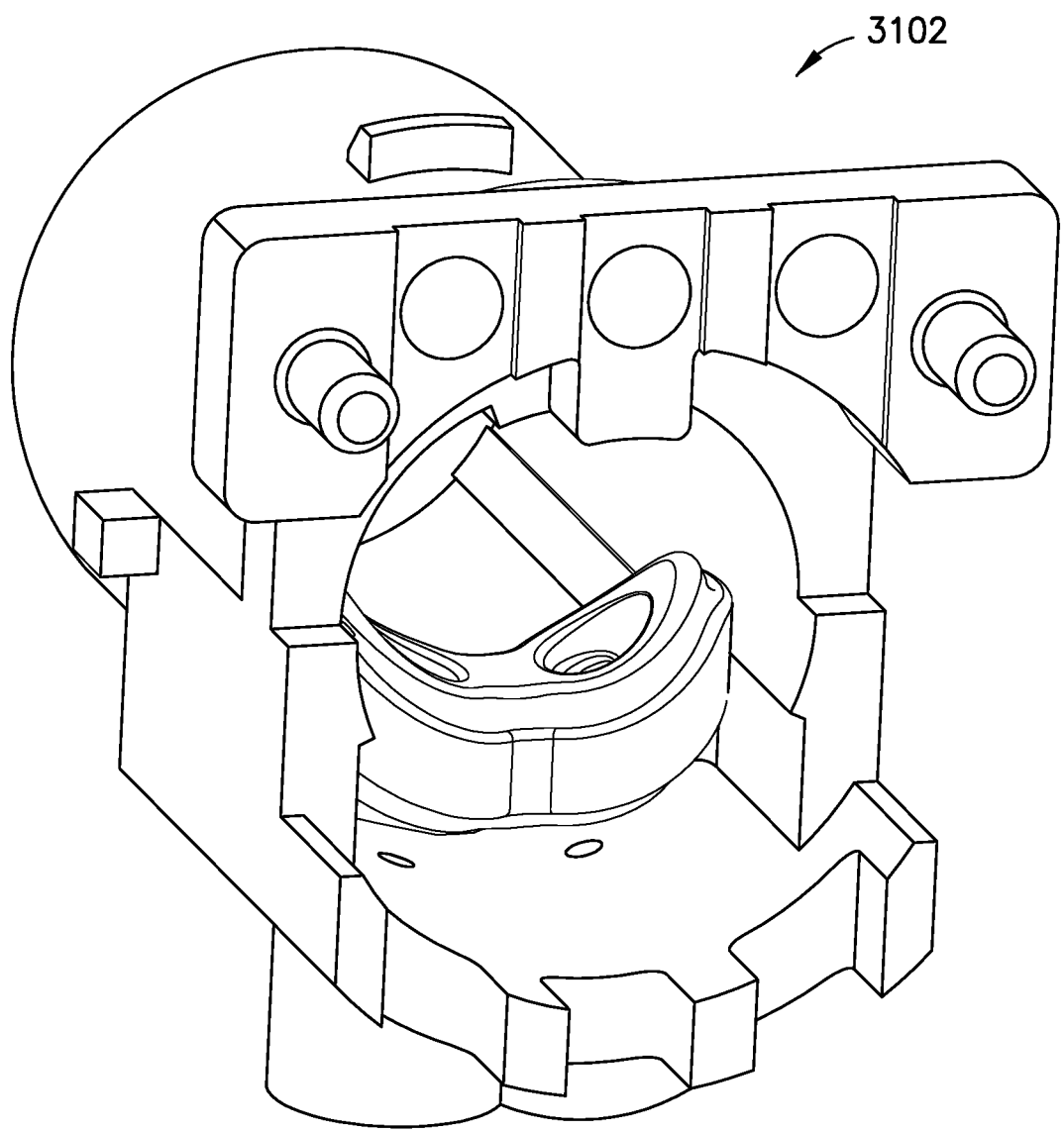
Figure 34C:
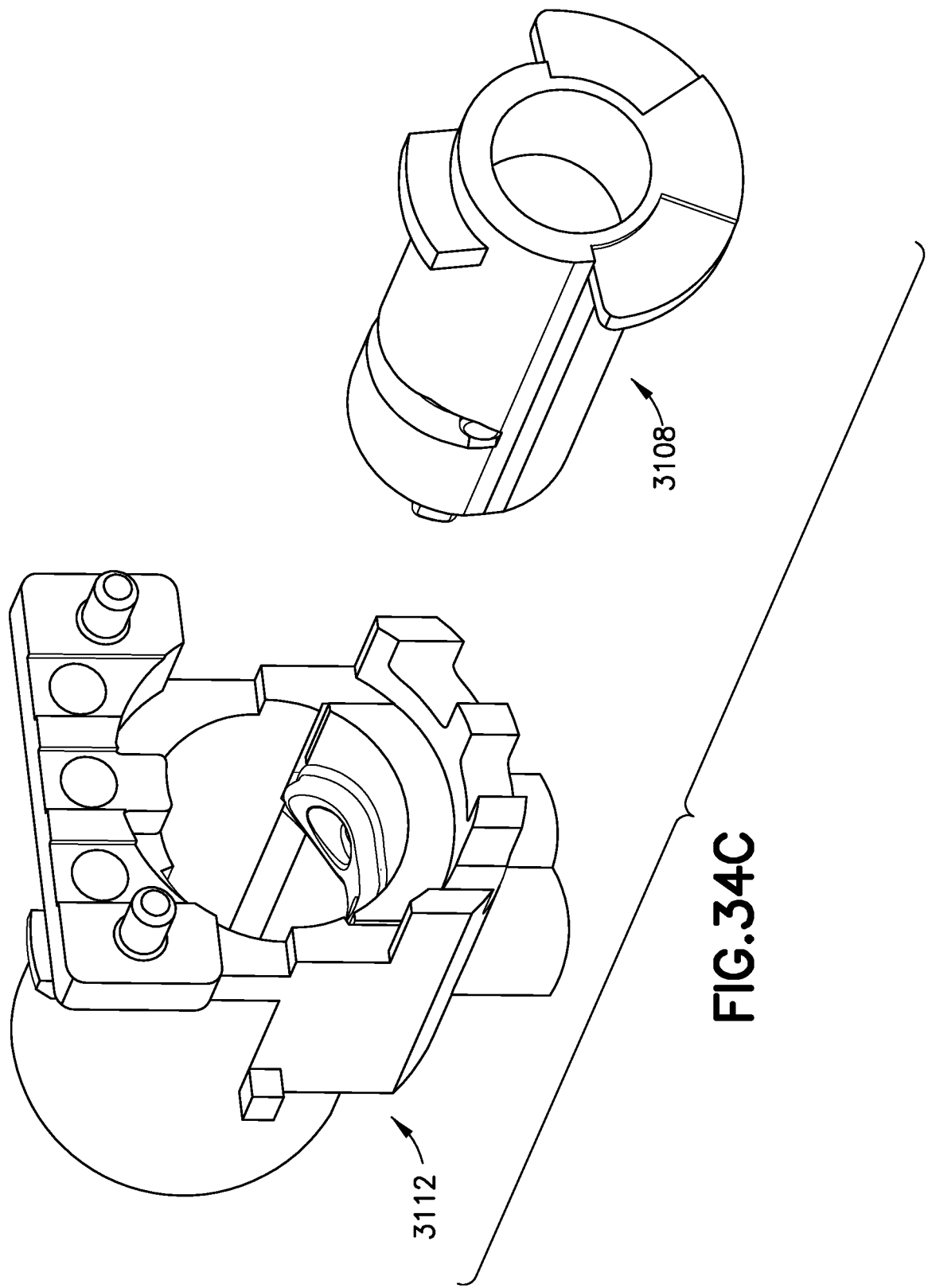
Figure 34D:
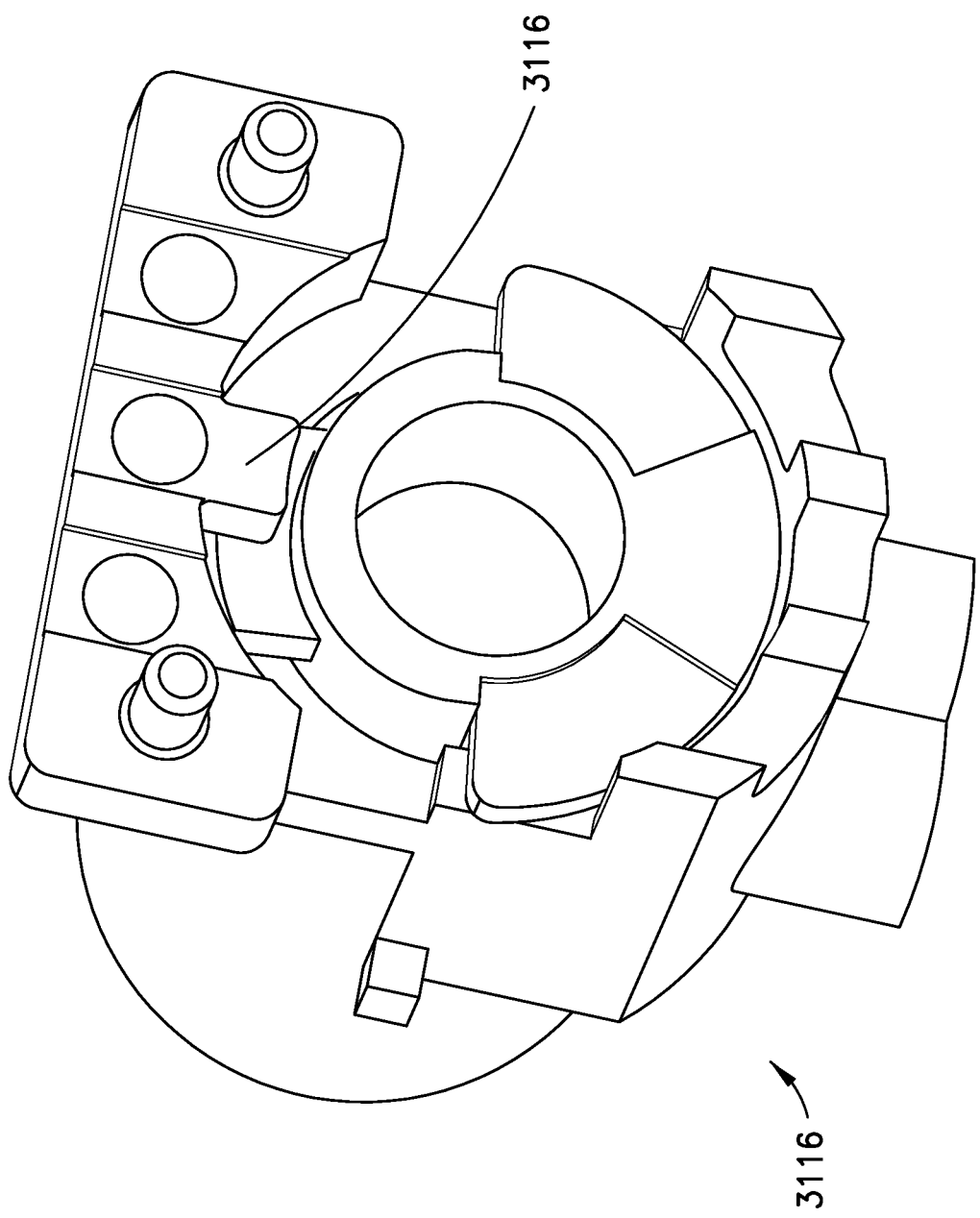

FIGS. 33A-33B illustrates the assembly of the piston 3108 into the sleeve 3112. In this embodiment an internal wall 3113 in the sleeve 3112 forms the end face of the pump chamber. Features on the piston sleeve are designed with tolerances to minimize the gap between the end face of the piston 3108 and the face of the internal wall 3113 of the sleeve.

FIGS. 34A-34E illustrates the assembly of sleeve 3108 into the manifold 3102. As illustrated the port seal 3104, the seal retainer 3106, and the sleeve 3112 are inserted into the manifold 3102. A small side hole 3115 (See FIG. 34E) on the sleeve 3112 rotationally shuttles back and forth between a reservoir port and a cannula port, which are preferably 56 degrees apart. The sleeve 3112 is inserted past a retention tab 3116 (See FIG. 34D) in the manifold 3102 and is then rotated into position to prevent axial travel. Because this embodiment prevents or minimizes axial movement of the plug, occlusion sensing by axial movement of the plug is typically not provided.

Figure 35:
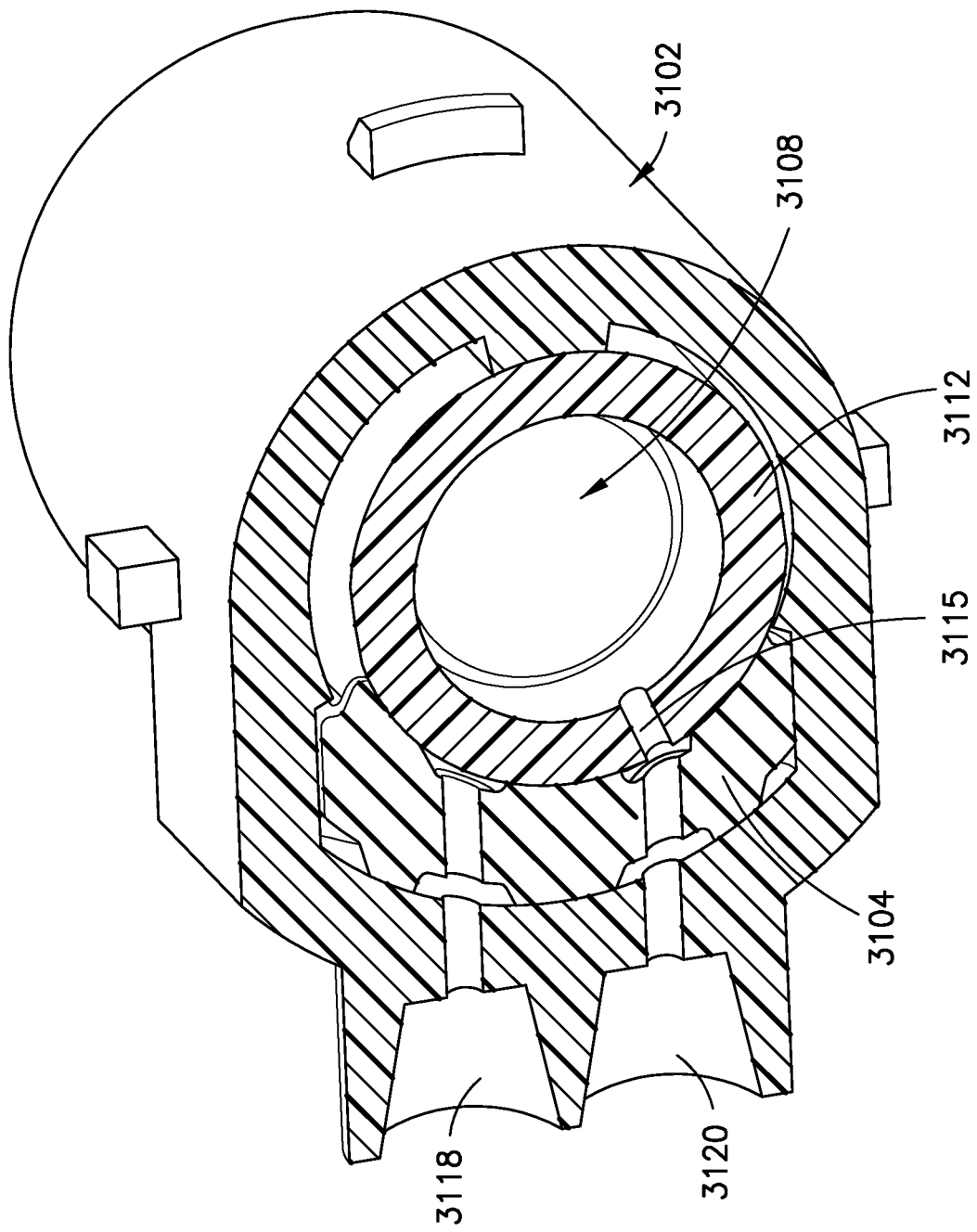
FIG. 35 shows a cross section of a sleeve and manifold assembly of an illustrative embodiment of a patch pump in accordance with the present invention.

FIG. 35 illustrates a cross section of the sleeve 3112 and manifold 3102 assembly taken through the port seal 3104 and through the axes of side ports to the manifold 3102. The side ports to the manifold 3102 include the cannula port 3118 and reservoir port 3120. The port seal 3104 is a face seal, which is compressed between the sleeve 3112 outer diameter and a recessed pocket in the manifold 3102.

Figure 36B:
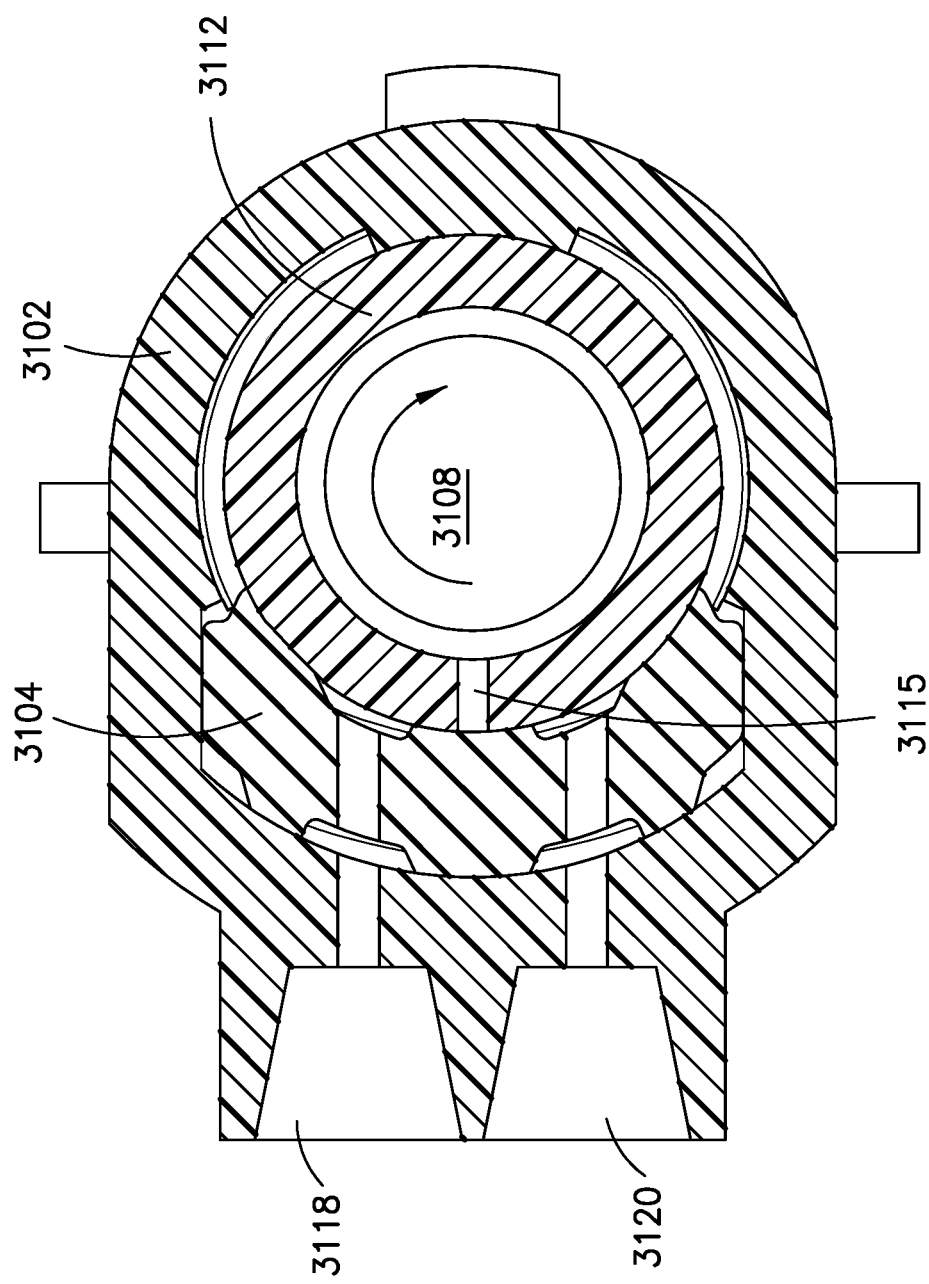
Figure 37A:
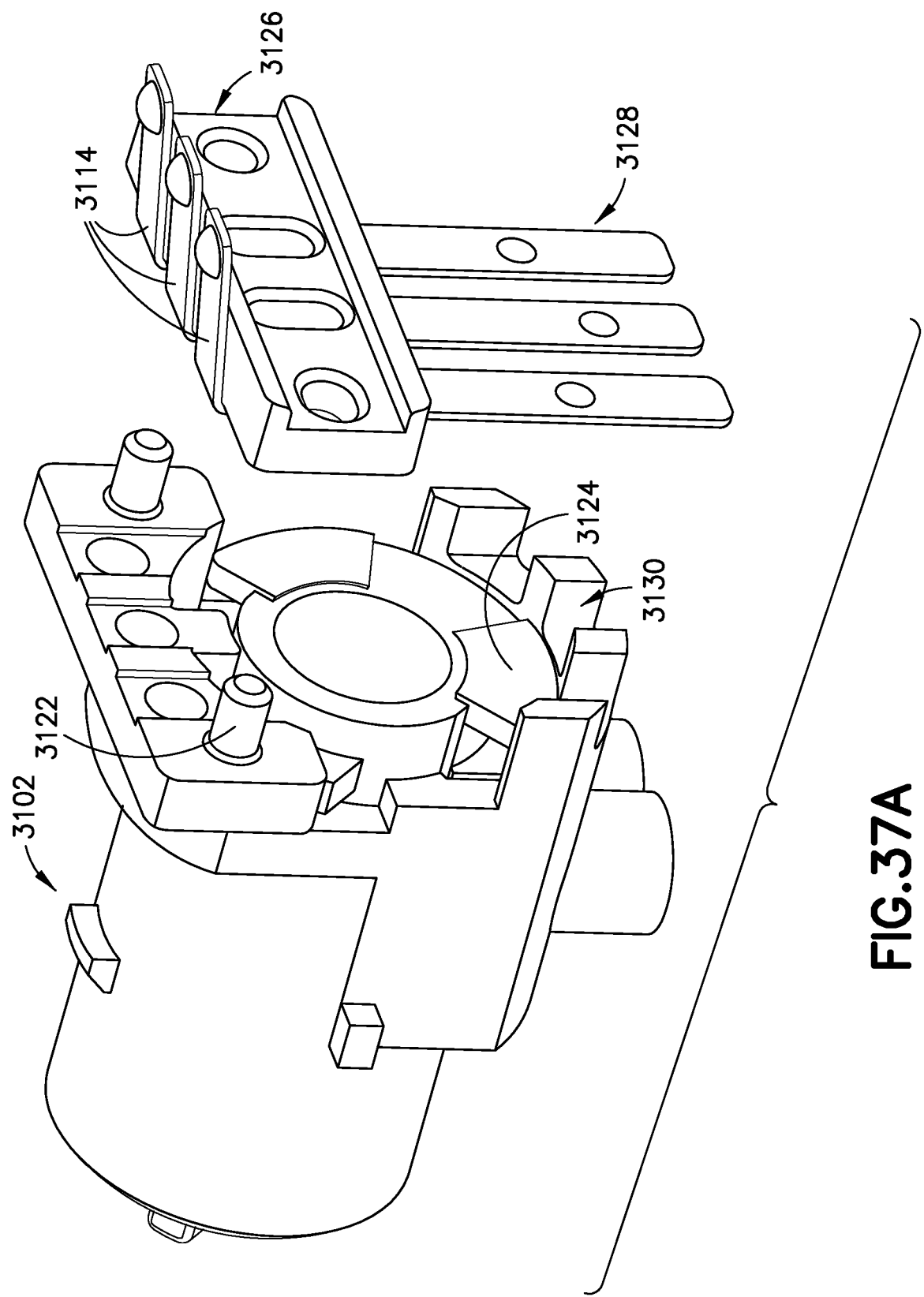

FIGS. 36A-36C are cross sections through the axes of the side ports as the sleeve 3112 rotates from the reservoir port 3120 to the cannula port 3118, to illustrate the valve state change. In the initial position shown in FIG. 36A, the sleeve side hole 3115 is open to the reservoir port 3120. In this position the cannula port 3118 is blocked. In the intermediate position shown in FIG. 36B, the sleeve side hole 3115 is blocked by the port seal 3104 during the transition. In the final position shown in FIG. 36C, the sleeve side hole 3115 is open to the cannula port 3118. In this position the reservoir port 3120 is blocked.

FIGS. 37a-37D illustrates the operation for the sleeve rotational limit switch 3114. A three contact switch design allows the patch system to distinguish between the two rotational limits via switch input signals rather than through tracking the sleeve's angular orientation via software. Manifold 3102 preferably includes manifold mounting posts 3122. The switch contacts 3114 are bonded to the posts 3122 with adhesive, ultrasonic welding, heat stake, or any other suitable bonding method. Sleeve 3112 includes conductive pads 3124 on the end of sleeve 3112. These may be printed or over-molded metal inserts, or may be provided by any other suitable means. Sleeve rotational limit switch 3114 includes a plastic over-mold 3126 for spacing and mounting features for the flexures. Sleeve rotational limit switch 3114 also includes three metal flexures 3128. Manifold 3102 is provided with alignment slots 3130, which receive the flexures 3128. In a first position, shown in FIG. 37B, the side hole 3115 on the sleeve 3112 is aligned to the cannula port 3118. In this position, a conductive pad 3124 on the sleeve 3112 bridges the center and right contacts 3128a, 3128b. In the middle position, shown in FIG. 37C, the side hole 3115 on sleeve 3112 is midway between ports 3118 and 3120. In this position, both sides of the switch 3114 are open. In the final position, shown in FIG. 37D, the side hole 3115 on sleeve 3112 is aligned to reservoir port 3120. In this position, conductive pad 3124 on the sleeve 3112 bridges the center and left contacts, 3128b, 3128c.

The pump described above has a modified operating sequence. The operating sequence is substantially the same as that described above, with the exception that the 20° back jog is no longer required. The back jog is not required with the three contact switch design described above and a complete pump cycle consists of the following four segments. First, there is an approximately 140° pump discharge, which is counterclockwise when viewing from the pump toward the gearbox. Second, there is a 56° valve state change, which is also counterclockwise. Third, there is an 140° pump intake, which is clockwise. Fourth, there is a 56° valve state change clockwise. The total pump cycle requires 196 degrees of output gear rotation in each direction.

Figure 38B:
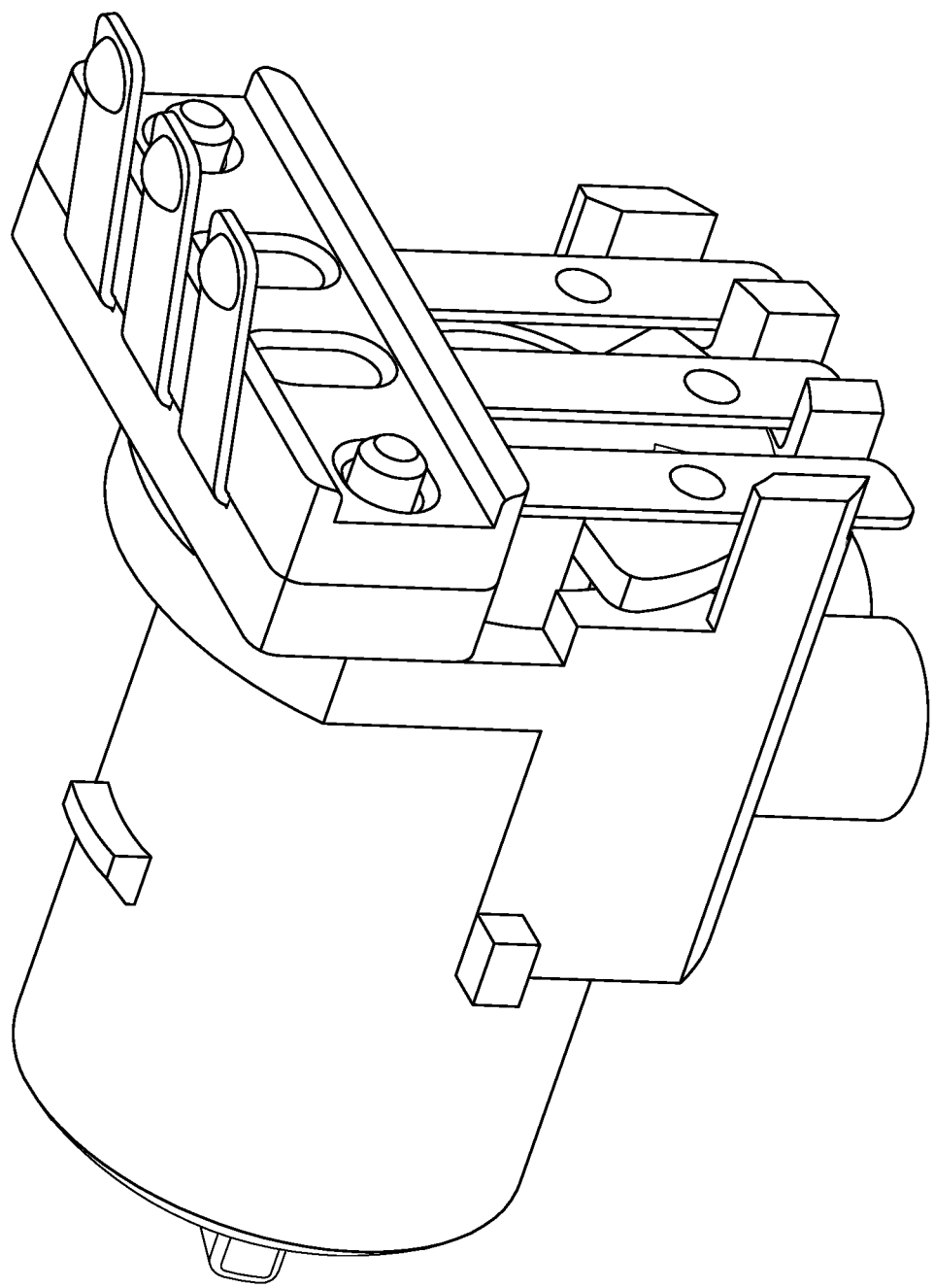

FIGS. 38A and 38B illustrate an exploded view of another version of the pump assembly with elastomeric port and piston seals over-molded onto the manifold and pump piston respectively. This version of the pump functions in a manner substantially identical to the one described above, but has fewer discrete components and is easier to assemble. Over-molding seals directly onto the manifold and piston reduces the number of dimensions contributing to seal compression, allowing for tighter control and less variability in seal performance.

Figure 39A:
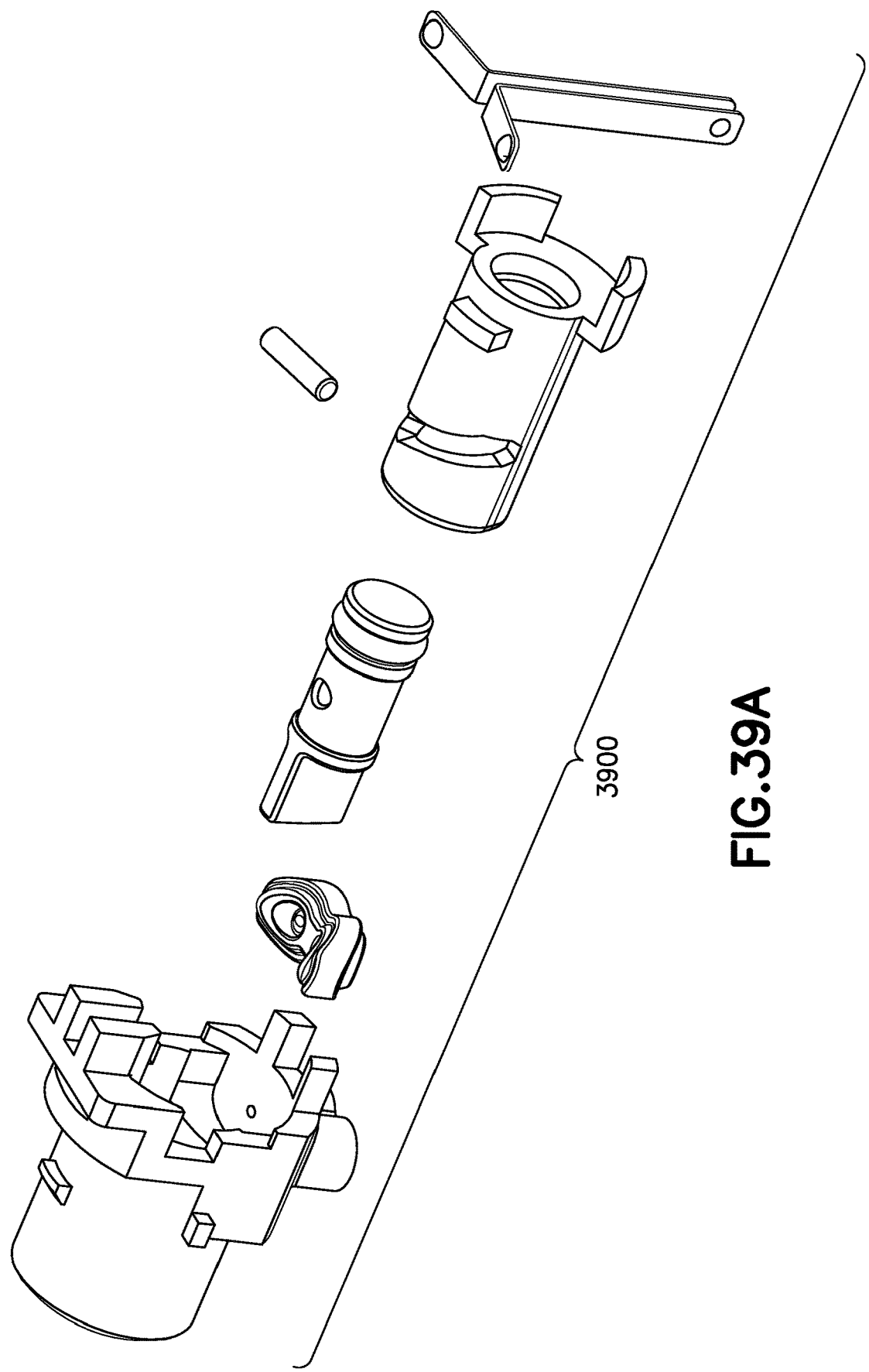

FIG. 39A illustrates an exploded view of a pump assembly 3900 with an alternative rotational limit switch design. This version of the pump assembly includes a two contact design for the sleeve rotational limit switch. With this design, the pump would properly jog backwards at the end of a pump cycle so that the contact switch 3902 would be open in the rest state. As illustrated in FIG. 39B, in a first position the side hole 3115 on the sleeve is aligned to the cannula port. In this position, a first rib 3904 on sleeve forces the contracts closed. In a mid-position shown in FIG. 39C, the side hole 3115 on sleeve is midway between ports, and neither rib 3904, 3906 touches the contact switch 3902 so it is open. In a third position shown in FIG. 39D, the side hole 3115 on the sleeve is aligned to the reservoir port. In this position, a second rib 3906 on sleeve again forces the contact switch 3902 closed.

Figure 40:
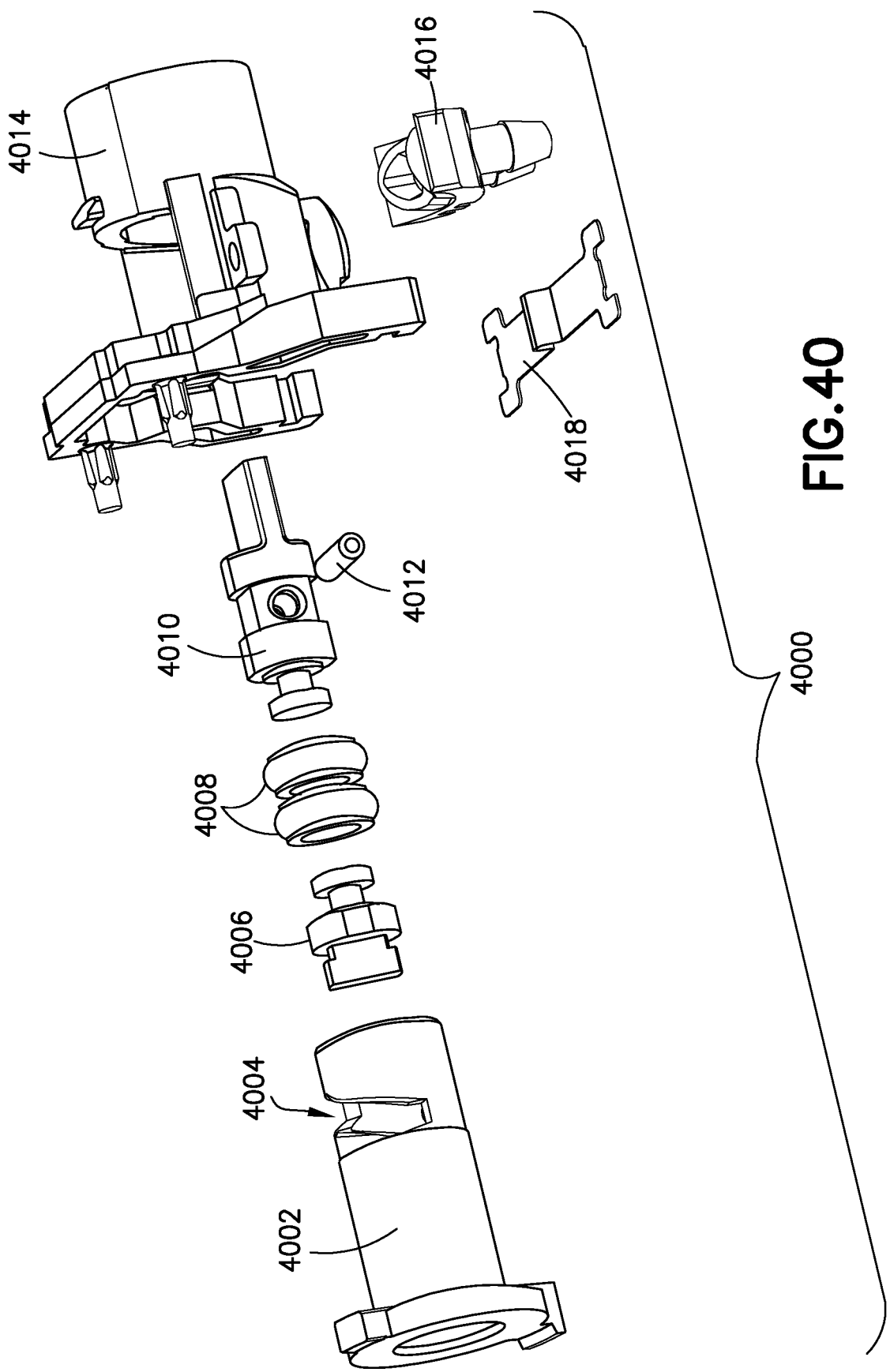
FIG. 40 shows an exploded view of an illustrative embodiment of a metering assembly in accordance with the present invention.
Figure 41:
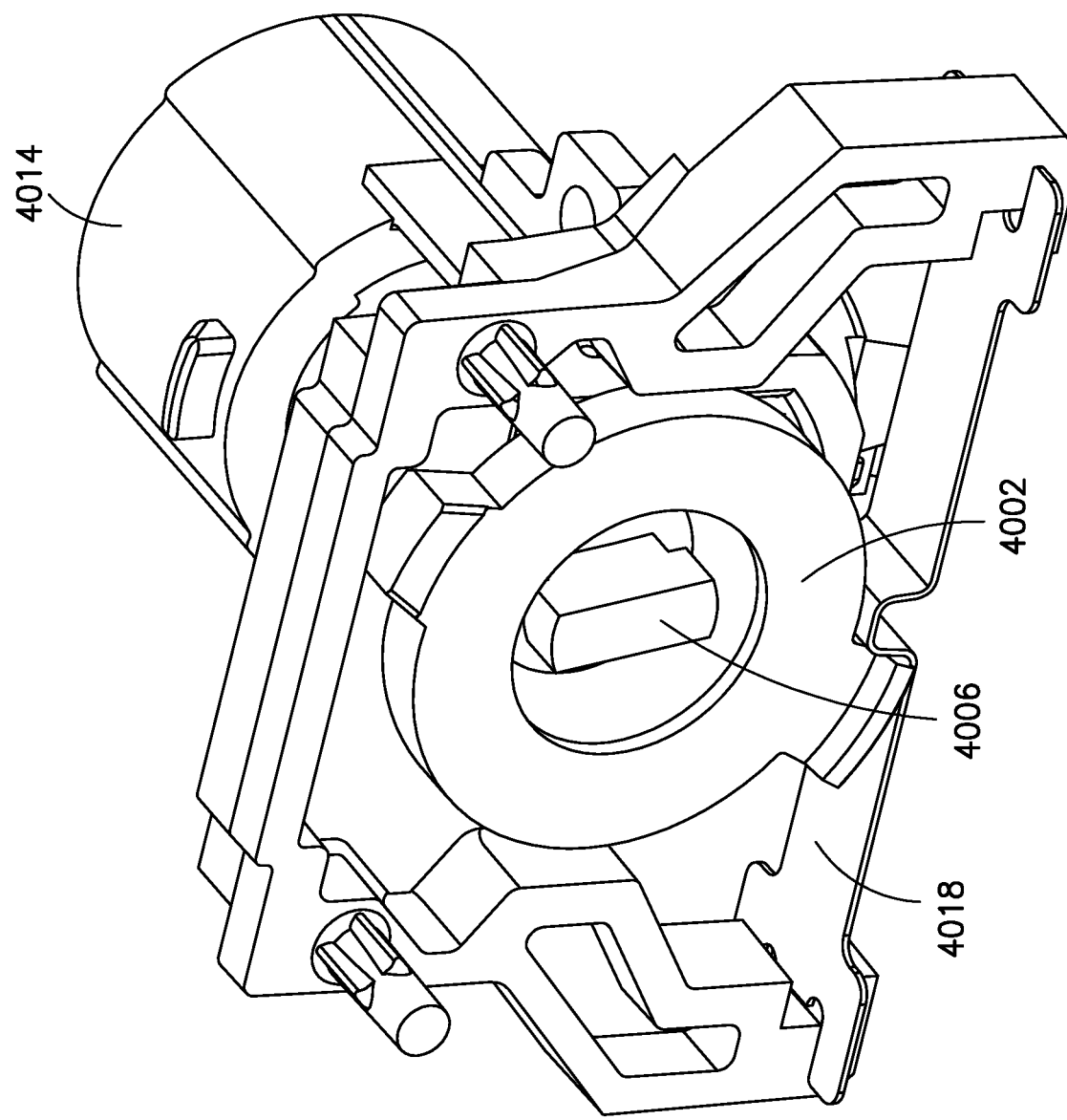
FIG. 41 shows an assembled view of metering assembly of FIG. 40.
Figure 42:
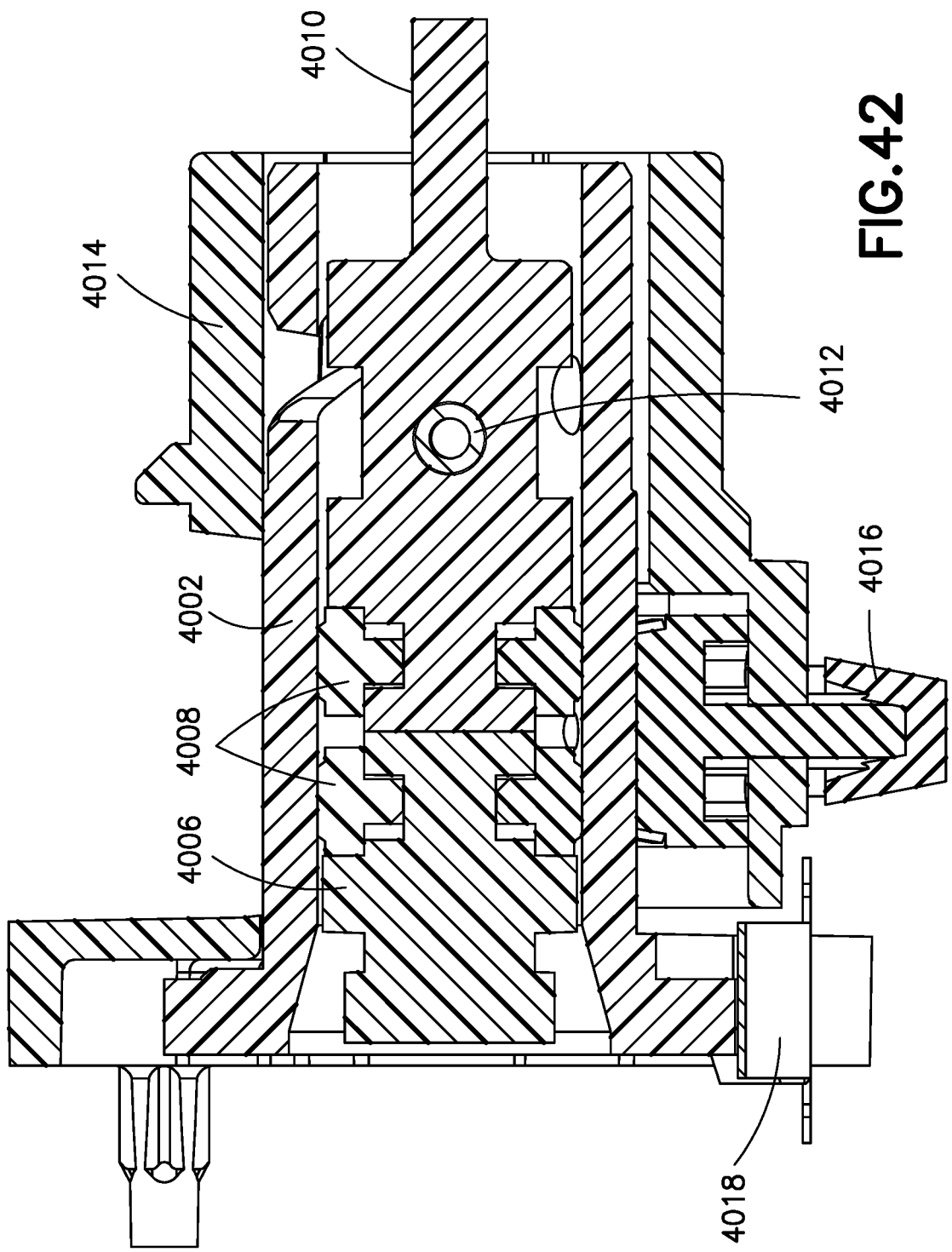
FIG. 42 shows a cross-section of metering assembly of FIG. 40.

FIG. 40 is an exploded view of another exemplary embodiment of a metering assembly 4000. This embodiment shares substantial similarities with the embodiments described above so the following description focuses on the differences. Metering assembly 4000 includes a sleeve 4002 having a helical groove 4004, a plug 4006, seals 4008, plunger 4010, coupling pin 4012, manifold 4014, port seal 4016, and flexible interlock 4018. FIG. 41 illustrates the metering assembly in assembled form. Seals 4008 are preferably formed of an elastomeric material, and are unitary in construction. One seal 4008 is mounted onto plug 4006, and the other seal 4008 is mounted onto plunger 4010. Plug 4006 is preferably fixed into sleeve 4002 by gluing, heat sealing, or any other suitable means. An end face of the plug forms one surface of the pump volume. Plunger 4010 is inserted into sleeve 4002, and coupling pin 4012 is press fit into the plunger 4010 and extends into helical groove 4004 to provide axial translation of the plunger 4010 as it is rotated by the motor (not shown). An end face of the plunger 4010 forms an opposing surface of the pump volume. Port seal 4016 is preferably a single molded piece of elastomeric material. This embodiment reduced the number of parts, and improves manufacturability. FIG. 42 is a cross section of the assembled metering assembly.

Figure 43A:
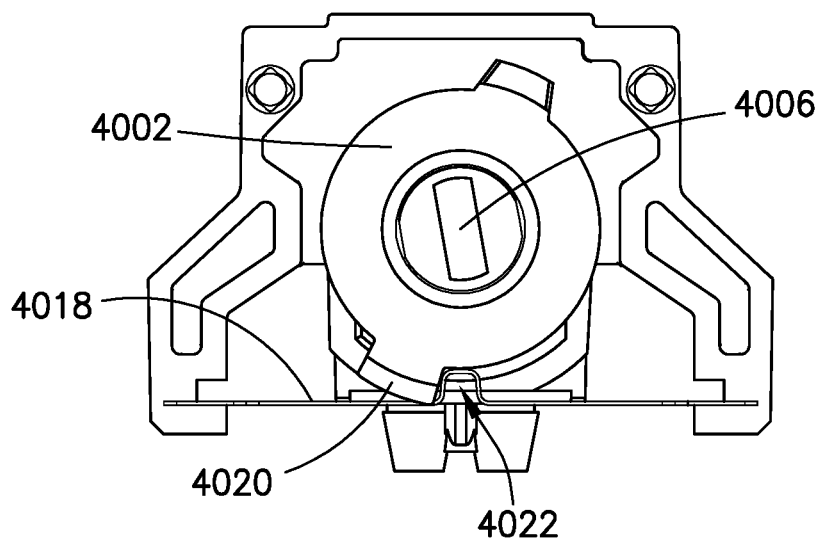
FIGS. 43A, 43B and 43C show interaction of an interlock with a sleeve of metering assembly of FIG. 40 in accordance with an illustrative embodiment of the present invention.
Figure 43B:
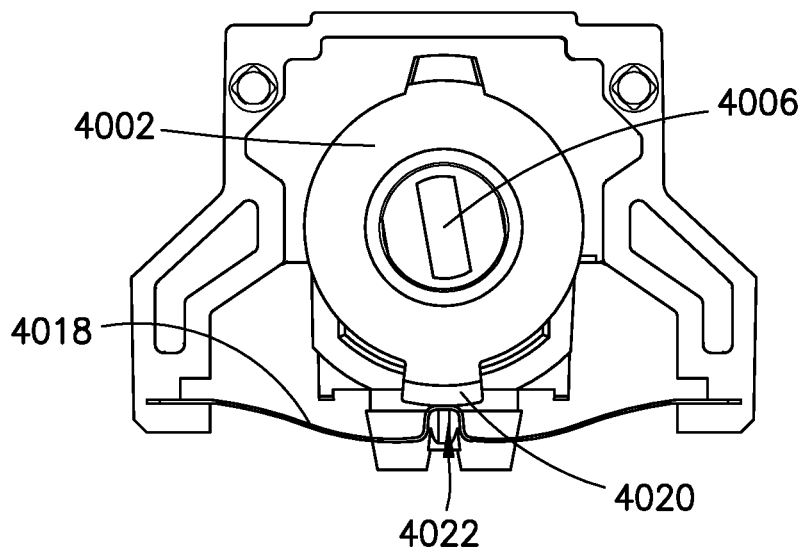
Figure 43C:
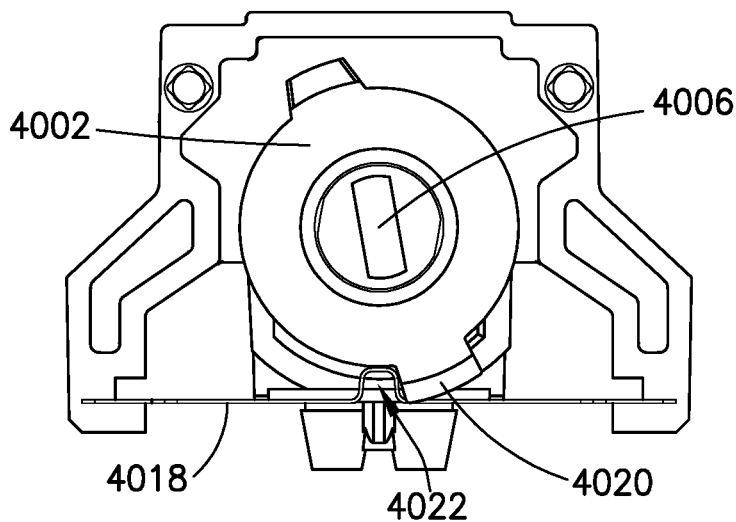

FIGS. 43A-43C illustrate the interaction of the interlock 4018 with the sleeve 4002. As shown in FIG. 41, interlock 4018 is mounted onto manifold 4014 at either end of interlock 4018. As shown in FIG. 43A, an end face of sleeve 4002 includes a detent 4020 that is adjacent to a bump 4022 of the interlock 4018 when the metering assembly is in a first position (side hole aligned with reservoir pump). Under certain conditions, such as back pressure, it is possible that friction between the piston 4010 and the sleeve 4008 is sufficient to cause the sleeve to rotate before the plunger 4010 and coupling pin 4012 reach either end of the helical groove 4004. This could result in an incomplete volume of liquid being pumped per stroke. In order to prevent this situation, interlock 4018 prevents sleeve 4002 from rotating until the torque passes a predetermined threshold. This ensures that piston 4010 fully rotates within sleeve 4008 until the coupling pin 4012 reaches the end of the helical groove 4004. Once the coupling pin hits the end of the helical groove 4004, further movement by the motor increases torque on the sleeve beyond the threshold, causing the interlock to flex and permit the detent 4020 to pass by the bump 4022. This is illustrated in FIG. 43B. At the completion of rotation of the sleeve 4008 such that the side hole is oriented with the cannula port, the detent 4020 moves past the bump 4022 in interlock 4018. This is illustrated in FIG. 43C.

Figure 44:
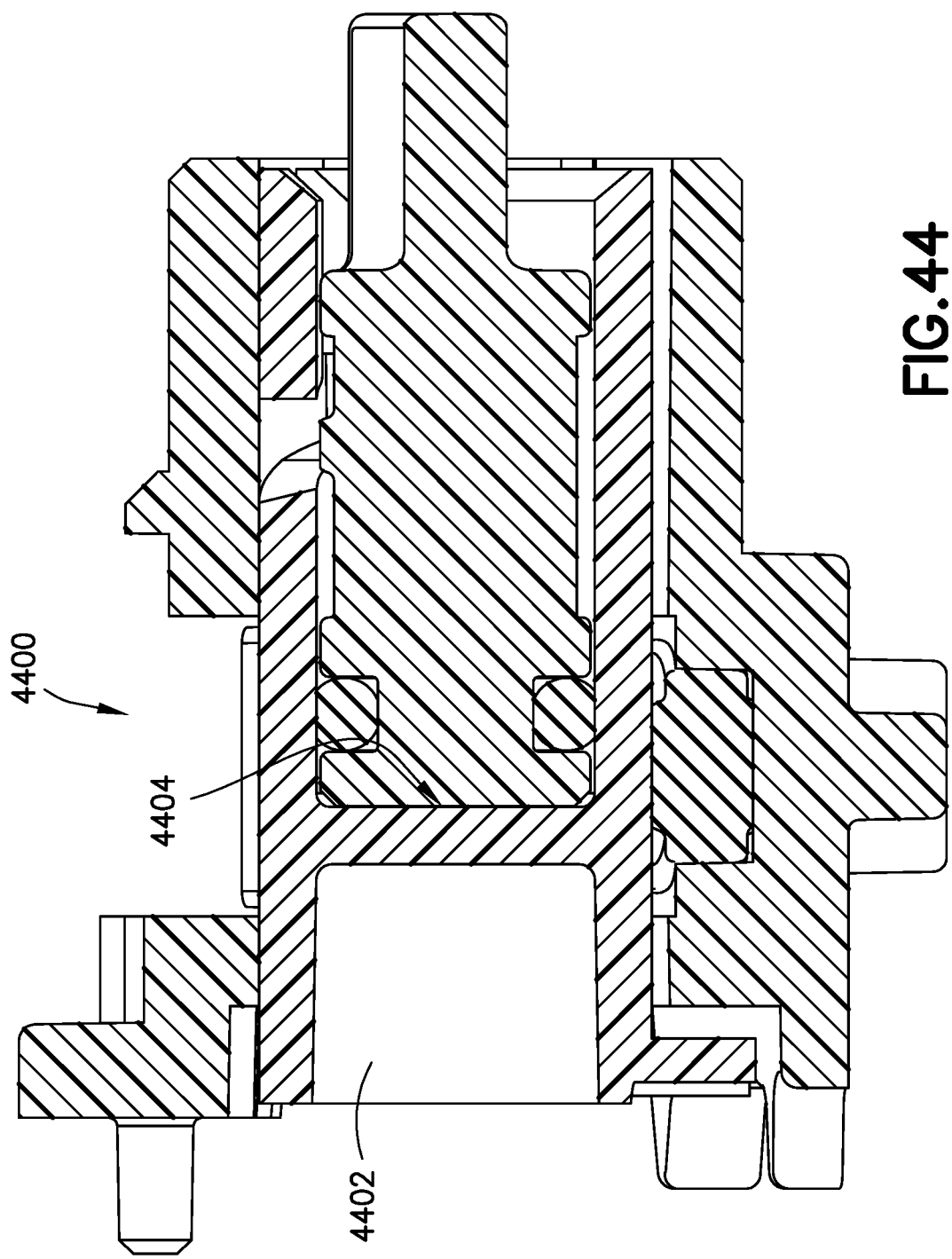
FIG. 44 shows a cross-section of another illustrative embodiment of a metering assembly in accordance with the present invention.

FIG. 44 illustrates a cross section of another exemplary embodiment of a metering system 4400. The metering system 4400 includes a modified sleeve 4402 that has a face 4404 forming one surface of the pump volume. This embodiment eliminates the need for a plug as in the previous embodiment, and simplifies manufacturing.

Figure 45:
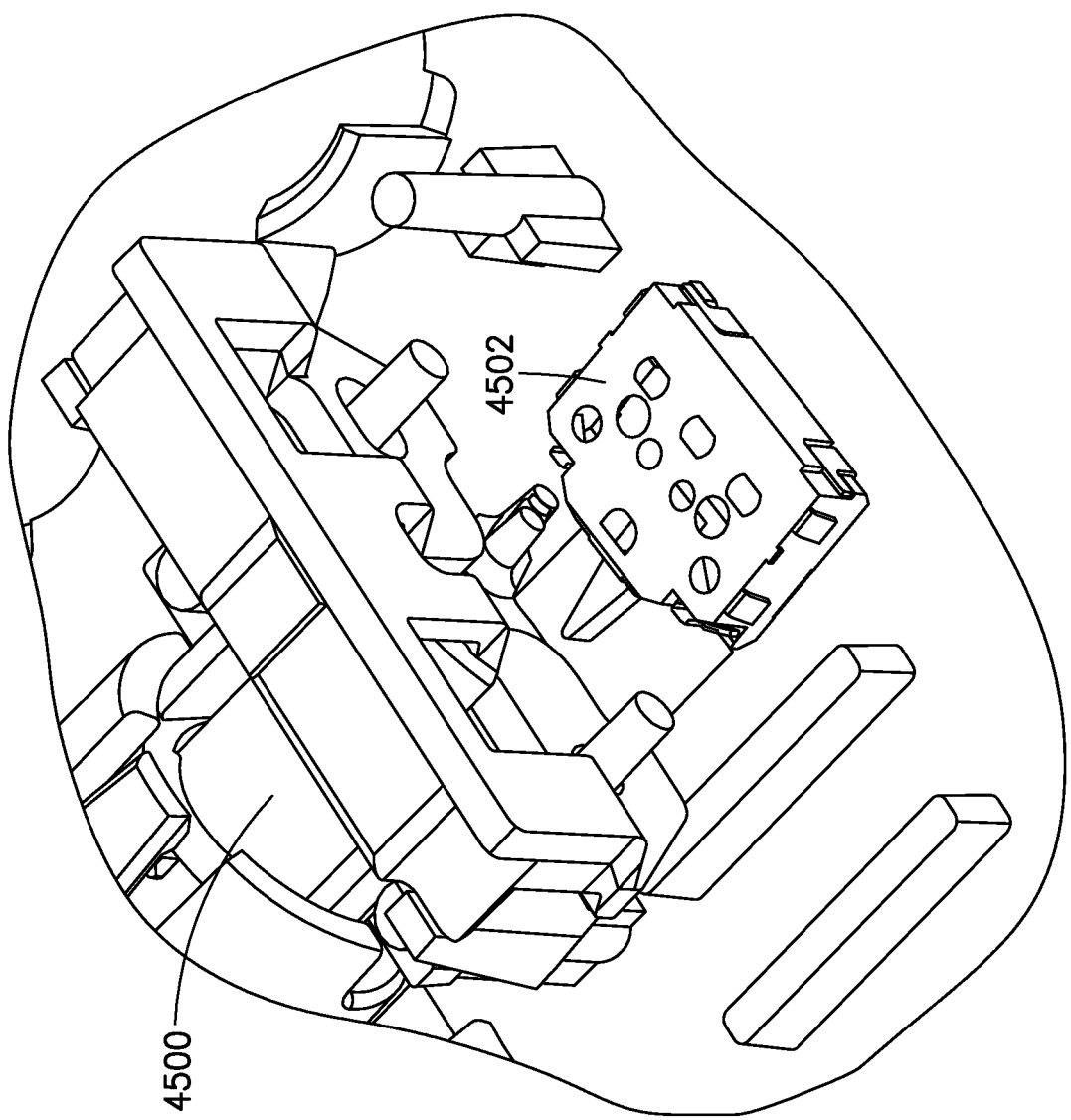
FIG. 45 is an isometric view of a limit switch and actuator arm useful in an alternate exemplary embodiment of the present invention.
Figure 46:
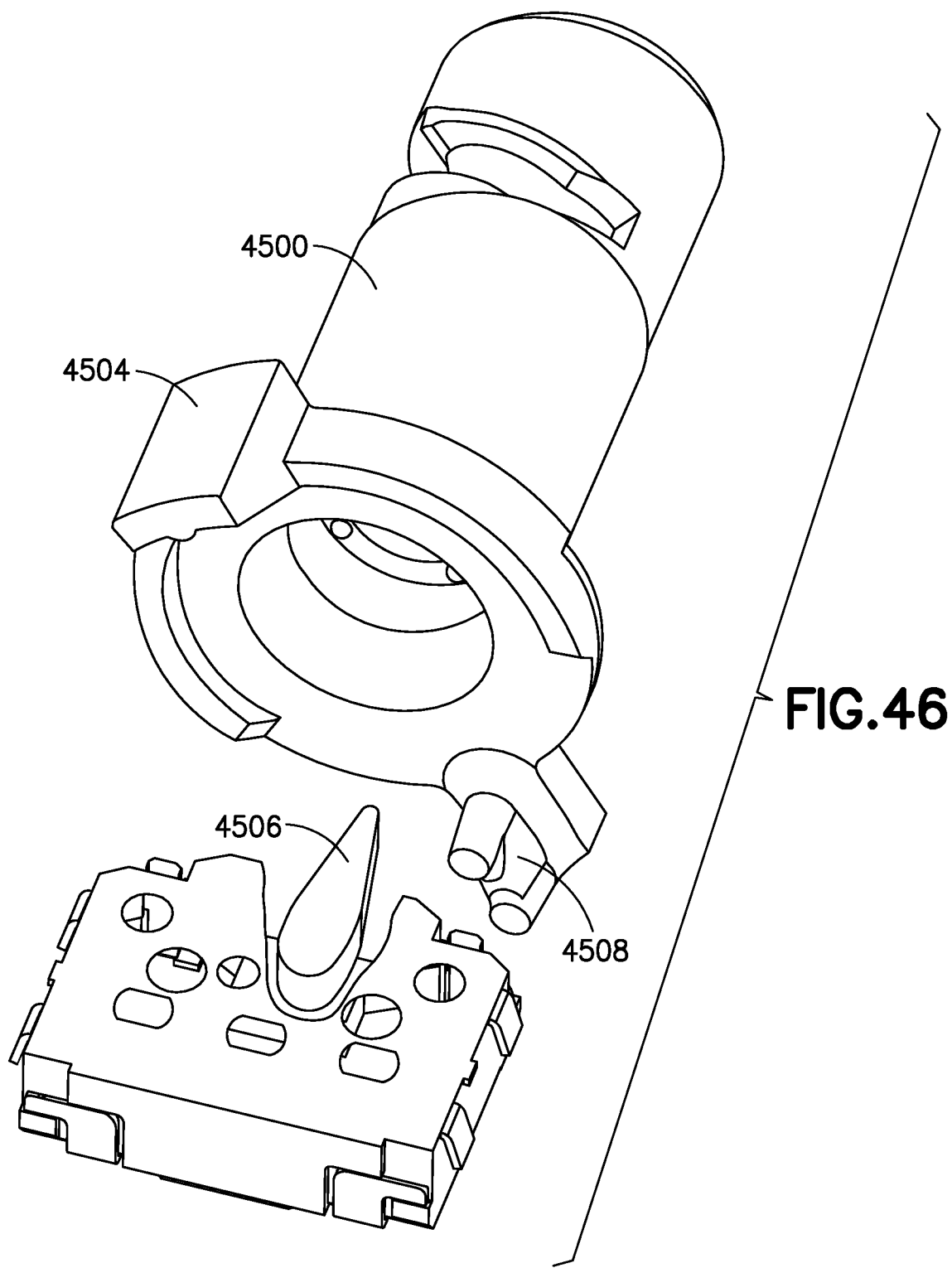
FIG. 46 is an isometric view of the limit switch and rotating sleeve according to the embodiment of FIG. 45.
Figure 47:
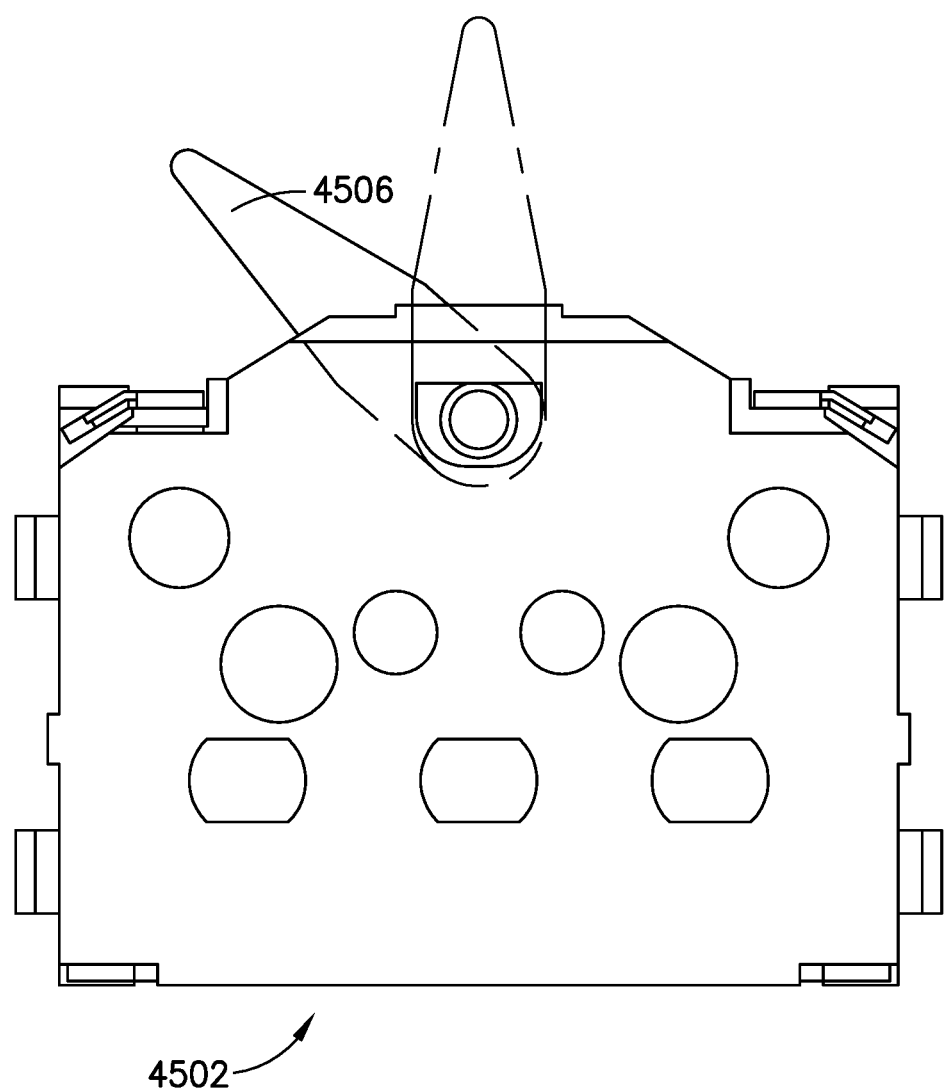
FIG. 47 is a top view of the limit switch of FIG. 45.
Figure 48:
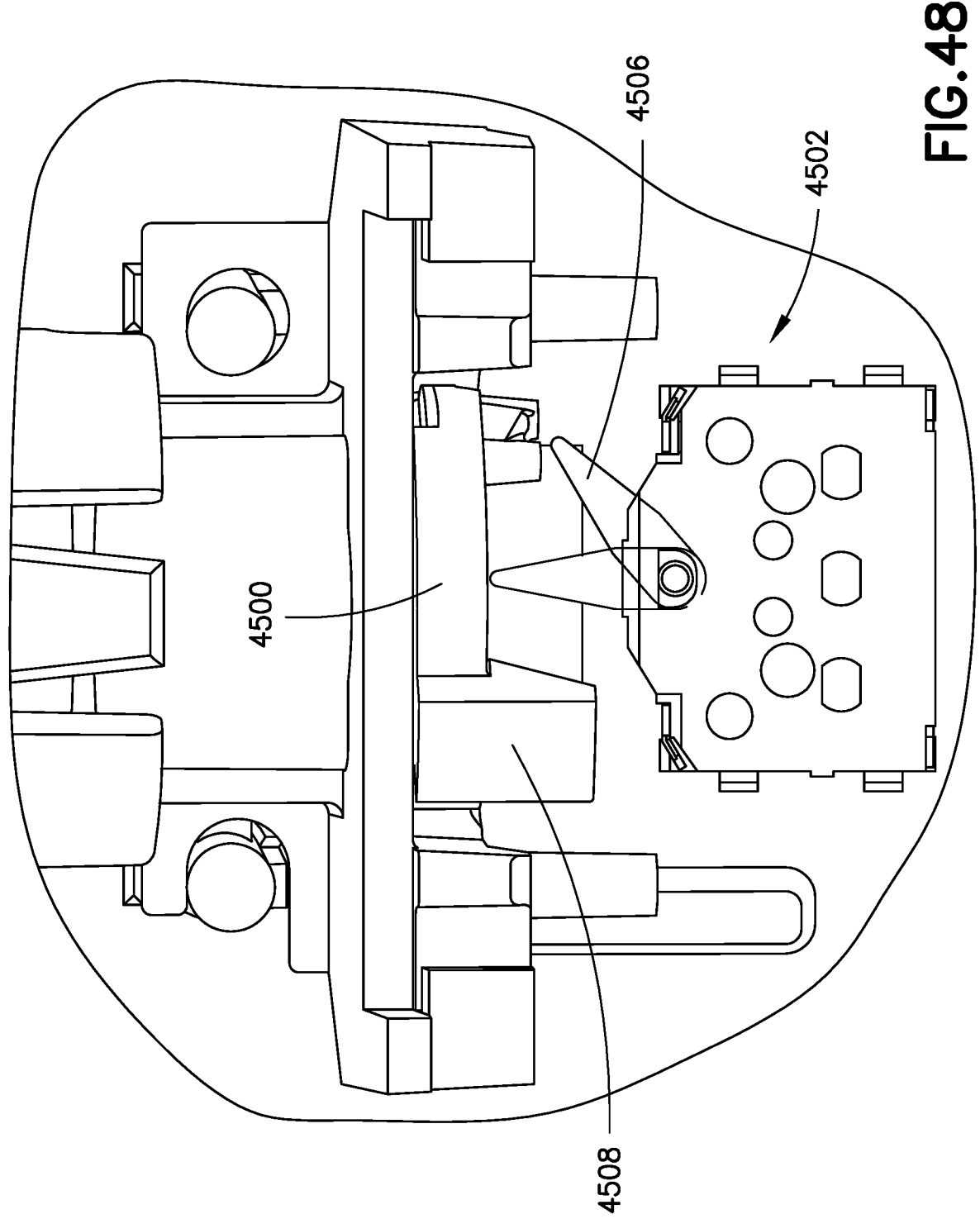
FIG. 48 is a top view of the limit switch and actuator arm of FIG. 45.
Figure 49:
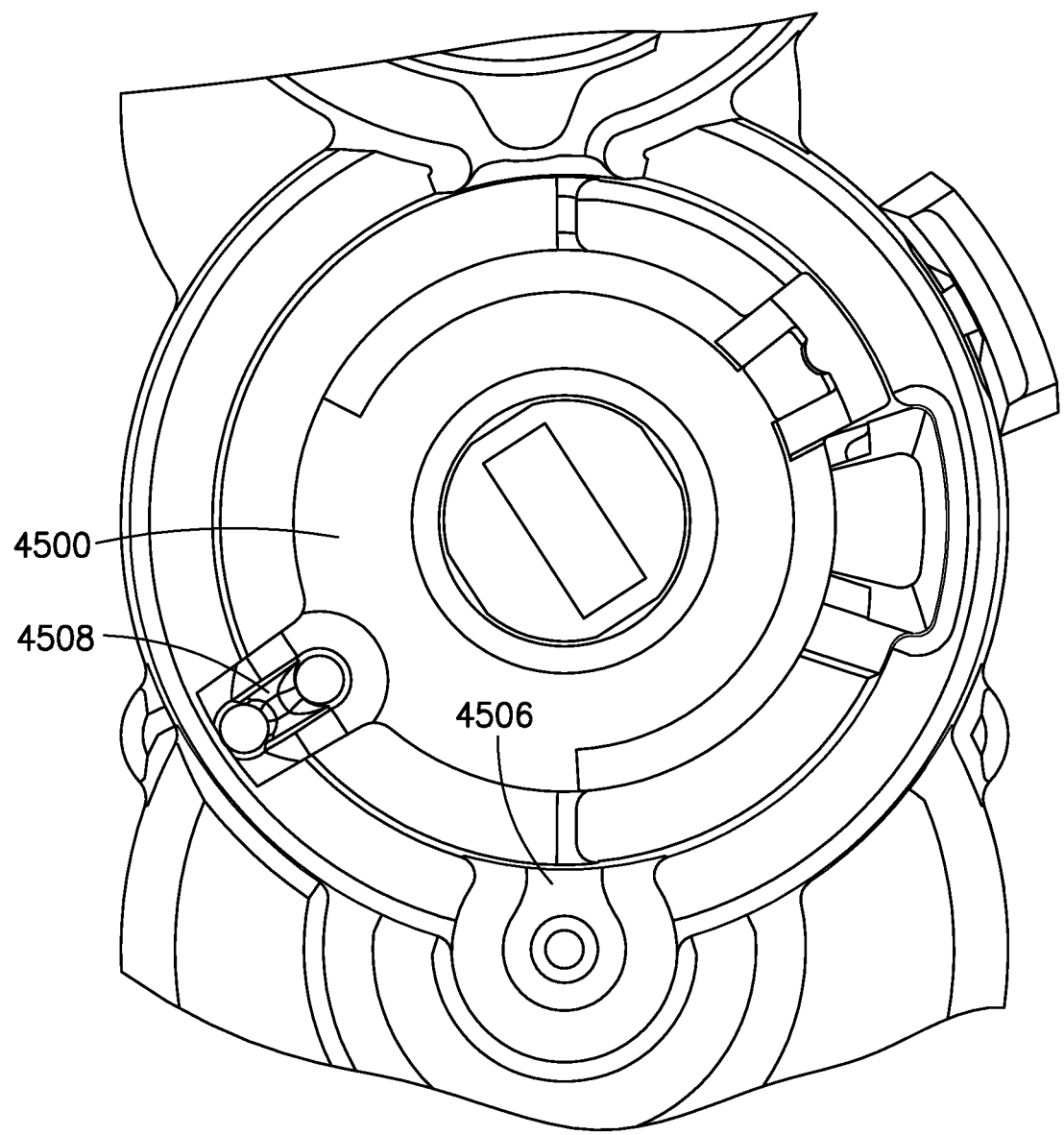
FIG. 49 is an end view of the rotating sleeve of FIG. 46.
Figure 50:
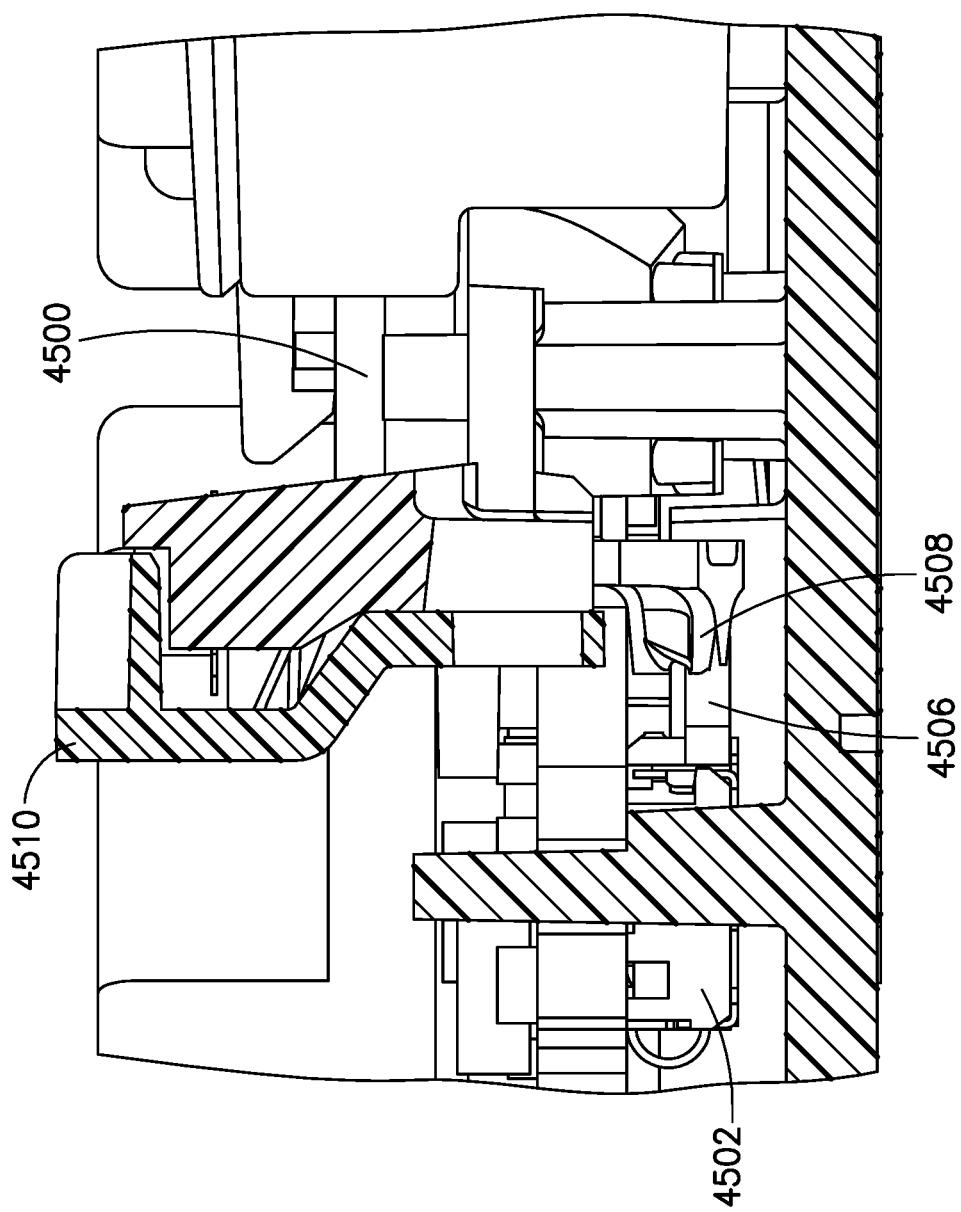
FIG. 50 is a cross sectional elevation view of the limit switch and actuator arm of FIG. 45.

FIG. 45 illustrates another exemplary embodiment having a modified sleeve 4500 and switching mechanism 4502. FIG. 46 is a perspective view of the modified sleeve 4500, which includes a detent 4504 similar to the sleeve described above to interact with an interlock (not shown). Switch mechanism 4502 includes a limit switch arm 4506 adapted to rotate in either direction away from its neutral position. Sleeve 4500 includes a switching lever (actuator arm) 4508 adapted to interact with the limit switch 4506 as the sleeve 4500 rotates. FIG. 47 illustrates how limit switch 4506 rotates about an axis. Switch mechanism 4502 provides electrical signals to indicate the position of limit switch 4506. FIG. 48 is a top view illustrating sleeve 4500 rotated to an orientation where limit switch 4506 has rotated to its maximum angle (alpha) from the neutral position. Further rotation of the sleeve causes the limit switch 4506 to be free of actuator arm 4508 and to return to its neutral position. This change in orientation of the switch arm indicates the end of the rotation of sleeve 4500 in one direction, and causes the rotational metering pump to reverse. FIG. 49 is a side elevation view oriented towards the sleeve face, illustrating the same interaction between limit switch 4506 and actuator arm 4508. FIG. 50 is a side elevation view, showing sleeve 4500 and switching mechanism 4502 incorporated into a patch pump, together with interlock collar 4510.

Figure 51A:
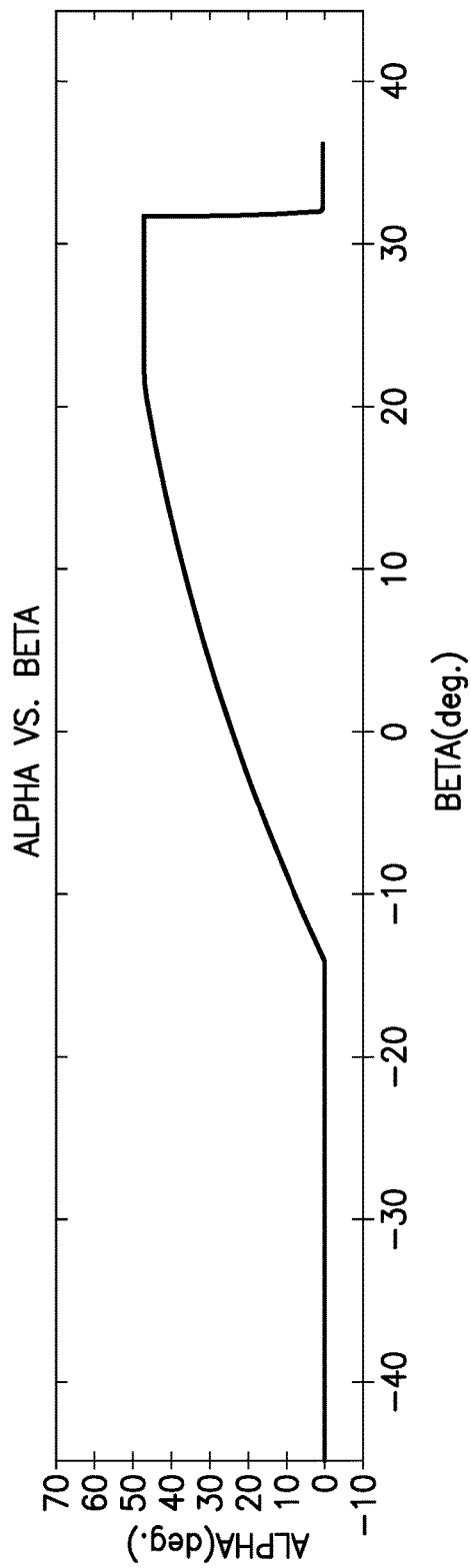
FIGS. 51A and 51B are charts illustrating relative displacement of the limit switch and rotating sleeve according to an exemplary embodiment of the invention.
Figure 51B:
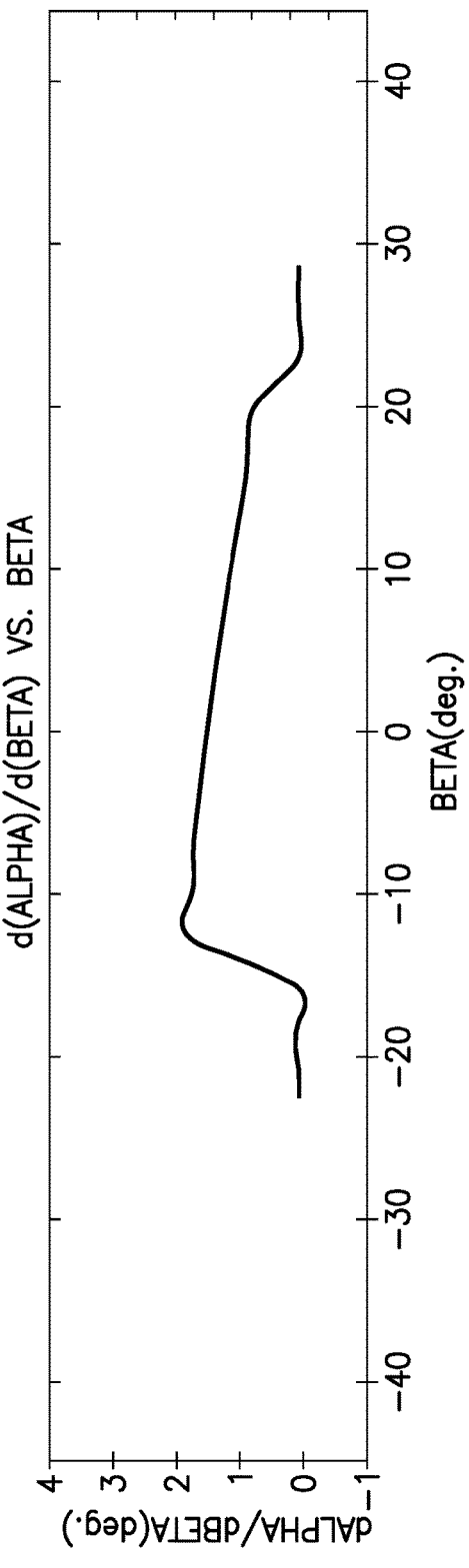
Figure 52:
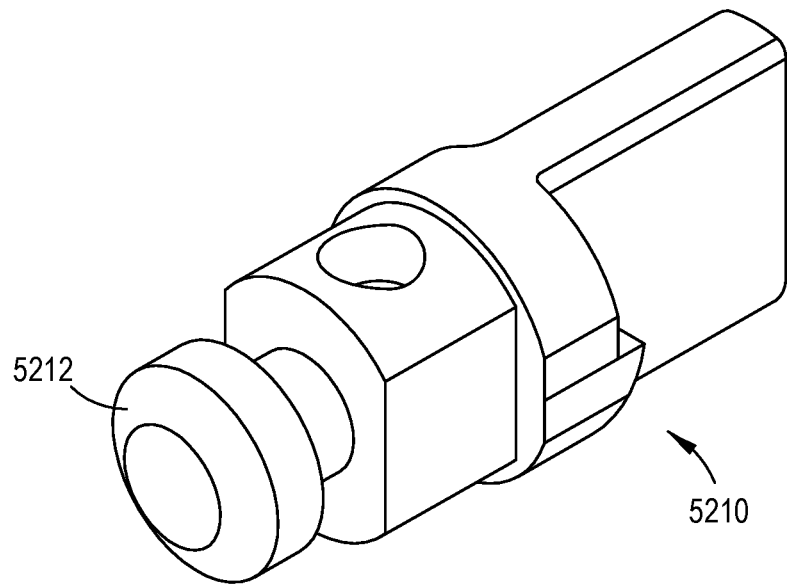
FIGS. 52 through 58 illustrate different perspective views of an improved plunger for a pump according to another exemplary embodiment of the invention.
Figure 53:
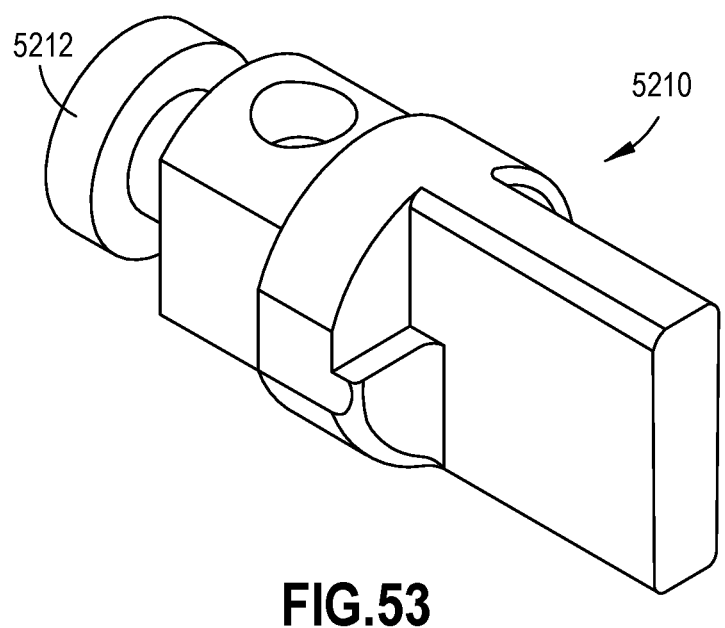
Figure 54:
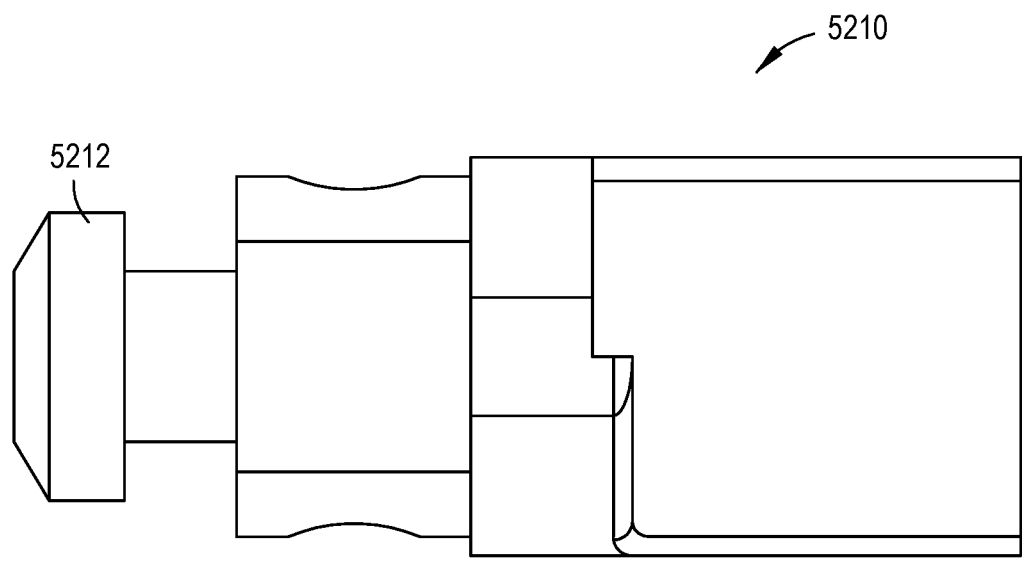
Figure 55:
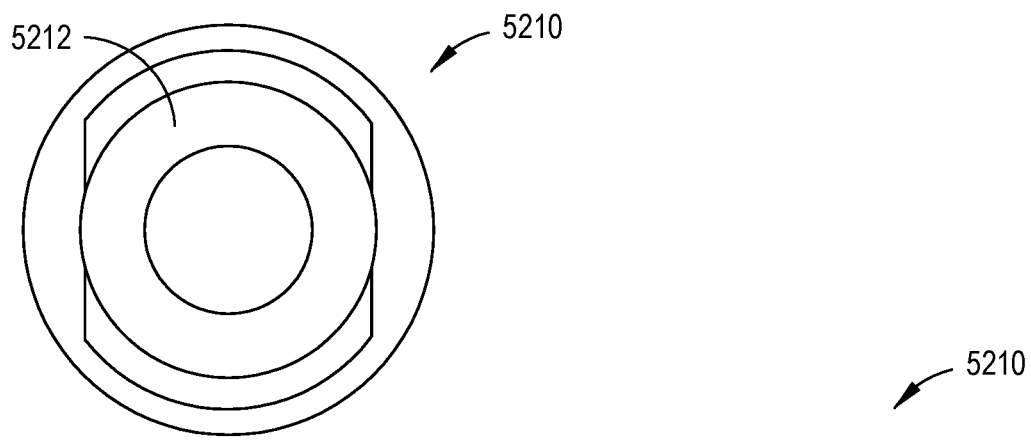
Figure 56:
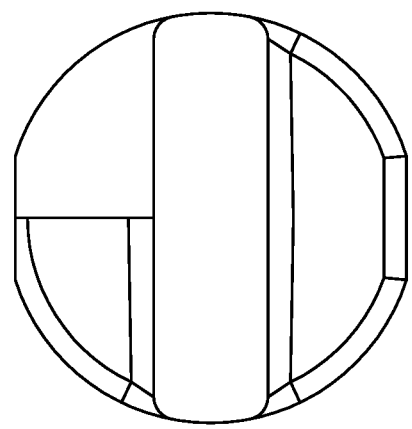
Figure 57:
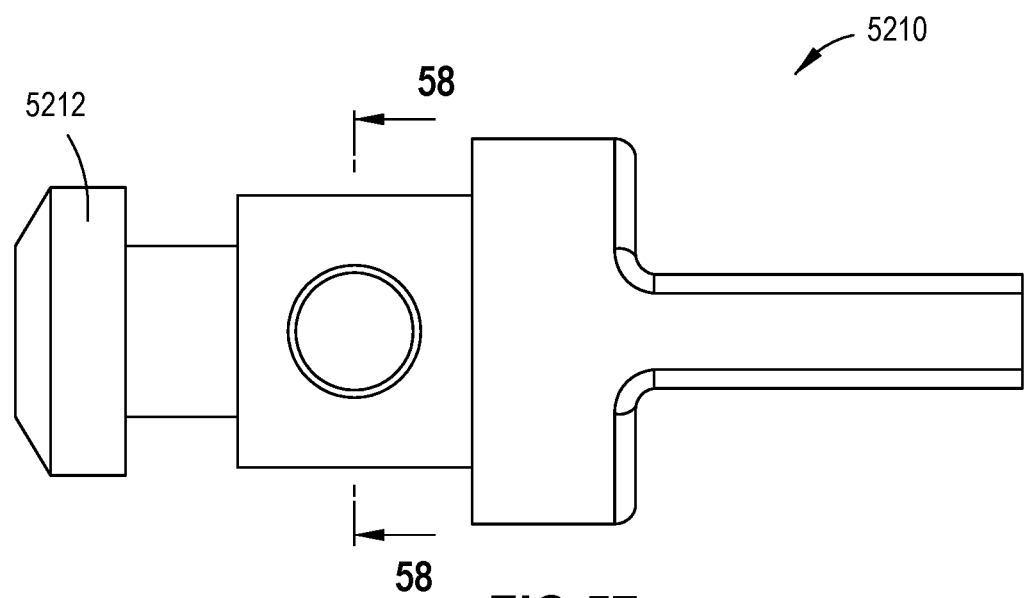
Figure 58:
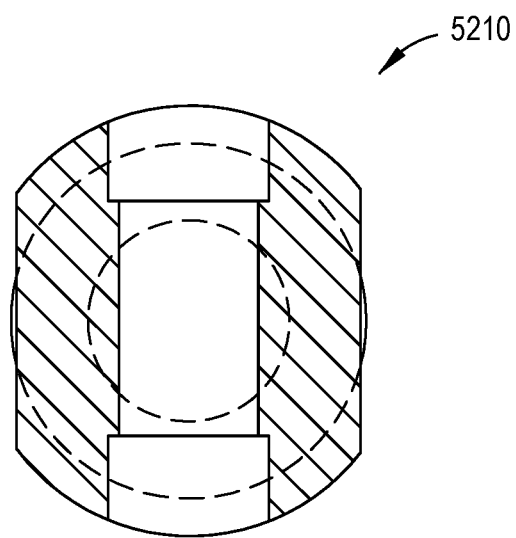
Figure 59:
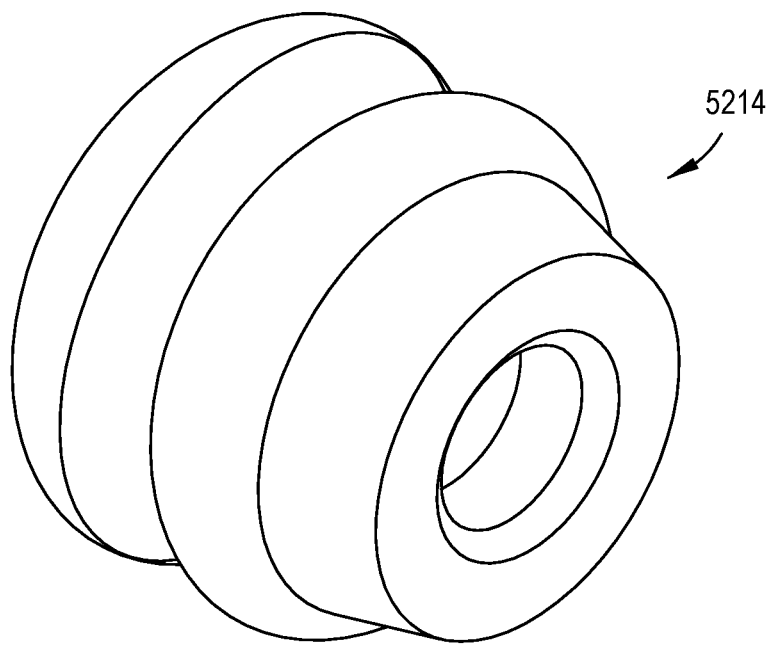
FIGS. 59 through 62 illustrate different perspective views of an overmolded seal for the improved plunger of FIGS. 52 through 58.
Figure 60:
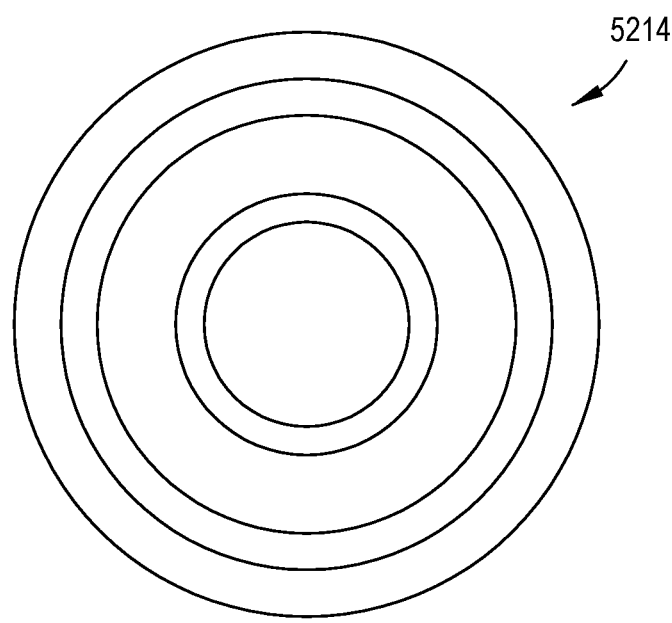
Figure 61:
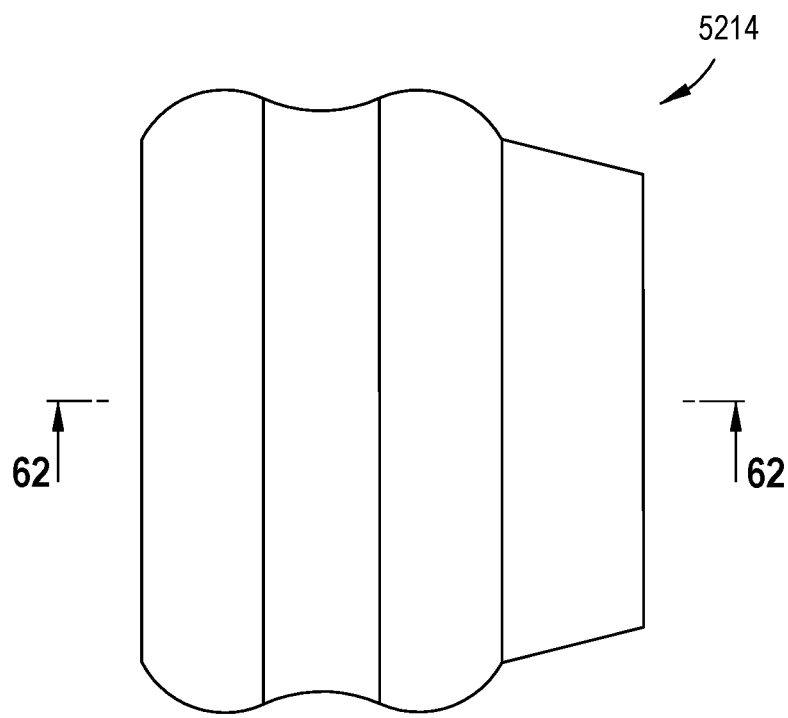
Figure 62:
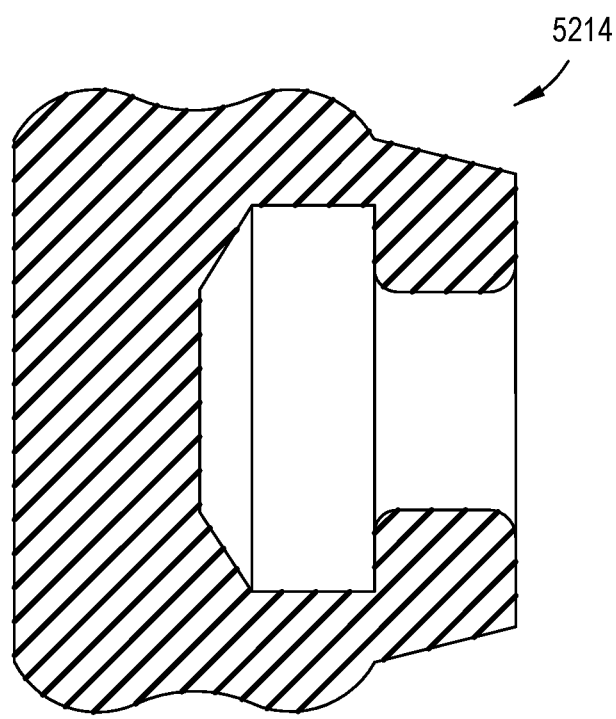
Figure 63:
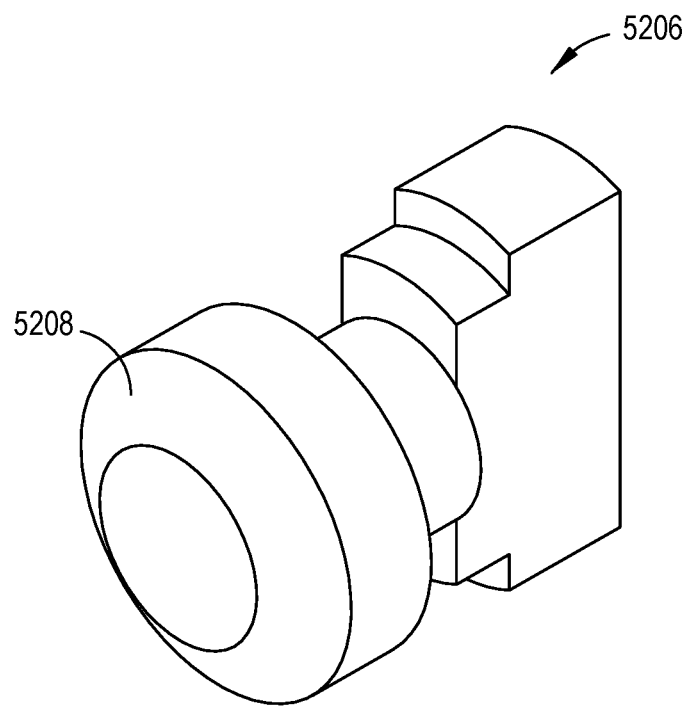
Figure 64:
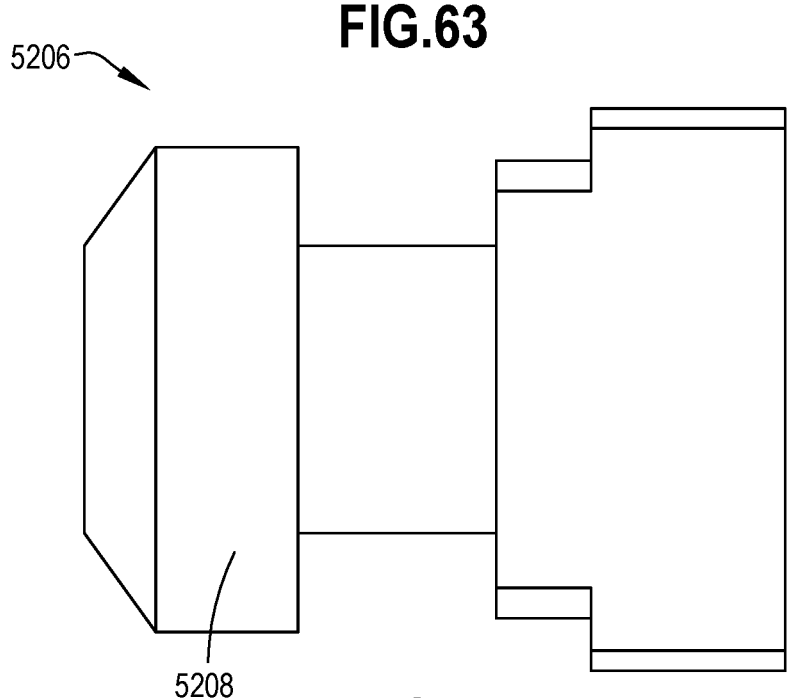
Figure 65:
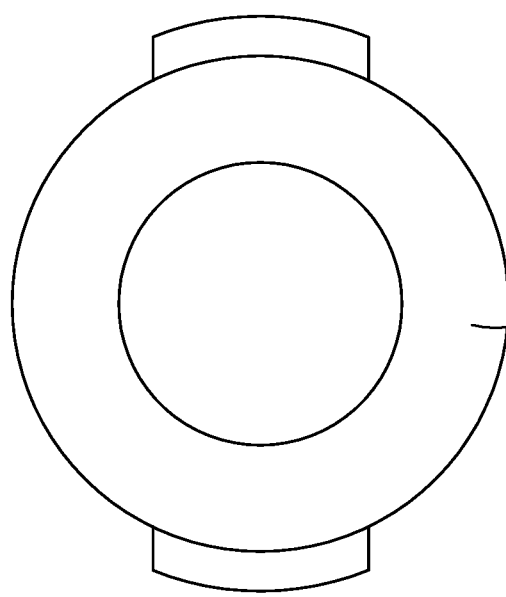
Figure 66:
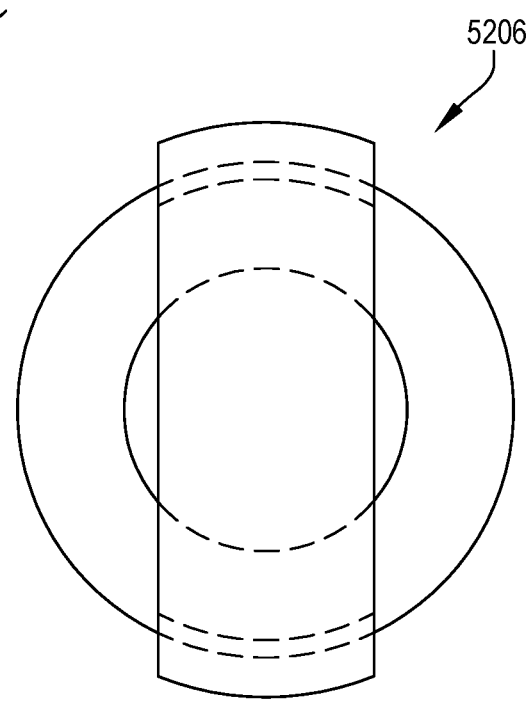
Figure 67:
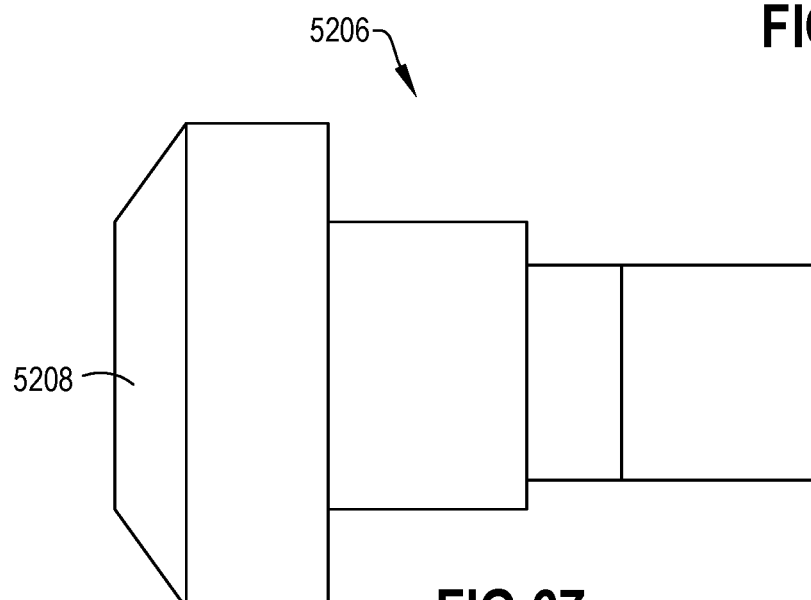

FIG. 51A illustrates the relative angular positions of the limit switch 4506 and actuator arm 4508. Alpha a is the angle of the limit switch 4506. Beta β is the angle of the rotating sleeve and actuating arm. FIG. 51B illustrate the relative change d(α)/d(β) vs. β. Reversal is preferably triggered at β=33°. As illustrated, as actuating arm 4608 rotates, it pushes limit switch 4506 away from the neutral position (α=0°). When actuating arm angle β reaches approximately 30β the actuating arm 4508 clears the limit switch 4506, and limit switch 4506 returns to neutral (α=0°), thereby initiating a reversal of the rotational pump. The same procedure occurs in reverse as the sleeve 4508 rotates in the other direction. Accordingly, the sleeve reciprocates back and forth.

Improved plunger and pump plug parts will now be described in connection with FIGS. 52-67. As will now be described the improved plunger 5210 and pump bottom 5206 improve the pump by making these parts easier to manufacture and assemble, and by eliminating a potential source of fluid leak from the prior design. Plunger 5210 is illustrated in multiple views in FIGS. 52-58. Plunger 5210 is substantially similar to the plunger 4010 illustrated in FIG. 40, except that O-ring 4008 is not needed, because a seal, to be described below, is overmolded onto the head 5212 of the plunger 5210.

Seal 5214 is illustrated in multiple views in FIGS. 59-62. Seal 5214 is advantageously overmolded onto the head 5212 of plunger 5210. Accordingly, the plunger with seal is advantageously manufactured in a two-shot molding process. Plunger 5210 is molded of a rigid plastic material, and then the seal 5214 is molded out of a viscoelastic elastomer onto the plunger 5210 as a second shot. The combined plunger 5210 and seal 5214 is more easily assembled into the overall pump, and reduces the chances for leakage present with an O-ring design.

A pump stopper or plug 5206 is illustrated in FIGS. 63-67. The stopper 5206 substantially corresponds to the plug 4006 in FIG. 40, except that a seal 5214 (the same or substantially similar seal part may be used for both the plunger 5210 and stopper 5206) is overmolded onto the head 5208 of stopper 5206 in place of an O-ring. Similar to the plunger 5210 described above, stopper 5206 and seal 5214 are preferably manufactured in a two-shot molding process. Stopper 5206 is molded from rigid plastic material, and seal 5214 is molded out of a viscoelastic elastomer onto the stopper 5206 as a second shot.

Figure 68:
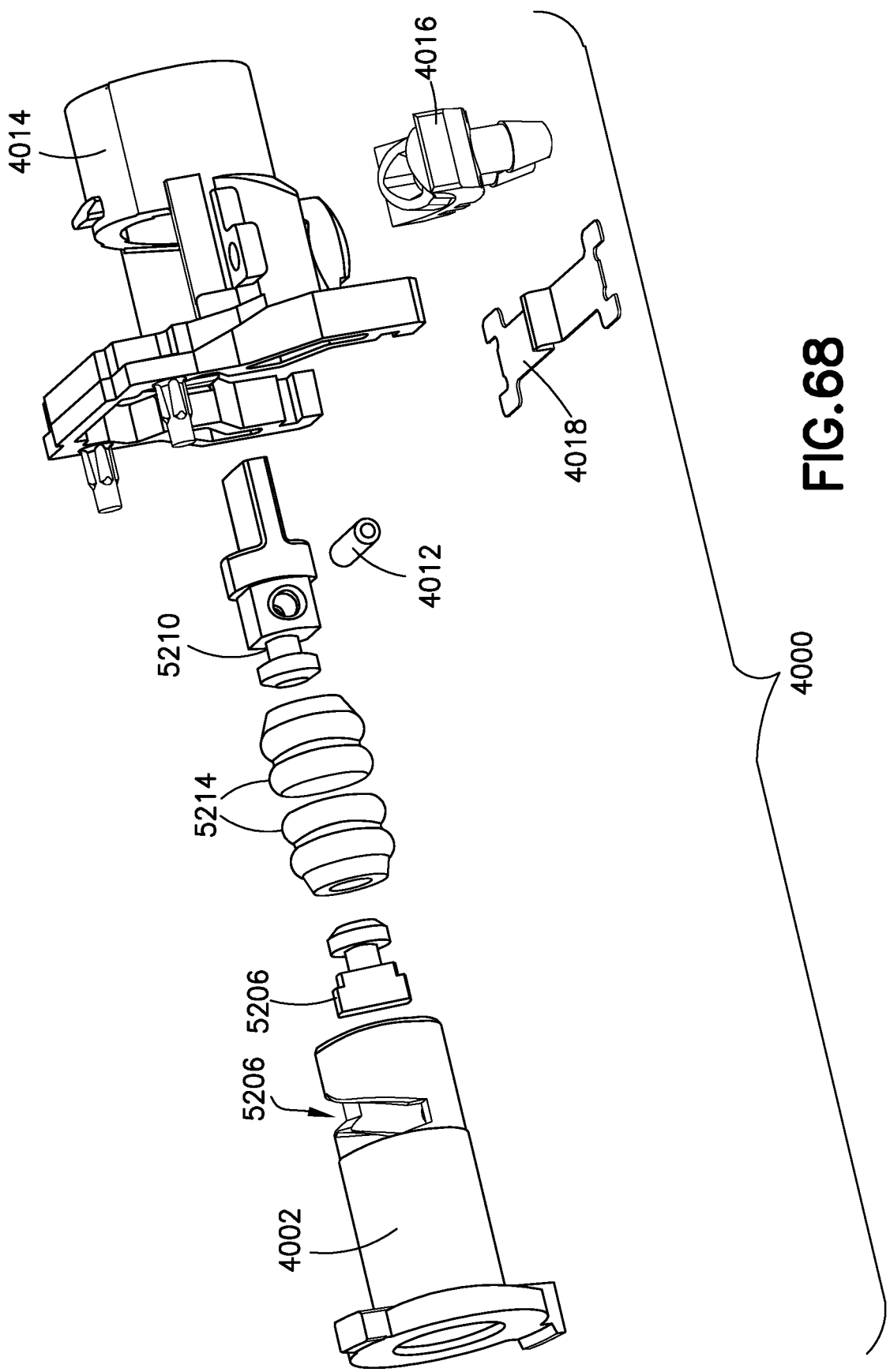
FIG. 68 is an exploded view of the pump system utilizing the improved plunger, plug and overmolded seals of an exemplary embodiment of the invention.

FIG. 68 illustrates an exploded view of metering assembly 4000, but with the improved plunger 5210, stopper 5206, and seals 5214. It will be appreciated by those of ordinary skill in the art that just as the plug 4006 was optional in the prior design and could be replaced with a wall 4404 as illustrated in FIG. 44, so the stopper 5206 is optional and replaceable with a similar wall.

Figure 69:
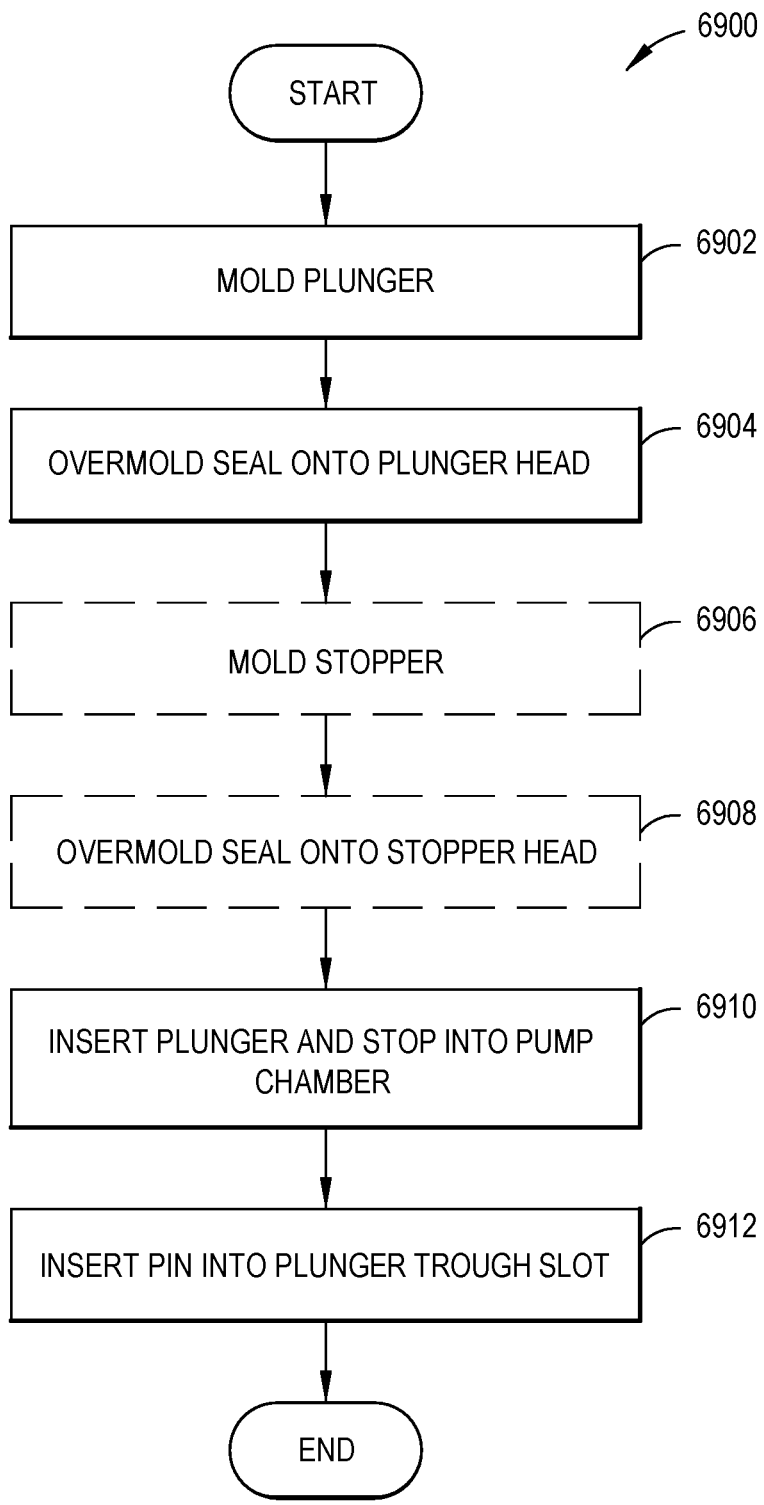
FIG. 69 is a flow chart of a method of manufacturing a pump according to an exemplary embodiment of the invention.

A method 6900 of manufacturing and assembling a pump according to an exemplary embodiment of the invention utilizing the overmolded parts described above will now be described in connection with FIG. 69. First, a plunger is molded from rigid plastic at step 6902. Next, a seal is overmolded onto a head of the plunger at step 6904. The seal is molded from a viscoelastic elastomer, and is dimensioned to fit within and seal a pump chamber. Optionally, a pump stopper is molded from rigid plastic at step 6906, and a seal is overmolded onto the head of the pump stopper at step 6908. The plunger and pump stopper are inserted into a pump chamber of a pump at step 6910. A pin is inserted into a hole in the plunger to enable translating of the plunger axially as the pump motor rotates the pump chamber at step 6912.

Although only a few illustrative embodiments of the present invention have been described in detail above, those skilled in the art will readily appreciate that many modifications are possible in the illustrative embodiments, and various combinations of the illustrative embodiments are possible, without materially departing from the novel teachings and advantages of this invention. Accordingly, all such modifications are intended to be included within the scope of this invention.

What is claimed is:

1. A rotational metering pump comprising:
   a manifold comprising a reservoir port in fluid communication with a fluid reservoir and a cannula port in fluid communication with a cannula;
   a sleeve comprising a side hole, the sleeve adapted to rotate axially within the manifold between a first orientation with said side hole aligned with the reservoir port and a second orientation with said side hole aligned with the cannula port, the sleeve further comprising a helical groove having a first end and a second end;
   a plunger comprising an overmolded seal molded over a plunger head adapted to rotate and translate axially within the sleeve, wherein axial translation of the plunger within the sleeve changes a pump volume, the pump volume being in fluid communication with the side hole of the sleeve, the plunger further comprising a coupling member adapted to move within the helical groove and between the first end and the second end of the helical groove to cause the plunger to translate axially within the sleeve as the plunger is rotated;
   a motor adapted to rotate the plunger in a first direction causing the pump volume to increase when the sleeve is in the first orientation, and to rotate the sleeve and plunger together when the coupling member reaches the first end of the helical groove, such that the sleeve moves into the second orientation;
   further comprising a rotational limit switch, the rotational limit switch causing the motor to reverse direction after the sleeve rotates to orient the side hole with the cannula port;
   wherein the sleeve comprises an actuator arm fixed to the sleeve that moves a limit switch as the sleeve rotates in either direction, and wherein the limit switch is biased to return to a center position when the actuator arm rotates past the limit switch.

2. The rotational metering pump of claim 1, wherein the plunger further comprises a tab and the manifold comprises a window, and the tab moves within the window to prevent the sleeve from translating axially relative to the manifold as the sleeve rotates within the manifold.

3. The rotational metering pump of claim 1, further comprising a plug comprising a seal overmolded onto a head of the plug, the plug being inserted into the sleeve to form a surface of the pump volume opposing the plunger.

4. The rotational metering pump of claim 1, wherein the sleeve comprises a face stop that forms a surface of the pump volume opposing the plunger.

5. The rotational metering pump of claim 1, further comprising a seal on a plug to form a liquid tight seal between the plug and the sleeve.

6. The rotational metering pump of claim 1, wherein the motor comprises an output gear having a slot to receive a tab of the plunger, the slot permitting the plunger to move axially relative to the motor while the motor rotates the plunger.

7. The rotational metering pump of claim 1, further comprising an interlock that prevents rotation of the sleeve when a torque applied to the sleeve is below a predetermined threshold, and wherein the interlock permits the sleeve to rotate when the torque exceeds the predetermined threshold.

8. The rotational metering pump of claim 7, wherein the sleeve comprises a detent that engages a bump on the interlock to prevent rotation of the sleeve, and wherein the interlock flexes to permit the detent to move past the bump on the interlock when a torque applied to the sleeve exceeds the predetermined threshold.

9. The rotational metering pump of claim 1, further comprising at least one port seal forming a liquid tight seal between the sleeve and the reservoir port.

10. The rotational metering pump of claim 1, further comprising at least one port seal forming a liquid tight seal between the sleeve and the cannula port.

11. The rotational metering pump of claim 9, wherein the port seal is a unitary elastomeric part.

\* \* \* \* \*